US006784167B2

United States Patent
Wood et al.

(10) Patent No.: US 6,784,167 B2
(45) Date of Patent: Aug. 31, 2004

(54) 17-BETA-HYDROXYSTEROID DEHYDROGENASE-II INHIBITORS

(75) Inventors: Jill E. Wood, North Haven, CT (US); Jeremy L. Baryza, Mountain View, CA (US); Catherine R. Brennan, Hamden, CT (US); Soongyu Choi, Trumbull, CT (US); James H. Cook, East Hampton, CT (US); Brian R. Dixon, Woodbridge, CT (US); Paul P. Ehrlich, Duesseldorf-Wittlaer (DE); David E. Gunn, Hamden, CT (US); Ian McAlexander, Pocatello, ID (US); Peiying Liu, Madison, CT (US); Derek B. Lowe, Hamden, CT (US); Anikó M. Redman, Derby, CT (US); William J. Scott, Guilford, CT (US); Yamin Wang, Sandy Hook, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 73 days.

(21) Appl. No.: 09/967,430

(22) Filed: Sep. 28, 2001

(65) Prior Publication Data

US 2003/0087952 A1 May 8, 2003

Related U.S. Application Data

(60) Provisional application No. 60/236,681, filed on Sep. 29, 2000, and provisional application No. 60/257,435, filed on Dec. 22, 2000.

(51) Int. Cl.[7] ........................ A61K 31/40; A61K 31/44; A61P 35/00; C07D 207/00; C07D 409/00
(52) U.S. Cl. .................. 514/63; 514/227.8; 514/237.2; 514/254.01; 514/274; 514/314; 514/343; 514/365; 514/411; 514/414; 514/422; 514/424; 544/58.2; 544/58.7; 544/60; 544/141; 544/316; 544/372; 546/167; 546/278.4; 548/204; 548/205; 548/406; 548/450; 548/468; 548/517; 548/518; 548/525; 548/526; 548/527; 548/551
(58) Field of Search ................. 514/63, 227.8, 514/237.2, 254.01, 274, 314, 343, 365, 411, 414, 422, 424; 544/58.2, 58.7, 60, 141, 316, 372; 546/167, 278.4; 548/204, 205, 406, 450, 468, 517, 518, 525, 526, 527, 551

(56) References Cited

U.S. PATENT DOCUMENTS 4,731,455 A   3/1988   Hartwig ...................... 548/544

FOREIGN PATENT DOCUMENTS

DE   3624102   1/1988

OTHER PUBLICATIONS

Vihko et al., Structure and function of 17.beta.–hydroxysteroid Dehydrogenase Type 1 and Type 2, Molecular and Cellular Endocrinology, vol. 171, No. 1–2, pp. 71–76, 2001.*

* cited by examiner

Primary Examiner—Brenda Coleman

(57) ABSTRACT

17-beta-hydroxysteroid dehydrogenase-II inhibitors having the structural formula (I)

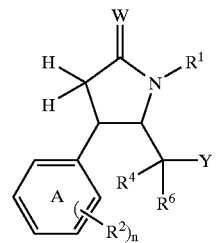

wherein the phenyl group labeled A and the group —$C(R^4)(R^6)Y$ are oriented cis to each other; W represents O or S; $R^1$ represents —H or optionally substituted —$(C_1$–$C_4)$alkyl; n represents 0 or an integer of 1–3; and $R^2$ represents any of a variety of substituents on ring A. $R^4$ generally represents —H but may be a bond terminating at the ortho position of ring A. Y represents fluorine, —$OR^5$, or —$SR^5$, and $R^5$ represents —H, optionally substituted —$(C_1$–$C_4)$alkyl, optionally substituted -phenyl, optionally substituted —$(C_1$–$C_4)$alkyl-phenyl, or optionally substituted —$(C_1$–$C_4)$ acyl. $R^6$ represents any of a variety of groups as defined in the specification and claims, including heteroaryl, arylalkyl, heteroarylalkyl, arylalkenyl, heteroarylalkenyl, alkynyl, arylalkynyl, heteroarylalkynyl, aryl, and indolyl. Pharmaceutically acceptable salts and N-oxides of these materials are also included. Also claimed are pharmaceutical compositions containing these materials and methods of using them.

17 Claims, No Drawings

17-BETA-HYDROXYSTEROID DEHYDROGENASE-II INHIBITORS

This application claims the benefit of U.S. Provisional Application No. 60/236,681 filed Sep. 29, 2000, and U.S. Provisional Application No. 60/257,435, filed Dec. 22, 2000.

FIELD

This invention relates to pyrrolidinone and pyrrolidinthione pharmaceuticals, and more particularly, to 1-methyl-4-phenylpyrrolidin-2-ones, pharmaceutical compositions containing them, and their use in modulating 17β-Hydroxysteroid Dehydrogenase type II (17β-HSD II) enzyme mediated processes.

BACKGROUND

Microsomal 17β-Hydroxysteroid Dehydrogenase of human endometrium and placenta (designated 17β-HSD type II) was cloned by expression cloning, and found to be equally active using androgens and estrogens as substrates for oxidation (Andersson S., Molecular genetics of androgenic 17β-Hydroxysteroid Dehydrogenases. J. Steroid Biochem. Molec. Biol., 55, 533–534 (1995)). The recombinant 17β-HSD type II converts the highly active 17β-hydroxysteroids such as estradiol ($E_2$), testosterone (T), and dehydrotestosterone (DHT) to their inactive keto forms. In addition, the type II enzyme can, to a lesser extent, also convert 20β-hydroxyprogesterone (20βP) to progesterone (P) (Wu L, Einstein M, Geissler W M, Chan H K, Elliston K O, and Andersson S., Expression cloning and characterization of human 17β-hydroxysteroid dehydrogenase type 2, a microsomal enzyme possessing 20a-hydroxysteroid dehydrogenase activity. J. Biol. Chem., 268(12), 964–969 (1993)). The broad tissue distribution together with the predominant oxidative activity of 17β-HSD II suggest that the enzyme may play an essential role in the inactivation of highly active 17β-hydroxysteroids, resulting in diminished sex hormone action in target tissues. Dong and colleagues (Dong Y, Qiu Q Q, Debear J, Lathrop W F, Bertolini D, Tamburini P P, 17p-hydroxysteroid dehydrogenases in human bone cells. J. Bone Min. Res., 13, 1539–1546 (1998)) showed significant 17β-HSD II activity in cultured human osteoblasts and osteoblast-like osteosarcoma cells MG63 and TE85, but not in SaOS-2. The potential for interconversion of $E_1$ to $E_2$, T to A, and DHT to A by bone cells could therefore represent important mechanism for the local regulation of intracellular ligand supply for the estrogen and androgen receptors in the osteoblasts and other steroid sensitive cells. This modulation of steroid levels may be employed for a wide variety of indications, including those shown in the lettered paragraphs below.

A1) for the prevention and treatment of osteoporosis (Turner et al., Endocr. Rev., 16, 275 (1994); Lindsay et al., Lancet, 1, 1038 (1976); Stevenson et al., Lancet, 336, 265 (1990); Lindsay et al., Obstet. Gynecol., 76, 290 (1990); Lindsay and Cosman: The Pharmacology of Estrogensin Osteoporosis. In: Principles of Bone Biology, Ed.: J P Bilezikian, L G Raisz, G A Rodan, Academic Press, 1063 (1996); Schmidt et al.: Anabolic Steroid Effects on Bone in Women. In: Principles of Bone Biology, Ed.: J P Bilezikian, L G Raisz, G A Rodan, Academic Press, 1125 (1996).

B1) for the treatment of ovarian cancer (Moghrabi et al., TEM, 9, 265 (1998); Sato et al., Cancer Res., 51, 5118 (1991));

B2) for the treatment of breast cancer (Risinger et al., Nature Genet., 7, 98 (1994); Tremblay, et al., J. Steroid Biochem. Mol. Biol., 66, 179 (1998); Speirs et al., Brit. J. Cancer, 81, 690 (1999));

B3) for the treatment of endometrial cancer (Miettinen et al., Biochem. J., 314, 839 (1996));

B4) for the treatment of endometriosis (Vihko et al., Med. Manage. Endometriosis, [Symp.] 79 (1984); Vihko et al., Ann. N.Y. Acad. Sci., 622, 392 (1991));

C1) for the treatment of prostate cancer (Elo et al., J. Cancer, 66, 37 (1996));

D1) for the treatment of acne (Odlind et al., Clin. Endocrinol., 16, 243 (1982));

D2) for the treatment of psoriasis (Henseler et al., J. Am. Acad. Dermatol., 13, 450 (1985));

D3) for the treatment of androgen-dependent hair-loss (Hughes et al., Endocrinology, 138, 3711 (1997));

E1) non-insulin-dependent diabetes mellitus (Corbould et al., J. Clin. Endocrinol. Metab., 83, 187 (1998));

F1) for cholesterol lowering (Karjalainen, A. et al., Arterioscler.Thromb.Vasc.Biol., 20 1101 (2000)).

DESCRIPTION

In its broadest embodiment, this invention relates to a compound having the structural formula

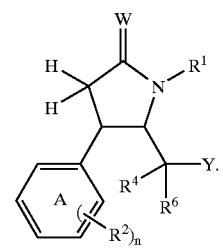

(I)

In formula (I), the phenyl group labeled A and the group $—C(R^4)(R^6)Y$ are oriented cis to each other; W represents O or S; $R^1$ represents —H or —($C_1$–$C_4$)alkyl which is optionally substituted with up to three halogens; and the subscript n represents 0 or an integer of 1–3.

Substituents $R^2$ represent $—N(R^3)_2$; $—OR^3$; $—SR^3$; -halogen; -phenyl which is optionally substituted with halogen up to perhalo; or —($C_1$–$C_4$)alkyl which is optionally substituted with halogen, $—OR^3$, or $SR^3$. The number of substituents on this alkyl group is up to three for halogen, and up to two for any combination of the $—OR^3$ and $—SR^3$ moieties.

$R^3$ represents —H or —($C_1$–$C_4$)alkyl which is optionally substituted with up to three halogens.

$R^4$ represents —H or a bond terminating at the ortho position of phenyl ring A.

Y represents fluorine, $—OR^5$, or $—SR^5$.

$R^5$ represents —H; —($C_1$–$C_4$)alkyl optionally substituted with up to three halogens; or -phenyl which is optionally substituted with halogen, $—OR^{3A}$, $—SR^{3A}$, or $—R^{3A}$, provided, however, that $R^5$ may represent an optionally substituted phenyl group only when $R^6$ represents H. The number of halogen, $—OR^{3A}$, $—SR^{3A}$, or $—R^{3A}$ substituents on this phenyl $R^5$ group is up to perhalo for halogen, and up to two for any combination of the $—OR^{3A}$, $—SR^{3A}$, and $—R^{3A}$ moieties. $R^{3A}$ represents —($C_1$–$C_4$)alkyl optionally substituted with up to three halogens. $R^5$ may also represent —($C_1$–$C_4$)alkyl-phenyl in which the alkyl portion is optionally substituted with up to three halogens, and the phenyl portion is optionally substituted with halogen, $—OR^{3A}$, —SR$^{3A}$, or —R$^{3A}$. The number of substituents on the phenyl portion is up to perhalo for halogen, and up to two for any combination of the —OR$^{3A}$, —SR$^{3A}$, and —R$^{3A}$ moieties. R$^5$ may also represent —(C$_1$–C$_4$)acyl optionally substituted with up to three halogens.

R$^6$ represents a group as defined in the following numbered subparagraphs 1) through 12).

1) R$^6$ may be —H; with the proviso that when R$^6$ is H, then Y is OR$^5$ wherein R$^5$ is phenyl which is optionally substituted with halogen, —OR$^{3A}$, —SR$^{3A}$, or —R$^{3A}$. The number of substituents on this phenyl group is up to perhalo for halogen, and up to two for any combination of the —OR$^{3A}$, —SR$^{3A}$, and —R$^{3A}$ moieties.

2) R$^6$ may be

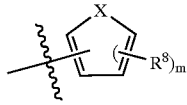

in which m represents 0 or an integer of 1–3; with the further proviso that when W is O and Y is OH, at least one of m and n is nonzero. In this partial structure, X represents O or S; and R$^8$ represents any of a variety of substituents listed below as items a) through i).

a) R$^8$ may be —(C$_6$–C$_{10}$)aryl, which is optionally substituted with one or more substituents selected from -halogen; —N(R$^3$)$_2$; —OR$^3$; —SR$^3$; —CO$_2$R$^3$; —NO$_2$; —CN; —(C$_1$–C$_6$)alkyl optionally substituted with up to three halogens; -phenyl which is optionally substituted with halogen, —OR$^{3A}$, —SR$^{3A}$, or —R$^{3A}$ and in which the number of substituents is up to perhalo for halogen and up to two for any combination of the —OR$^{3A}$, —SR$^{3A}$, and —R$^{3A}$ moieties; —heteroaryl of 5 members and containing 1–2 heteroatoms selected from N, O, and S; —NHCOR$^9$ in which R$^9$ represents R$^{3A}$ or -phenyl which is optionally substituted with halogen up to perhalo; —NHCONHR$^9$; and —NHSO$_2$R$^9$. The number of substituents on this (C$_6$–C$_{10}$)aryl group R$^8$ is up to perhalo for halogen, and up to three for any combination of the —N(R$^3$)$_2$, —OR$^3$, —SR$^3$, —CO$_2$R$^3$, —NO$_2$, —CN, —(C$_1$–C$_6$)alkyl, -phenyl, -heteroaryl, —NHCOR$^9$ —NHCONHR$^9$, and —NHSO$_2$R$^9$ moieties.

b) R$^8$ may be -heteroaryl of 5–10 members and containing 1–3 heteroatoms selected from N, O, and S; and being optionally substituted with halogen, —N(R$^3$)$_2$, —OR$^{3A}$, —SR$^{3A}$, —CO$_2$R$^3$, —NO$_2$, —CN, or —(C$_1$–C$_6$)alkyl which in turn is optionally substituted with up to three halogens. The number of substituents on this heteroaryl R$^8$ group is up to perhalo for halogen, and up to two for any combination of the —N(R$^3$)$_2$, —OR$^{3A}$, —SR$^{3A}$, —CO$_2$R$^3$, —NO$_2$, —CN, and —(C$_1$–C$_6$)alkyl moieties.

c) R$^8$ may be —(C$_2$)alkynyl-R$^{10}$ in which R$^{10}$ represents H; R$^{3A}$; or -phenyl which in turn is optionally substituted with halogen, —OR$^3$, —SR$^3$, or —R$^{3A}$. The number of substituents on this phenyl group is up to perhalo for halogen, and up to two for any combination of the —OR$^3$, —SR$^3$, and —R$^{3A}$ moieties.

d) R$^8$ may be —(C$_1$–C$_4$)alkyl-R$^{11}$ in which the alkyl portion is optionally substituted with halogen, —OR$^3$, or —SR$^3$; the number of these substituents being up to three for halogen, and up to two for any combination of the —OR$^3$ and —SR$^3$ moieties. In this substituent, R$^{11}$ represents —H provided that m is 2 or 3; or R$^{11}$ represents -phenyl optionally substituted with halogen up to perhalo.

e) R$^8$ may be —S(O)$_{0-2}$R$^{12}$ in which R$^{12}$ represents —(C$_1$–C$_6$)alkyl optionally substituted with halogen; or

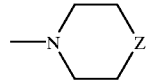

in which Z represents O, S(O)$_{0-2}$, C(R$^3$)$_2$, or NR$^{13}$ in which: R$^{13}$ represents R$^{3A}$, or -phenyl which is optionally substituted with halogen, —OR$^{3A}$, SR$^{3A}$, or —(C$_1$–C$_2$)alkyl optionally substituted with up to three halogens. The number of these substituents on phenyl is up to perhalo for halogen, and up to two for any combination of the —OR$^{3A}$, SR$^{3A}$, and —(C$_1$–C$_2$)alkyl moieties. R may also be -phenyl which is optionally substituted with halogen, —OR$^3$, or R$^{3A}$. The number of these substituents on this phenyl substituent is up to perhalo for halogen, and up to two for any combination of the —OR$^3$ and —R$^{3A}$ moieties. R$^{12}$ may also be -heteroaryl of 5–6 members and containing 1–3 heteroatoms selected from N, O, and S.

f) R$^8$ may be —C(R$^{14}$)=CHR$^{14}$ in which R$^{14}$ represents H; -halogen; —OR$^{3A}$; or phenyl optionally substituted with halogen or with —R$^{3A}$. The number of substituents on phenyl is up to perhalo for halogen, and up to two for —R$^3$A moieties. When 2 such alkenyl groups are adjacent to each other, they may be joined, and taken together with the ring atoms to which they are attached, constitute a fused 6-membered ring.

g) R$^8$ may be

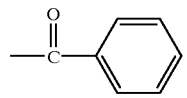

optionally substituted with halogen, —OR$^{3A}$ or —(C$_1$–C$_6$)alkyl which is in turn optionally substituted with up to three halogens. The number of these substituents on phenyl is up to perhalo for halogen, and up to two for any combination of the —OR$^{3A}$ or —(C$_1$–C$_6$)alkyl moieties.

h) R$^8$ may be

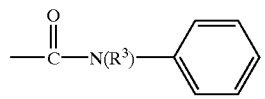

in which the phenyl ring is optionally substituted with halogen, —OR$^{3A}$, or —(C$_1$–C$_6$)alkyl which is in turn optionally substituted with up to three halogens. The number of the substituents on phenyl is up to perhalo for halogen, and up to two for any combination of said —OR$^{3A}$ and —(C$_1$–C$_6$)alkyl moieties.

i) $R^8$ may be

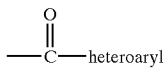

in which the heteroaryl ring contains 5–6 members and up to 3 heteroatoms selected from N, O, and S, and is optionally substituted with up to 2 substitutents $R^{3A}$.

3) $R^6$ may be —$(C_1-C_4)$alkyl-$R^{15}$ in which the alkyl portion is optionally substituted with up to three halogens. In this substituent, $R^{15}$ represents -phenyl which is optionally substituted with halogen, —$R^{3A}$, —$OR^{3A}$, or with -phenyl' which is in turn optionally substituted with halogen up to perhalo. The number of these substituents on the $R^{15}$ phenyl is up to perhalo for halogen, and up to two for any combination of the —$R^{3A}$, —$OR^{3A}$, or -phenyl' moieties. $R^{15}$ may also be a heteroaryl ring of 5–6 members and containing up to 3 heteroatoms selected from N, O, and S, and optionally bearing up to 2 substituents selected from halogen, —$R^{3A}$, —$OR^{3A}$, and -phenyl which is optionally substituted with halogen up to perhalo.

4) $R^6$ may be —CH=CH—$(C_6-C_{10})$aryl-$(R^{16})_s$ in which s represents 0 or an integer of 1–4, and $R^{16}$ represents a substituent selected from halogen, —$R^{3A}$, —$N(R^3)_2$, —$OR^{3A}$, —$SR^{3A}$, —$NO_2$, and —$CO_2R^3$.

5) $R^6$ may be —CH=CH-heteroaryl in which the heteroaryl ring contains 5–6 members and up to 3 heteroatoms selected from N, O, and S; and is optionally substituted with $R^{3A}$.

6) $R^6$ may be

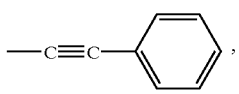

optionally substituted with halogen; —$R^{3A}$; —$N(R^3)_2$; —$OR^{3A}$; —$SR^{3A}$; —$NO_2$; —$CO_2R^3$; phenyl' which is in turn optionally substituted with halogen up to perhalo; and -heteroaryl of 5–6 members containing up to 3 heteroatoms selected from N, O, and S and optionally substituted with up to 2 substituents $R^{3A}$. The number of these substituents on the $R^6$ phenyl group is up to perhalo for halogen, and up to two for any combination of the —$R^{3A}$; —$N(R^3)_2$; —$OR^{3A}$; —$SR^{3A}$; —$NO_2$; —$CO_2R^3$; and phenyl' moieties.

7) $R^6$ may be —C≡C-heteroaryl in which the heteroaryl ring contains 5–6 members and up to 3 heteroatoms selected from N, O, and S, and is optionally substituted with up to 2 substituents $R^{3A}$.

8) $R^6$ may be —C≡C—$CH_2$—$R^{12}$.

9) $R^6$ may be phenyl which is optionally substituted with halogen up to perhalo, with the proviso that when this phenyl $R^6$ group is unsubstituted or bears a halogen substituent, then ring A also bears at least one substituent This phenyl $R^6$ substituent is also optionally substituted with up to 2 substituents selected from a) -phenyl' which is in turn optionally substituted with halogen, —$NHCOR^3$, —$N(R^3)_2$, —$OR^3$, or —$NO_2$, the number of these substituents being up to perhalo for halogen, and up to two for any combination of the —$NHCOR^3$, —$N(R^3)_2$, —$OR^3$, and —$NO_2$ moieties; and b) -heteroaryl of 5–6 members and containing up to 3 heteroatoms selected from N, O, and S.

10) $R^6$ may be

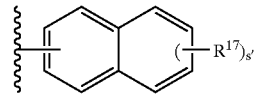

in which s' represents 0, 1, or 2; and $R^{17}$ represents halogen; $R^{3A}$; —$OR^3$; or —$N(R^3)_2$.

11) $R^6$ may be

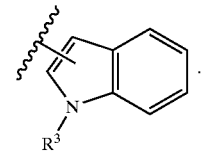

12) $R^6$ may be

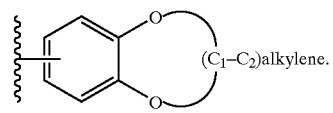

Furthermore, i) an aliphatic carbon atom attached to oxygen may not also bear a halogen substituent; ii) when any alkyl group is attached to O, S, or N, and bears a hydroxyl substituent, then the hydroxyl substituent is separated by at least two carbon atoms from the O, S, or N to which the alkyl group is attached; and iii) two alkyl groups located on the same N atom they may be linked by a bond, an O, an S, or $NR^3$ to form a N-containing heterocycle of 5–7 ring atoms. Pharmaceutically acceptable salts or N-oxides of these compounds are also included within the scope of the invention.

In a second embodiment, the invention relates to a compound of claim 1 wherein $R^4$ represents H, $R^6$ represents H, and Y represents an —O-phenyl moiety.

In a third embodiment, the invention relates to a compound of claim 1 wherein $R^4$ represents H and $R^6$ represents

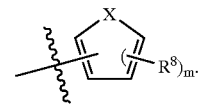

In a fourth embodiment, the invention relates to a compound of claim 1 wherein $R^4$ represents H and $R^6$ represents —$(C_1-C_4)$alkyl-$R^5$.

In a fifth embodiment, the invention relates to a compound of claim 1 wherein $R^4$ represents H and $R^6$ represents —CH=CH—$(C_6-C_{10})$aryl-$(R^{16})_S$.

In a sixth embodiment, the invention relates to a compound of claim 1 wherein $R^4$ represents H and $R^6$ represents —CH=CH-heteroaryl.

In a seventh embodiment, the invention relates to a compound of claim 1 wherein $R^4$ represents H and $R^6$ represents

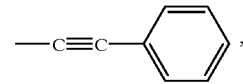

—C≡C-heteroaryl or —C≡C—$CH_2$—$R^{12}$.

In an eighth embodiment, the invention relates to a compound of claim 1 wherein $R^4$ represents H and $R^6$ represents optionally substituted phenyl.

In a ninth embodiment, the invention relates to a compound of claim 1 wherein $R^4$ represents H and $R^6$ represents

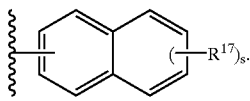

In a tenth embodiment, the invention relates to a compound of claim 1 wherein $R^4$ represents H and $R^6$ represents

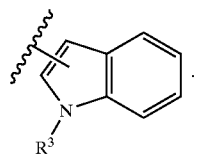

In an eleventh embodiment, the invention relates to a compound of claim 1 wherein $R^4$ represents H and $R^6$ represents

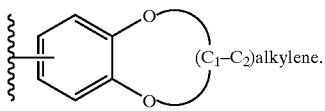

In a twelfth embodiment, the invention relates to a compound of claim 1 wherein $R^4$ represents a bond to the ortho position of ring A and $R^6$ represents

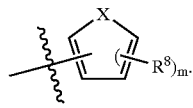

In a thirteenth embodiment, the invention relates to a compound of claim 1 wherein $R^4$ represents a bond to the ortho position of ring A and $R^6$ represents optionally substituted phenyl.

Pharmaceutically acceptable salts of the compounds of the invention as well as commonly used prodrugs of these compounds such as O-acyl derivatives of invention compounds which contain hydroxy groups are also within the scope of the invention.

The invention also relates to pharmaceutical compositions comprising one or more of the compounds of the invention, or their salts or prodrugs, in a pharmaceutically acceptable carrier.

The invention also relates to a method of treating a mammal such as a human having a condition related to 17β-HSDII activity, comprising administering to the mammal an amount of a compound of this invention, or a salt or prodrug thereof, which is effective to treat the condition. For purposes of the method of treatment, the compounds of the invention are as described above with respect to formula (I), but with the following modifications of their definition: a) in paragraph 2), the proviso requiring that when W is O and Y is OH, at least one of m and n is nonzero has been removed; b) in paragraph 9), when $R^6$ is phenyl, the proviso that when the phenyl group is unsubstituted or bears a halogen substituent, then ring A also bears at least one substituent has been deleted, and additional possible substituents on the phenyl moiety are —$R^{34}$; —$OR^3$; —$SR^3$; —$N(R^3)_2$; and —$CF_3$. Administration of compounds of this invention in combination with other pharmaceuticals used in treatment of the listed conditions is contemplated.

The conditions to be treated include osteoporosis, osteopenia, ovarian cancer, breast cancer, endometrial cancer, endometriosis, prostate cancer, acne, androgen-dependent hair loss, non-insulin-dependent diabetes mellitus, and hypercholesterolemia.

The disclosed compounds are also useful as diagnostic agents (e.g., in diagnostic kits or for use in clinical laboratories) for screening for the presence or activity of 17-βHSDII.

Definitions:

"Alkyl" stands for a hydrocarbon radical which may be linear, branched, or cyclic, with single or multiple branching. Examples of alkyl radicals are methyl; ethyl; n-propyl; isopropyl; n-butyl; sec-butyl; isobutyl; tert-butyl; n-pentyl; isopentyl; neopentyl; tert-pentyl; 2- or 3-methylpentyl; n-hexyl; isohexyl; cyclopropyl; cyclobutyl; cyclopentyl; cyclohexyl; methylcyclopropyl; 2- or 3-methylcyclobutyl; 2-, or 3-methylcyclopentyl; etc.

"Aryl" means an aromatic radical having 6 to 10 carbon atoms, such as phenyl and naphthyl.

Where the plural form is used for compounds, salts, and the like, this is taken to mean also a single compound, salt, or the like.

Where any group may carry multiple substituents and a variety of possible substituents is provided, the substituents are independently selected and need not be the same.

Any asymmetric carbon atoms may be present in the (R)-, (S)- or (R,S)configuration, preferably in the (R)- or (S)-configuration, whichever is most active. Substituents at a double bond or a ring may be present in cis- (=Z—) or trans (=E—) form.

The compounds of the present invention may contain asymmetric centers on the molecule, depending upon the nature of the various substituents. In certain instances, asymmetry may also be present due to restricted rotation about the central bond adjoining the two aromatic rings of the specified compounds. It is intended that all isomers (including enantiomers and diastereomers), either by nature of asymmetric centers or by restricted rotation as described above, as separated, pure or partially purified isomers or racemic mixtures thereof, be included within the ambit of the instant invention.

"Halogen" as employed herein stands for fluorine, chlorine, or bromine.

Salts are especially the pharmaceutically acceptable salts of compounds of formula I such as, for example, acid addition salts, preferably with organic or inorganic acids, from compounds of formula I with a basic nitrogen atom. Suitable inorganic acids are, for example, halogen acids such as hydrochloric acid, sulfuric acid, or phosphoric acid. Suitable organic acids are, for example, carboxylic, phosphonic, sulfonic, or sulfamic acids, for example acetic acid, propionic acid, octanoic acid, decanoic acid, dodecanoic acid, glycolic acid, lactic acid, hydroxybutyric acid, gluconic acid, glucosemonocarboxylic acid, fumaric acid, succinic acid, adipic acid, pimelic acid, suberic acid, azelaic acid, malic acid, tartaric acid, citric acid, glutaric acid, galactaric acid, amino acids, such as glutamic acid, aspartic acid, N-methylglycine, acetytaminoacetic acid, N-acetylasparagine or N-acetylcysteine, pyruvic acid, acetoacetic acid, phosphoserine, 2- or 3-glycerophosphoric acid. Compounds containing acidic substituents may also form salts with inorganic or organic bases.

"Heteroaryl" of 5 or 6 members denotes a 5- or 6-membered aromatic heterocycle containing 1–3 heteroatoms selected from O, S, and N, the number of N atoms being 0–3 and the number of O and S atoms each being 0–1. Examples of such radicals include

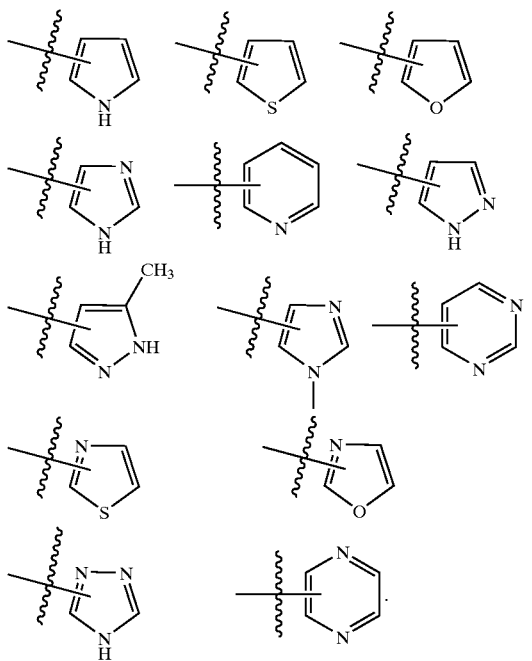

"Heterocyclyl" or "heterocycle" means a five- to seven-membered heterocyclic system with 1–3 heteroatoms selected from the group nitrogen, oxygen, and sulfur, which may be unsaturated or wholly or partly saturated, and is unsubstituted or substituted especially by lower alkyl, such as methyl, ethyl, 1-propyl, 2-propyl, or tert-butyl.

The statement is made that when two alkyl groups are found on a single N, they can be combined into a heterocycle of 5–7 atoms. Examples of such heterocycles, including the N to which they are attached, are:

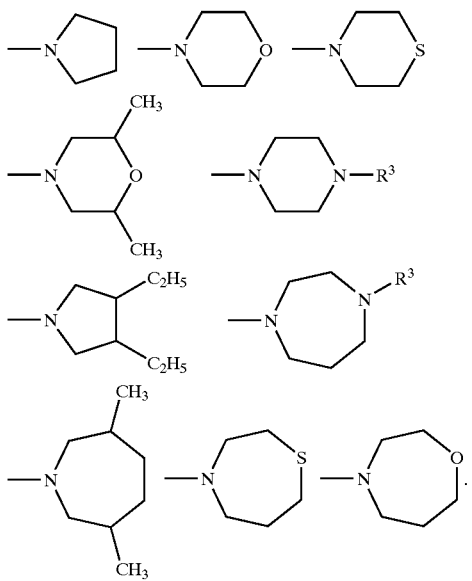

Halogenated lower alkyl, halogenated lower alkoxy and halogenated lower alkylthio are substituents in which the alkyl moieties are substituted either partially or in full with halogens, generally with chlorine and/or fluorine. Examples of such substituents are trifluoromethyl, trifluoromethoxy, trifluoromethylthio, dichloromethyl, fluoromethyl and difluoromethyl.

The method of the invention is primarily intended for treatment, in humans and other primates, of conditions involving steroids mediated by 17β-Hydroxysteroid Dehydrogenase-II.

The compounds may be administered orally, dermally, parenterally, by injection, by inhalation or spray, or sublingually, rectally or vaginally in dosage unit formulations. The term 'administered by injection' includes intravenous, intraarticular, intramuscular, subcutaneous and parenteral injections, as well as use of infusion techniques. Dermal administration may include topical application or transdermal administration. One or more compounds may be present in association with one or more non-toxic pharmaceutically acceptable carriers and if desired, other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations.

Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oil phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

Compounds of the invention may also be administered transdermally using methods known to those skilled in the art (see, for example: Chien; "Transdermal Controlled Systemic Medications"; Marcel Dekker, Inc.; 1987. Lipp et al. WO 94/04157 Mar. 3, 1994). For example, a solution or suspension of a compound of Formula I in a suitable volatile solvent optionally containing penetration enhancing agents can be combined with additional additives known to those skilled in the art, such as matrix materials and bacteriocides.

After sterilization, the resulting mixture can be formulated following known procedures into dosage forms. In addition, on treatment with emulsifying agents and water, a solution or suspension of a compound of Formula I may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures one or more materials selected from lower alcohols, lower ketones, lower carboxylic acid esters, polar ethers, lower hydrocarbons, halogenated hydrocarbons.

Suitable penetration enhancing materials for transdermal delivery systems are known to those skilled in the art, and include, for example, monohydroxy or polyhydroxy alcohols such as ethanol, propylene glycol or benzyl alcohol, saturated or unsaturated $C_8$–$C_{18}$ fatty alcohols such as lauryl alcohol or cetyl alcohol, saturated or unsaturated $C_8$–$C_{18}$ fatty acids such as stearic acid, saturated or unsaturated fatty esters with up to 24 carbons such as methyl, ethyl, propyl, isopropyl, n-butyl, sec-butyl isobutyl tert-butyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures one or more materials selected from monohydroxy or polyhydroxy alcohols, saturated or unsaturated $C_8$–$C_{18}$ fatty alcohols, saturated or unsaturated $C_8$–$C_{18}$ fatty acids, saturated or unsaturated fatty esters with up to 24 carbons, diesters of saturated or unsaturated dicarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrene-butadiene coploymers, and natural and synthetic rubbers. Cellulose ethers, derivatized polyethylenes, and silicates may also be used as matrix components. Additional additives, such as viscous resins or oils may be added to increase the viscosity of the matrix.

For all regimens of use disclosed herein for compounds of Formula I, the daily oral dosage regimen will generally be from 0.01 to 100 mg/Kg of total body weight. The daily dosage for administration by injection, including intravenous, intramuscular, subcutaneous and parenteral injections, and use of infusion techniques will generally be from 0.01 to 100 mg/Kg of total body weight. The daily rectal dosage regimen will generally be from 0.01 to 200 mg/Kg of total body weight. The daily vaginal dosage regimen will generally be from 0.01 to 100 mg/Kg of total body weight. The daily topical dosage regimen will generally be from 0.1 to 100 mg administered between one to four times daily. The transdermal concentration will generally be that required to maintain a daily dose of from 0.01 to 100 mg/Kg. The daily inhalation dosage regimen will generally be from 0.01 to 10 mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, but not limited to the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of a compound of Formula I or a pharmaceutically acceptable salt thereof given for a defined number of days, can be ascertained by those skilled in the art using conventional treatment tests.

Abbreviations and Acronyms

As employed herein, the following terms have the indicated meanings.

| Abbreviations and Acronyms As employed herein, the following terms have the indicated meanings. | |
|---|---|
| Ac$_2$O | acetic anhydride |
| anh. | anhydrous |
| AIBN | 2,2'-azobisisobutyronitrile |
| BOC | tert-butoxycarbonyl |
| n-BuLi | n-butyllithium |
| conc. | concentrated |
| mCPBA | 3-chloroperoxybenzoic acid |
| dec. | decomposition |
| DAST | (diethylamino)sulfur trifluoride |
| DIAD | diisopropyl azodicarboxylate |
| DMAP | 4-dimethylaminopyridine |
| DME | 1,2-dimethoxyethane |
| DMF | N,N-dimethylformamide |
| DMPU | 1,3-dimethyl-3,4,5,6-tetrahydro-2(1H)-pyrimidinone |
| DMSO | dimethylsulfoxide |
| DPPF | bis(diphenylphosphino)ferrocene |
| EDCI.HCl | 1-(3-dimethylaminopropyl)-3-ethylcarbodiimide hydrochloride |
| EtOAc | ethyl acetate |
| EtOH | ethanol (100%) |
| Et$_2$O | diethyl ether |
| Et$_3$N | triethylamine |
| KN(SiMe$_3$)$_2$ | potassium bis(trimethylsilyl)amide |
| KOtBu | potassium tert-butoxide |
| LiAlH$_4$ | lithium aluminum hydride |
| LiBH$_4$ | lithium borohydride |
| LiN(SiMe$_3$)$_2$ | lithium bis(trimethylsilyl)amide |
| MeOH | methanol |
| NMM | 4-methylmorpholine |
| Oxone ® | potassium peroxymonosulfate |
| PCC | pyridinium chlorochromate |
| Ph$_3$P | triphenylphosphine |
| PdCl$_2$(dppf) | [1,1'-bis(diphenylphosphino)ferrocene]dichloropalladium(II) |
| Pd(PPh$_3$)$_4$ | tetrakis(triphenylphosphine)palladium(0) |
| PivCl | trimethylacetyl chloride |
| TBAF | tetrabutylammonium fluoride |

| -continued | |
|---|---|
| Abbreviations and Acronyms As employed herein, the following terms have the indicated meanings. | |
| TBDMSCl | tert-butyldimethylsilyl chloride |
| TBDMSOTf | tert-butyldimethylsilyl triflate |
| THF | tetrahydrofuran |
| TFA | trifluoroacetic acid |
| TRIBAL | triisobutylaluminum |

General Preparative Methods

The compounds of the present invention may be prepared by use of known chemical reactions and procedures. Nevertheless, the following general preparative methods are presented to aid the reader in synthesizing the 17-beta-hydroxysteroid dehydrogenase-II inhibitors, with specific details provided below in the experimental section to illustrate working examples.

All variable groups of these methods are as described in the generic description if they are not specifically defined below.

It is recognized that compounds of the invention with each claimed optional functional group may not be prepared by each of the below-listed methods. Within the scope of each method, optional substituents may appear on reagents or intermediates which may act as protecting or otherwise non-participating groups. Utilizing methods well known to those skilled in the art, these groups are introduced and/or removed during the course of the synthetic schemes which provide the compounds of the present invention.

Certain formula I compounds in which Y is OH (Ia) may be prepared by reaction of an organolithium or Grignard reagent as shown in Flow Diagram I.

Flow Diagram I

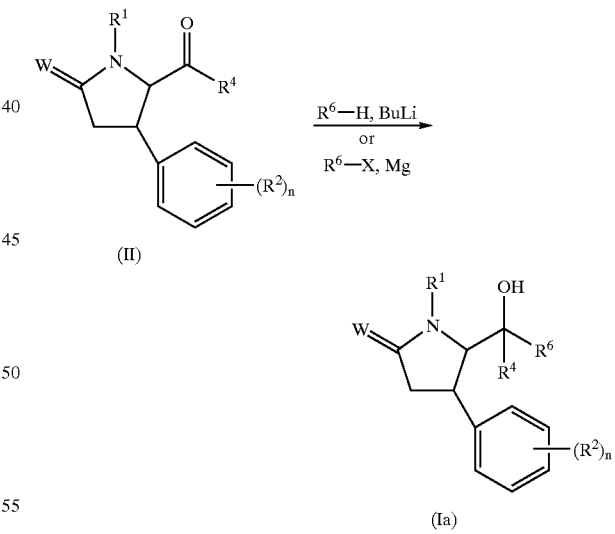

Such formula I compounds also provide the basis for preparation of related formula I compounds, as illustrated below in Flow Diagrams II–X.

For example, ether derivatives, III, may be prepared by straightforward alkylation of Ia with the appropriate alkyl halide (e.g., X=Br, I, or Cl) in the presence of base. Similarly, formula Ia compounds may be converted to compounds of formula IV by reaction with the appropriately substituted phenol under Mitsunobu conditions, or converted to compounds of formula V utilizing a standard fluorination procedure (Kuhlmeyer, et al., *Chem. Ber.* 1989, 122, 1729). Subjecting formula Ia compounds to standard acylation conditions also provides compounds of formula VI.

to a xanthate ester VII, may be accomplished by standard procedure (March, *Advanced Organic Chemistry*, 3rd ed., J. Wiley & Sons: New York, 1992, p. 893). Subsequent treatment with a palladium catalyst as described (Auburn, et al.

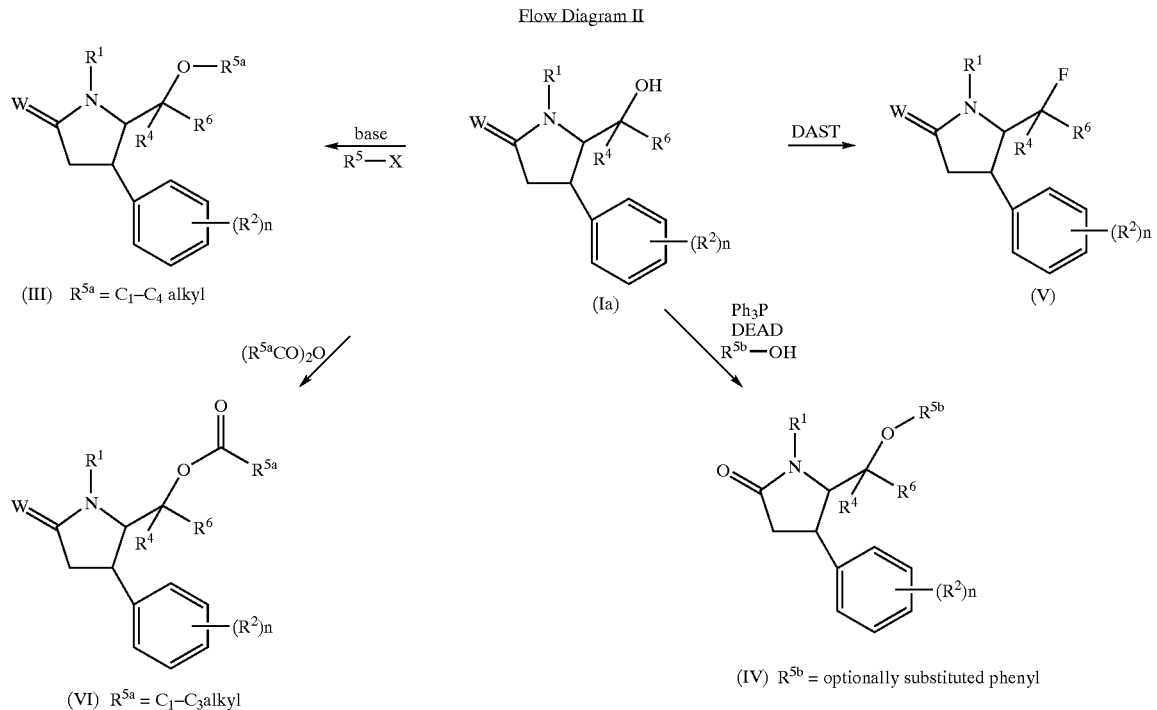

Certain formula Ib compounds in which $R^6$ is a phenyl- or heteroaryl-substituted alkyne (shown as 1b in Flow Diagram III) may be reduced to saturated alcohols, Ic (Eguchi, et al. *Tetrahedron*, 1993, 21, 4527), or to cis-allyl alcohols, Id (Sugai, et al. *Tetrahedron*, 1989, 45, 6135). The latter may be isomerized to the corresponding trans-allyl alcohols Ie with AIBN, using described methodology (Chatgilialoglu, et al. *J. Org. Chem.* 1995, 60, 3826).

*J. Chem. Soc. Chem. Commun.* 1986, 146) gives the compounds of formula If. Alternatively, treatment of formula VI compounds with (methylthio)trimethylsilane affords formula If compounds where $R^5=CH_3$ (Hasegawa, et al. *Carbohydr. Res.* 1992, 230, 257).

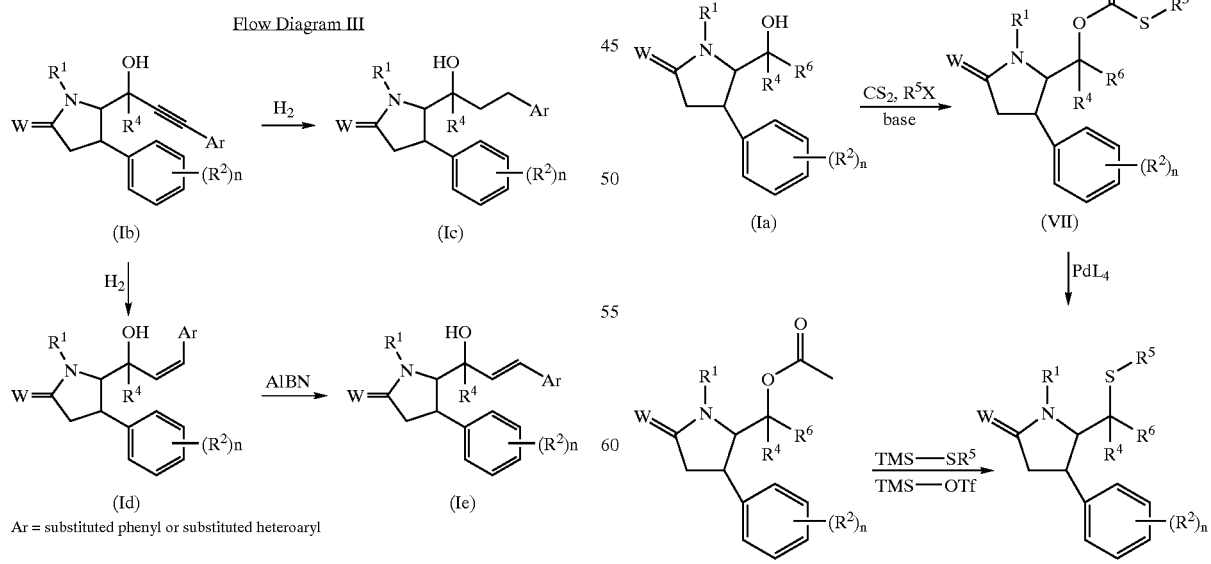

Formula I compounds in which Y is $SR^5$ may be prepared by the routes shown in Flow Diagram IV. Conversion of Ia Compounds of the present invention in which R⁴ forms a bond with the neighboring aromatic ring may be prepared as shown in Flow Diagram V by Friedel-Crafts reaction of formula VIII compounds (Carpino, et al. *J. Org. Chem.* 1990, 55, 247), followed by reaction with an appropriate organometallic compound to give X in a manner analogous to Flow Diagram I.

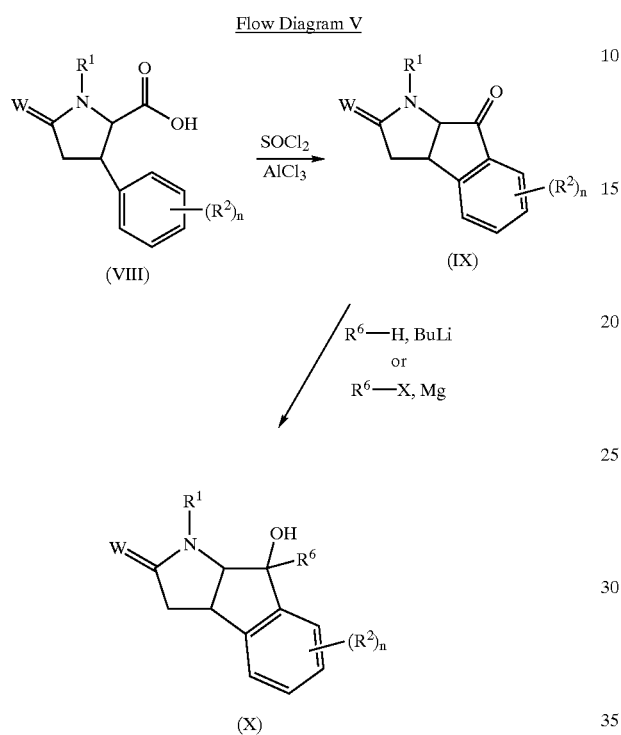

Compounds of formula I containing a suitable R² group may be further elaborated to other compounds of formula I with different R² groups using a variety of known chemical transformations. For example, when R² is —OTMS, it may be converted by hydrolysis to the corresponding compound where R² is OH, as shown in Flow Diagram VI.

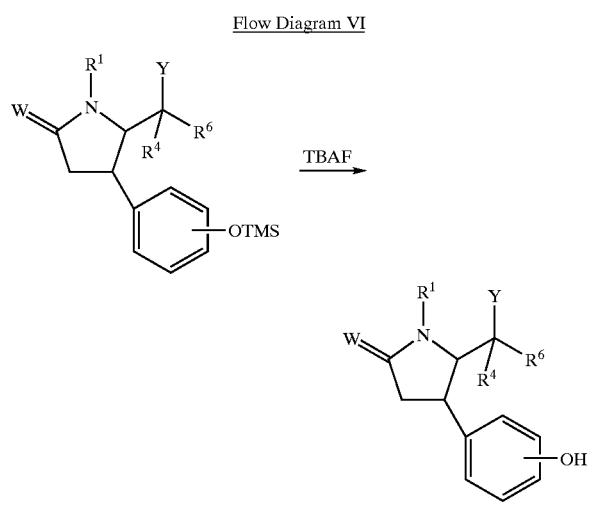

Similarly, formula I compounds in which R² is NO₂ may be first reduced to the NH₂ compound, then in subsequent steps, converted to the mono and dimethylamino compounds, as shown in Flow Diagram VII.

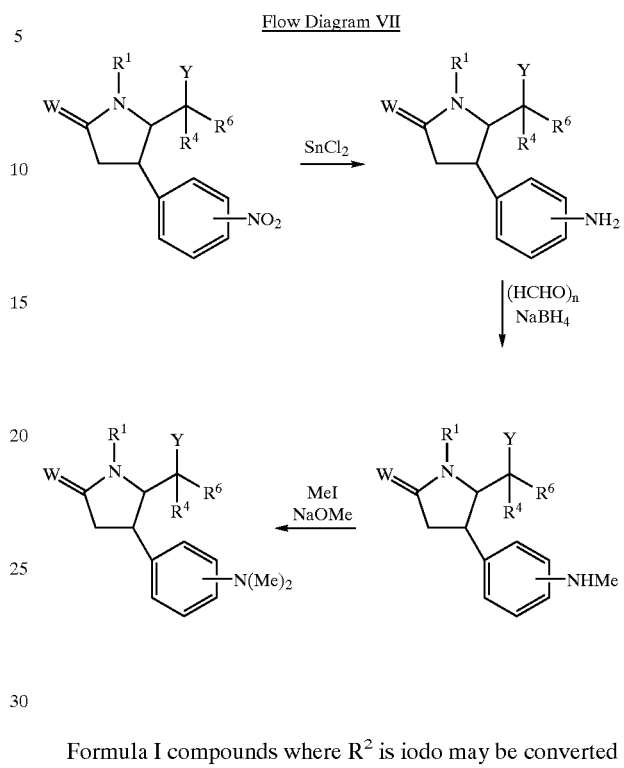

Formula I compounds where R² is iodo may be converted to a hydroxymethyl compound, or coupled with an aryl compound as shown in Flow Diagram VIII.

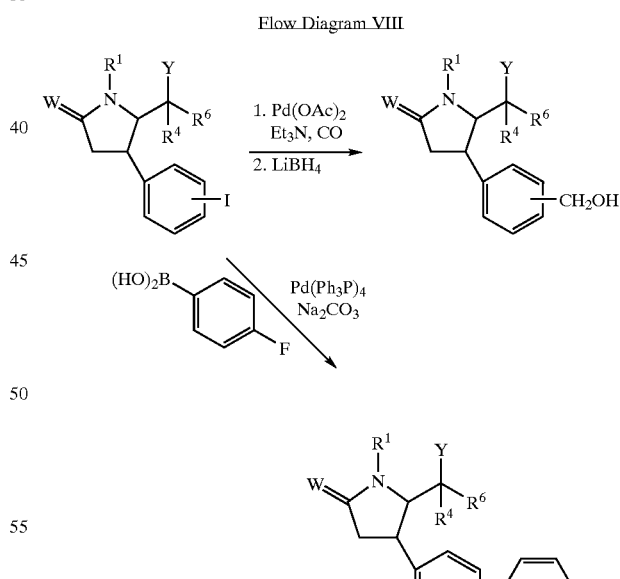

Certain other formula I compounds may be prepared by elaboration of other formula I compounds using a combination of halogenation and coupling reactions as shown in Flow Diagram IX. The phenyl ring in the boronic acid or aniline reagent may be optionally substituted.

Flow Diagram IX
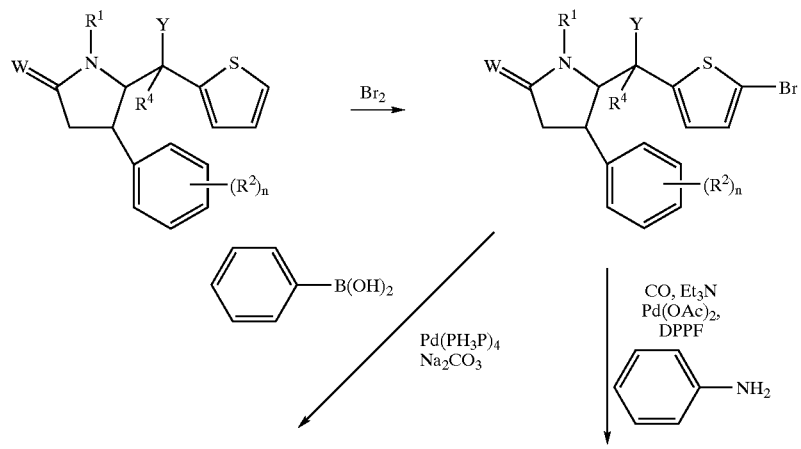
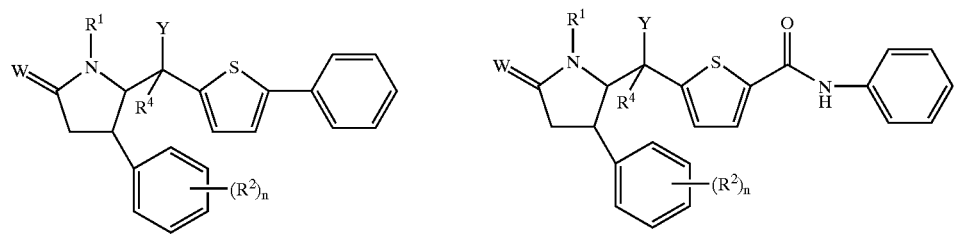
Other formula I compounds may be similarly prepared by manipulation of the substituents through standard deprotection or oxidation reactions as illustrated in Flow Diagram X.
Flow Diagram X
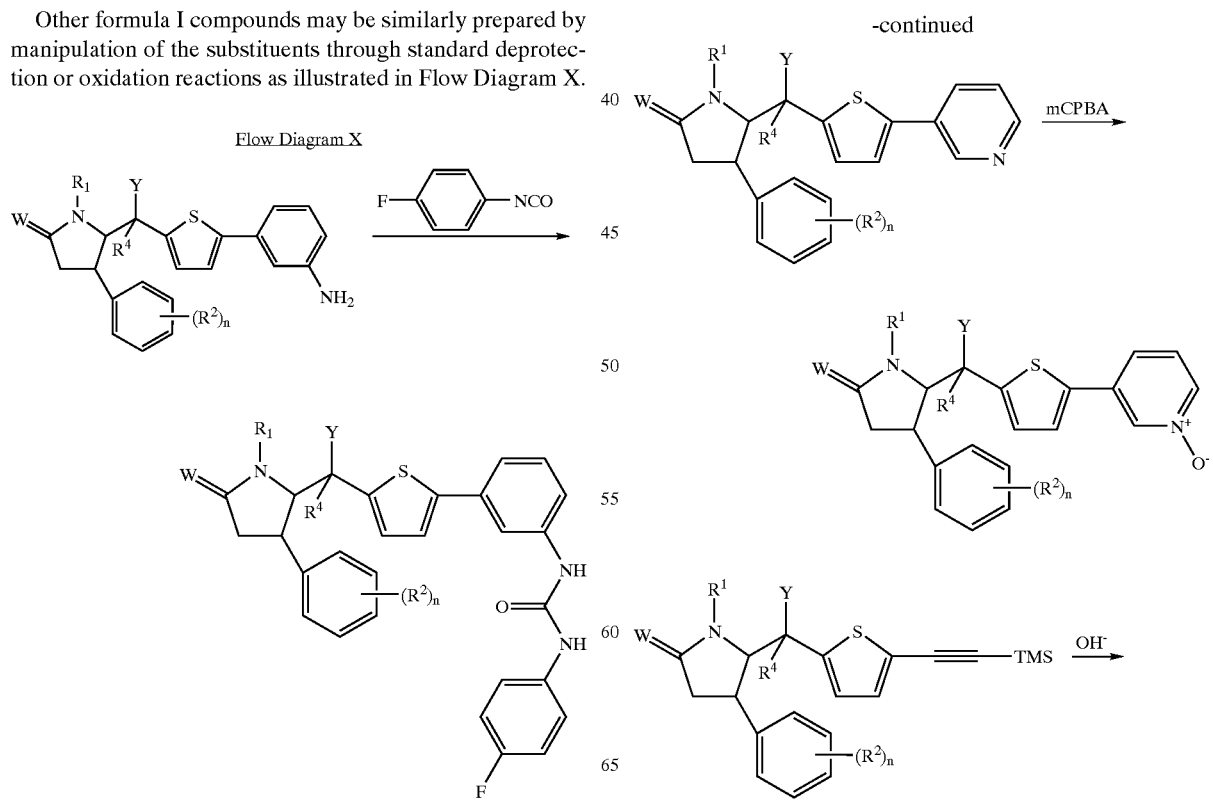

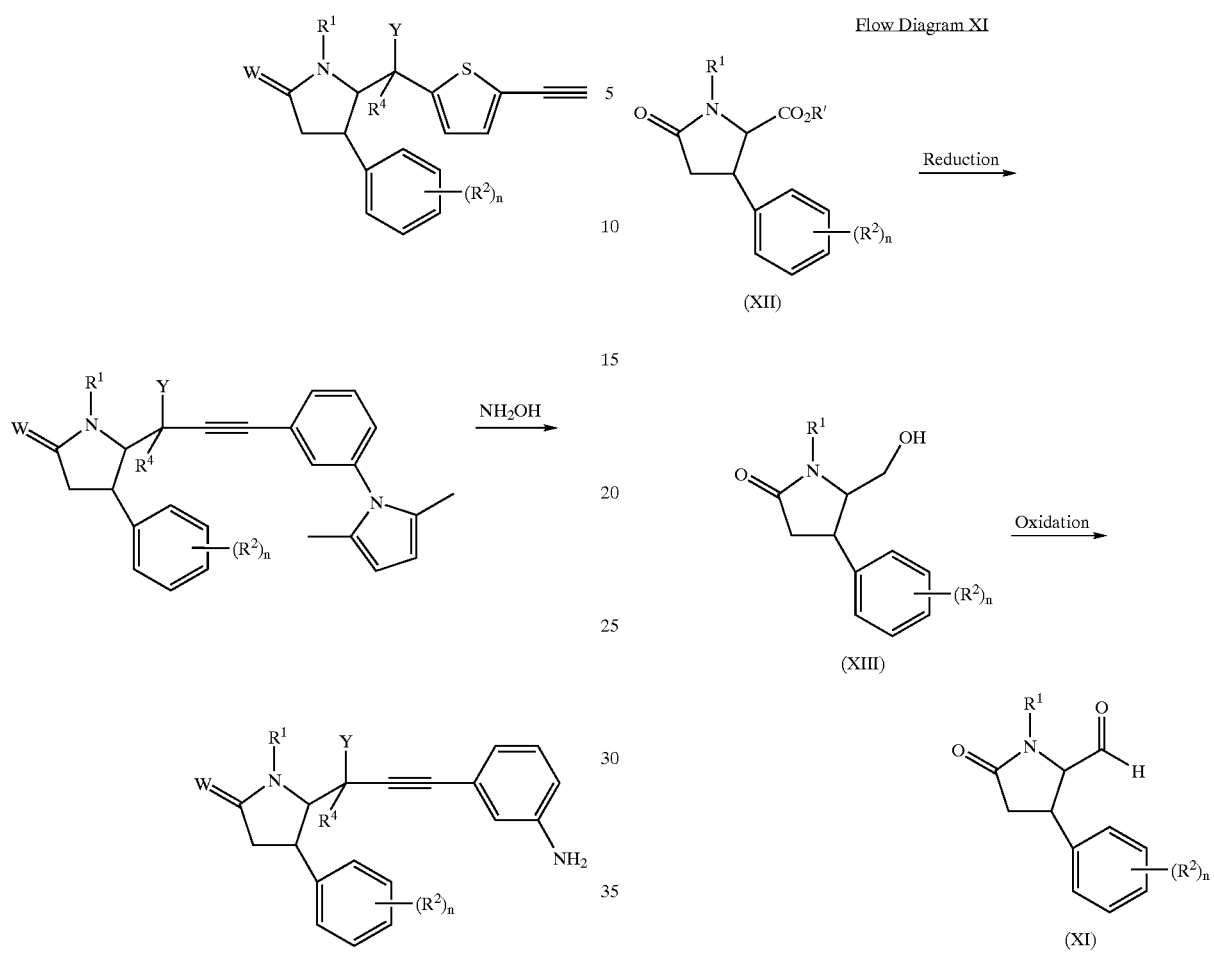

Flow Diagram XI

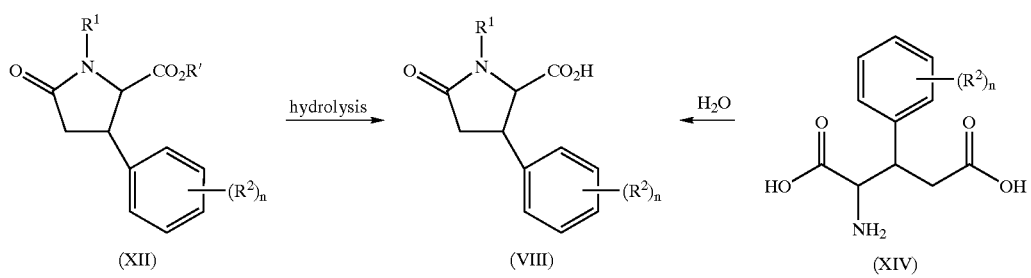

Flow Diagram XII

Intermediates of formula XI may be prepared from formula XII compounds (where R' is lower alkyl) by reduction, for example, with lithium borohydride, followed by oxidation, for example, under Dess-Martin conditions, as shown in Flow Diagram XI. The acid of formula VIII may be prepared from the formula XII compound by simple hydrolysis, or by direct cyclization (Harington, et al. *J. Biol. Chem.* 1925, 64, 31) from the diacid of formula XIV as shown in Flow Diagram XII.

Compounds of formula XII are accessible by a variety of methods. They may be prepared directly by catalytic hydrogenation of the corresponding pyrrolinones, XV (Herdeis, et al. *Tetrahedron: Asymmetry,* 1994, 5, 351), by reaction of alkoxycinnamates with alkyl acetamidomalonates (Pachaly, et al. *Arch. Pharm.* 1984, 317, 588), or by addition of aryl cuprates to the unsubstituted derivative XVa (Kozikowski, et al. *J. Amer. Chem. Soc.* 1998. 120. 6629), as shown in Flow Diagram XIII.

Flow Diagram XIII
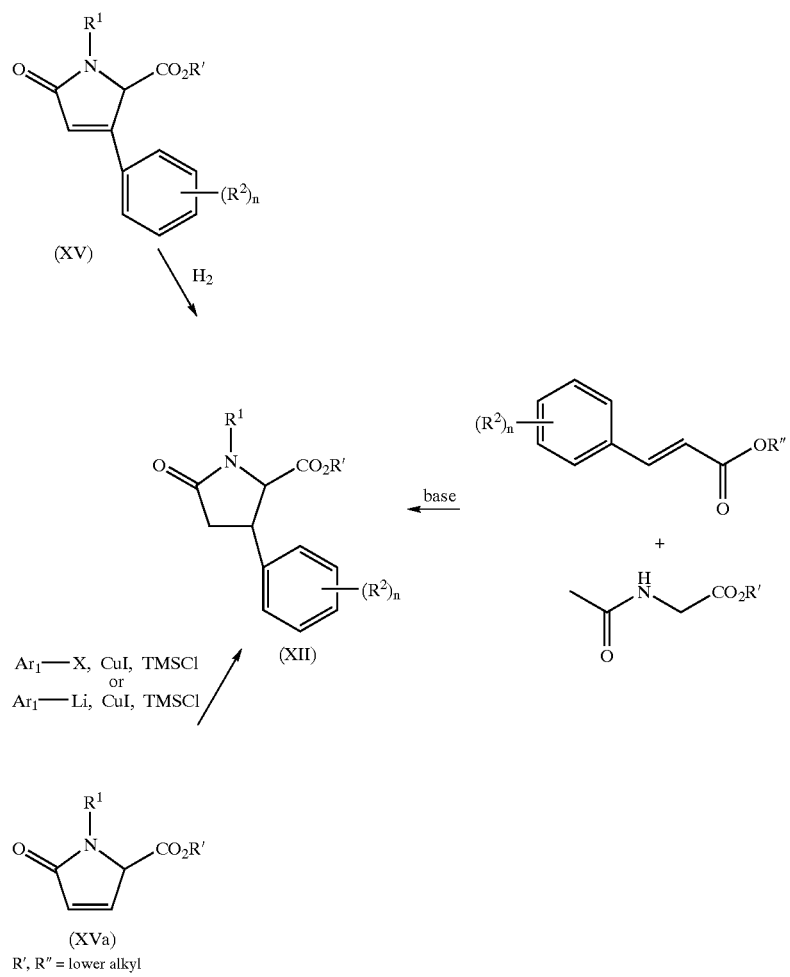
R', R'' = lower alkyl
Alternatively, a step-wise condensation/decarboxylation sequence may be used as shown in Flow Diagram XIV.
Flow Diagram XIV
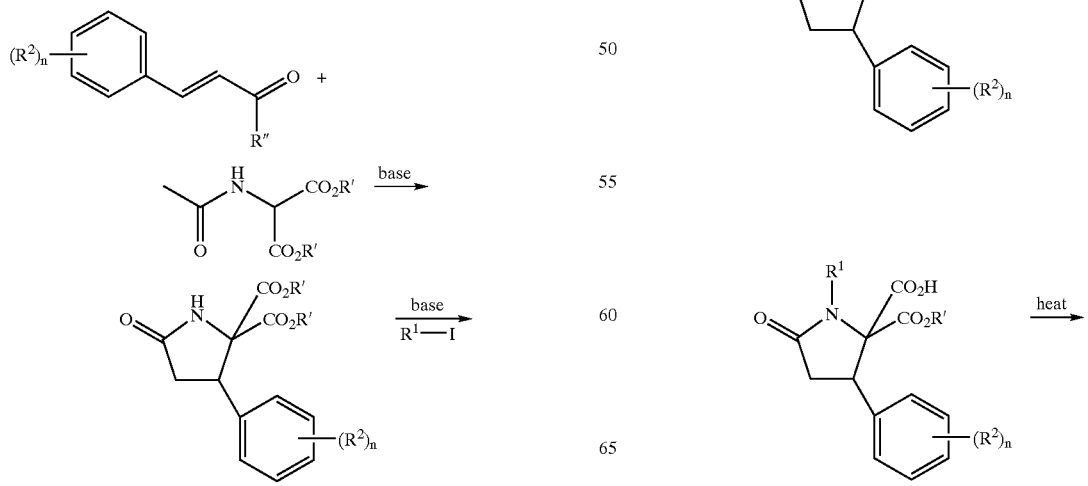

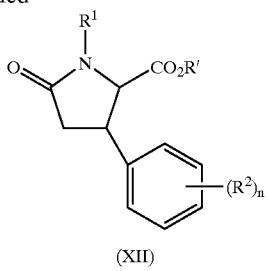

(XII)

R', R'' = lower alkyl

Preparation of individual stereoisomers XIIb and XIIc may be accomplished by a variation of the above reactions through the use of chiral auxiliary agents, as shown in Flow Diagram XV, and carried on to individual stereoisomers of formula I compounds. Alternatively, formula I stereoisomers may also be obtained by a chiral HPLC separation of the racemic primary alcohol XIII or the racemic final products.

Flow Diagram XV

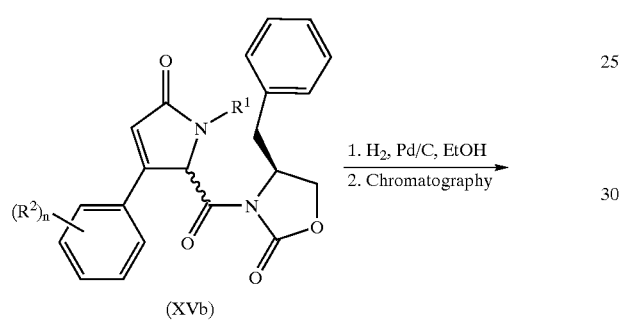

(XVb)

1. H$_2$, Pd/C, EtOH
2. Chromatography

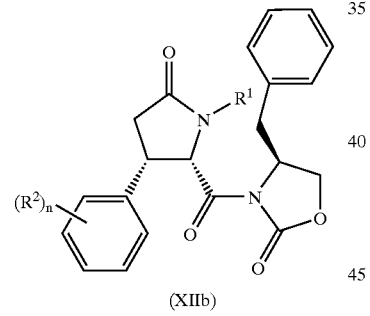

(XIIb)

+

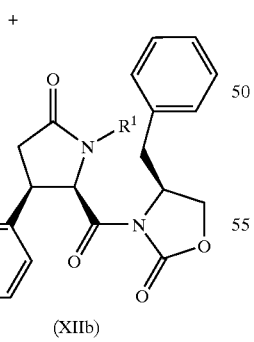

(XIIb)

Pyrrolinones formula XV may be prepared by cyclization of several different types of intermediates: alkynes, XVI or XVIa under basic conditions, (Rudorf and Schwarz, Z. Chem. 1988, 28, 101), halo diesters, XVII (Marquet, et al. Tetrahedron Lett. 1989, 30, 1799), and acids, XVIII in the presence of trifluoroacetic anhydride (Kruse, et al. Tetrahedron Lett. 1985, 41, 5241) as shown in Flow Diagram XVI.

Flow Diagram XVI

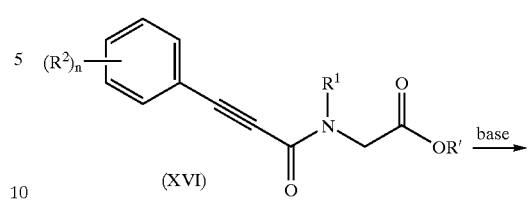

(XVI) base →

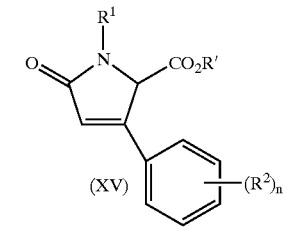

(XV)

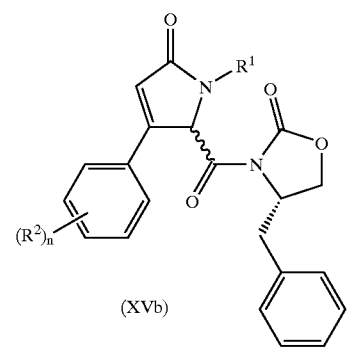

(XVIa) base →

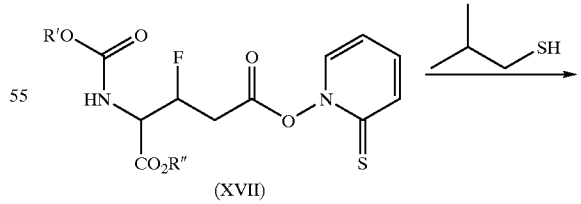

(XVII)

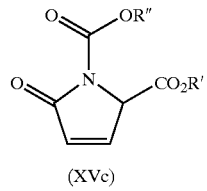

(XVc)

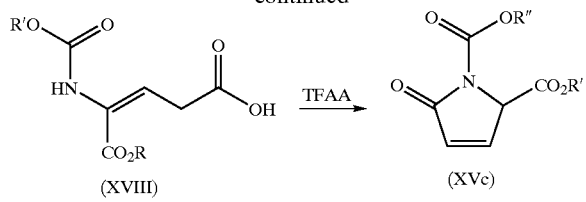

Experimental:

Examples of preparations of compounds of the invention are provided in the following detailed synthetic procedures. In the tables of compounds to follow, the synthesis of each compound is referenced back to these exemplary preparative steps.

All reactions were carried out under a positive pressure of dry argon or dry nitrogen, and were stirred magnetically unless otherwise indicated. Sensitive liquids and solutions were transferred via syringe or cannula, and introduced into reaction vessels through rubber septa. Commercial grade reagents and solvents were used without further purification.

Unless otherwise stated, the term 'concentration under reduced pressure' refers to use of a Buchi rotary evaporator at approximately 15 mm of Hg. Bulb-to-bulb concentrations were conducted using an Aldrich Kugelrohr apparatus, and in these cases temperatures refer to oven temperatures. All temperatures are reported uncorrected in degrees Celsius (° C.). Unless otherwise indicated, all parts and percentages are by volume.

Thin-layer chromatography (TLC) was performed on Whatman® pre-coated glass-backed silica gel 60A F-254 250 μm plates. Visualization of plates was effected by one or more of the following techniques: (a) ultraviolet illumination, (b) exposure to iodine vapor, (c) immersion of the plate in a 10% solution of phosphomolybdic acid in ethanol followed by heating, (d) immersion of the plate in a cerium sulfate solution followed by heating, and/or (e) immersion of the plate in an acidic ethanol solution of 2,4-dinitrophenylhydrazine followed by heating. Column chromatography (flash chromatography) was performed using 230–400 mesh EM Science® silica gel. Rotary chromatography was performed using pre-cast SiO$_2$ plates (Alltech®) and a Harrison Research Chromatotron.

Melting points (mp) were determined using a Thomas-Hoover melting point apparatus or a Mettler FP66 automated melting point apparatus and are uncorrected.

Fourier transform infrared spectra were obtained using a Mattson 4020 Galaxy Series spectrophotometer.

Proton ($^1$H) nuclear magnetic resonance (NMR) spectra were measured with a General Electric GN-Omega 300 (300 MHz) spectrometer with either Me$_4$Si (δ 0.00) or residual protonated solvent (CHCl$_3$ δ 7.26; MeOH δ 3.30; DMSO δ 2.49) as standard. Carbon ($^{13}$C) NMR spectra were measured with a General Electric GN-Omega 300 (75 MHz) spectrometer with solvent (CDCl$_3$ δ 77.0; d$_3$-MeOD; δ 49.0; d$_6$-DMSO δ 39.5) as standard.

Low resolution mass spectra (MS) and high resolution mass spectra (HRMS) were obtained as electron impact (EI), chemical ionization (CI), or as fast atom bombardment (FAB) mass spectra. Electron impact mass spectra (EI-MS) were obtained with a Hewlett Packard 5989A mass spectrometer equipped with a Vacumetrics Desorption Chemical Ionization Probe for sample introduction. The ion source was maintained at 250° C. Electron impact ionization was performed with electron energy of 70 eV and a trap current of 300 μA. Liquid-cesium secondary ion mass spectra (FAB-MS), an updated version of fast atom bombardment, were obtained using a Kratos Concept 1-H spectrometer. Chemical ionization mass spectra (CI-MS) were obtained using a Hewlett Packard MS-Engine (5989A) with methane or ammonia as the reagent gas (1×10$^{-4}$ torr to 2.5×10$^{-4}$ torr). The direct insertion desorption chemical ionization (DCI) probe (Vaccumetrics, Inc.) was ramped from 0–1.5 amps in 10 sec and held at 10 amps until all traces of the sample disappeared (~1–2 min). Spectra were scanned from 50–800 amu at 2 sec per scan. HPLC-electrospray mass spectra (HPLC ES-MS) were obtained using a Hewlett-Packard 1100 HPLC equipped with a quaternary pump, a variable wavelength detector, a C-18 column, and a Finnigan LCQ ion trap mass spectrometer with electrospray ionization. Spectra were scanned from 120–800 amu using a variable ion time according to the number of ions in the source. Gas chromatography—ion selective mass spectra (GC-MS) were obtained with a Hewlett Packard 5890 gas chromatograph equipped with an HP-1 methyl silicone column (0.33 mM coating; 25 m×0.2 mm) and a Hewlett Packard 5971 Mass Selective Detector (ionization energy 70 eV).

Elemental analyses were conducted by Robertson Microlit Labs, Madison N.J.

NMR spectra, LRMS, elemental analyses and HRMS of the compounds were consistent with the assigned structures.

The IUPAC names for chemical compounds were generated using ACD/Name Version 7.0 from Advanced Chemistry Development.

Chiral separation of enantiomers was accomplished using an HPLC apparatus selected from one of the following:

Separation A Apparatus

Shimadzu 10 Avp HPLC equipped with SPD-10Avp Photodiode array detector (UV range 200–300 nm) and 4.6×250 mm Chiracel AS 5μ column.

Separation B Apparatus

Rainin Dynamax HPLC equipped with UV-1 detector (254 nm) and a Chiralpak AS column (4.6×250 mm).

Separation C Apparatus

Rainin Dynamax HPLC equipped with UV-1 detector (254 nm) and a Chiralpak OJ column (4.6×250 mm).

Separation D Apparatus

Rainin Rampak HPLC equipped with UV-1 detector (254 nm) and a Chiracel AS column prepared as follows: Chiral Technologies Chiracel AS (1 kg, 10 micron, 100 Angstrom) bulk chiral stationary phase was placed in an Erlenmeyer flask. 1 L of HPLC grade i-PrOH was added, and the suspension sonicated for 1 hr. The resulting slurry was poured into a Dynamax Rampak axial compression column (2 in I.D.) and compressed to a pressure of 400 PSI.

INTERMEDIATES

Intermediate A

Preparation of Ethyl 2-[3-(2-fluorophenyl)-N-methylprop-2-ynoylamino]acetate

Step 1: Preparation of 3-(2-fluorophenyl)prop-2-yn-1-ol

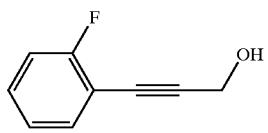

To a solution of 2-fluoro-iodobenzene (267 g, 1.2 mol) in Et$_3$N (6L) was added propargyl alcohol (140 g, 2.5 mol, 2 equiv), followed by PdCl$_2$(dppf) (6.1 g, 8.8 mmol, 0.007 equiv), Ph$_3$P (12.5 g, 47.6 mmol, 0.038 equiv) and copper(I)

iodide (12.6 g, 66.3 mmol, 0.053 equiv). The resulting mixture was heated at the reflux temperature for 17 h, allowed to cool to room temperature and filtered through a pad of Celite®. The filtrate was concentrated under reduced pressure and purified by vacuum distillation to give 3-(2-fluorophenyl)prop-2-yn-1-ol (156.6 g, 87%) as a deep brown oil: bp 84° C./0.3 mmHg; TLC (CH$_2$Cl$_2$) R$_f$ 0.44; $^1$H NMR (CDCl$_3$) δ 2.46 (d, J=5.0 Hz, 1H), 4.45 (d, J=5.0 Hz, 1H), 6.94–7.02 (m, 2H), 7.17–7.23 (m, 1H), 7.31–7.37 (m, 1H); GCMS m/z (rel abundance) 151 (MH$^+$, 75%).

Step 2: Preparation of 3-(2-fluorophenyl)prop-2-ynal

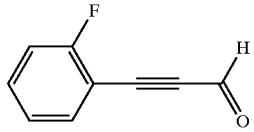

To a solution of oxalyl chloride (102 mL, 1.18 mol, 1.2 equiv) in CH$_2$Cl$_2$ (3L) at −78° C. was slowly added DMSO (167 mL, 2.35 mol, 2.4 equiv) while keeping the reaction temperature below −59° C. The mixture was stirred for 10 min and treated with a solution of 3-(2-fluorophenyl)prop-2-yn-1-ol (147 g, 0.98 mol) in CH$_2$Cl$_2$ (100 mL), keeping the reaction temperature below −65° C. The resulting thick white slurry was stirred for 15 min, then treated with Et$_3$N (682 mL, 4.90 mol, 5 equiv). After 10 min the reaction mixture was allowed to warm to 0° C. and treated with water (2 L). The organic layer was washed with water (3×1L), dried (Na$_2$SO$_4$) and concentrated under reduced pressure to afford 3-(2-fluorophenyl)prop-2-ynal (148 g, 100%) as a brown oil which was stored suspended in frozen benzene (0.5 L): $^1$H NMR (CDCl$_3$) δ 7.03–7.14 (m, 2H), 7.37–7.52 (m, 2H), 9.36 (s, 1H); $^{13}$C NMR (CDCl$_3$) δ 88.1, 92.4 (d, J$_{C-F}$=2.4 Hz, 1C), 108.2 (d, J$_{C-F}$=14.5 Hz, 1C), 115.9 (d, J$_{C-F}$=19.6 Hz, 1C), 124.4 (d, J$_{C-F}$=3.6 Hz, 1C), 133.3 (d, J$_{C-F}$=8.5 Hz, 1C), 134.8 162.6 (d, J$_{C-F}$=246.3 Hz, 1C), 176.4; GCMS m/z (rel abundance) 149 (MH$^+$, 75%).

Step 3: Preparation of 3-(2-fluorophenyl)prop-2-ynoic acid

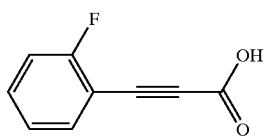

A mixture of NaH$_2$PO$_4$ (37 g, 0.3 mol, 0.3 equiv) in water (330 mL) buffered to pH 2 with conc. HCl and H$_2$O$_2$ (30%, 112 mL, 1.1 mol, 1.1 equiv) was added to a solution of 3-(2-fluorophenyl)prop-2-ynal (151 g, 1.02 mol) in CH$_3$CN (830 mL). The resulting mixture was cooled in an ice bath and was treated slowly with a solution of NaClO$_2$ (102 g, 1.1 mol, 1.1 equiv) in water (1.1 L), keeping the temperature below 10° C. After 30 min a solution of NaClO$_2$ (5.8 g, 64 mmol, 0.06 equiv) in water (50 mL) was added. After another 30 min the layers were separated and the aqueous layer was washed with EtOAc (3×500 mL). The organic layers were combined and back-extracted with a saturated NaHCO$_3$ solution (3×500 mL). The aqueous layers were combined, acidified to pH 1 with conc. HCl and extracted with EtOAc (3×500 mL). The combined organic layers were washed with a saturated NaCl solution (1 L), dried (Na$_2$SO$_4$) and concentrated under reduced pressure to give 3-(2-fluorophenyl)prop-2-ynoic acid (144 g, 86%) as a yellow solid: TLC (1% AcOH/CH$_2$Cl$_2$) R$_f$ 0.34; $^1$H NMR (CDCl$_3$+ d$_4$-MeOH) δ 6.98–7.08 (m, 2H), 7.29–7.48 (m, 2H), 12.77 (br s, 1H); $^{13}$C NMR (CDCl$_3$+d$_4$-MeOH) δ 78.3, 85.7 (d, J$_{C-F}$=2.5 Hz, 1C), 108.3 (d, J$_{C-F}$=15.8 Hz, 1C), 115.4 (d, J$_{C-F}$=20.7 Hz, 1C), 124.0, 132.1 (d, J$_{C-F}$=7.3 Hz, 1C), 134.1 (d, J$_{C-F}$=9.8 Hz, 1C), 135.2, 154.8, 163.1 (d, J$_{C-F}$=256.1 Hz, 1C).

Step 4: Preparation of Ethyl 2-[3-(2-fluorophenyl)-N-methylprop-2-ynoylamino]acetate

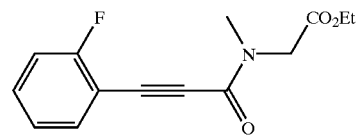

To a 0° C. slurry of 3-(2-fluorophenyl)prop-2-ynoic acid (151 g, 0.92 mol) in CH$_2$Cl$_2$ (3L) was added DMAP (118 g, 0.96 mol, 1.05 equiv), followed by sarcosine ethyl ester hydrochloride (148 g, 0.96 mol, 1.05 equiv), and NMM (233 g, 2.3 mol, 2.5 equiv). The resulting clear solution was allowed to warm to room temperature and was maintained for 17 h. The reaction mixture was washed with a 2N HCl solution (4×500 mL). The aqueous layers were combined and the mixture was adjusted to pH 2 using conc. H$_2$SO$_4$, then back-extracted with CH$_2$Cl$_2$ (2×500 mL). The organic layers were combined, washed with a 10% H$_2$SO$_4$ solution (2×500 mL), dried (Na$_2$SO$_4$) and concentrated under reduced pressure to give ethyl 2-[3-(2-fluorophenyl)-N-methylprop-2-ynoylamino]acetate (174 g, 72%) as a brown oil: TLC (40% EtOAc/hex) R$_f$ 0.61; $^1$H NMR (CDCl$_3$; of rotomeric mixture) δ 1.27 (t, J=7.2 Hz, 3H), 3.07 (s, 1.4H, N—CH$_3$), 3.36 (s, 1.6H, N—CH$_3$), 4.17–4.27 (m, 3.2H), 4.41 (s, 0.8H, N—CH$_2$), 7.06–7.17 (m, 2H), 7.37–7.58 (m, 2H); $^{13}$C NMR (CDCl$_3$; of rotomeric mixture) δ 14.00, 14.03, 33.5, 37.2, 48.0, 52.5, 61.3, 61.5, 83.6, 84.3, 85.7 (d, J$_{C-F}$=9.9 Hz, 1C), 108.9 (d, J$_{C-F}$=15.5 Hz, 1C), 109.1, (d, J$_{C-F}$=15.5 Hz, 1C), 115. (d, J$_{C-F}$=10.4 Hz, 1C), 115.6 (d, J$_{C-F}$=10.4 Hz, 1C), 124.2, 132.0 (d, J$_{C-F}$=7.8 Hz, 1C), 132.1 (d, J$_{C-F}$=7.8 Hz, 1C), 134.10, 134.15, 154.6, 163.3 (d, J$_{C-F}$=254.4 Hz, 1C), 168.1, 168.5; HPLC ES-MS m/z (rel abundance) 264 (MH$^+$, 75%).

Intermediate B

Preparation of Ethyl 2-[3-(3-fluorophenyl)-N-methylprop-2-ynoylamino]acetate

Step 1: Preparation of Ethyl 2-(3-trimethylsilyl-N-methylprop-2-ynoylamino)acetate

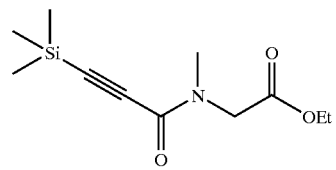

To a solution of sarcosine ethyl ester hydrochloride (5.28 g, 34.5 mmol), 3-trimethylsilylpropynoic acid (4.90 g, 35.5 mmol), NMM (4.17 mL, 38 mmol) and DMAP (5.05 g, 41.4 mmol) in CH$_2$Cl$_2$ (100 mL) was added EDCI.HCl (8.61 g, 44.8 mmol) in one portion. The reaction was stirred for 18 h, then diluted with CH$_2$Cl$_2$ (200 mL). The resulting solution was washed with water (2×100 mL), a 1N HCl solution (2×50 mL), and a saturated NaCl solution (100 mL). The organic layer was dried (MgSO$_4$) and concentrated under reduced pressure. The crude orange oil was purified by flash chromatography (40% EtOAc/hex) to give ethyl 2-(3- trimethylsilyl-N-methylprop-2-ynoylamino) acetate (6.52 g, 78%) as a clear oil: TLC (50% EtOAc/hex) $R_f$ 0.71; HPLC ES-MS m/z (rel abundance) 242 (MH$^+$, 100%).

Step 2: Preparation of Ethyl 2-[3-(3-fluorophenyl)-N-methylprop-2-ynoylamino]acetate

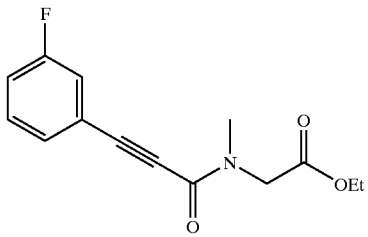

To a solution of ethyl 2-(3-trimethylsilyl-N-methylprop-2-ynoylamino) acetate (1.13 g, 4.69 mmol) in THF (15 mL) was added 1-fluoro-3-iodobenzene (0.6 mL, 5.00 mmol), followed by palladium(II) acetate (51 mg, 0.24 mmol) and Ph3P (245 mg, 0.938 mmol). After stirring for 5 minutes, copper(I) iodide (44 mg, 0.24 mmol) was added, followed by triethylamine (1.96 mL, 14.1 mmol). The reaction mixture was stirred for 5 d and treated with a 1N HCl solution. The resulting mixture was extracted with EtOAc, dried (MgSO$_4$) and concentrated under reduced pressure. The crude product was purified by flash chromatography to give ethyl 2-[3-(3-fluorophenyl)-N-methylprop-2-ynoylamino] acetate (750 mg, 61%) as an orange oil: TLC (50% EtOAc/hex) $R_f$ 0.56; HPLC ES-MS m/z (rel abundance) 264 (MH$^+$, 100%).

Intermediate C

Preparation of Ethyl 2-[3-(3-methoxyphenyl)-N-methylprop-2-ynoylamino]acetate

Step 1: Preparation of Ethyl 2-(3-trimethylsilyl-N-methylprop-2-ynoylamino)acetate

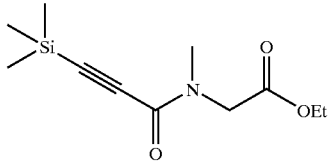

Ethyl 2-(3-trimethylsilyl-N-methylprop-2-ynoylamino) acetate was prepared as described in the procedure for Intermediate B, step 1.

Step 2: Preparation of Ethyl 2-(N-methylprop-2-ynoylamino)acetate

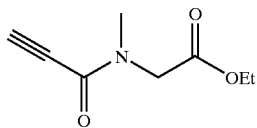

To a solution of ethyl 2-(3-trimethylsilyl-N-methylprop-2-ynoylamino)acetate (5.28 g, 21.9 mmol) in THF (80 mL) was added dropwise a solution of TBAF (1M in THF, 24.0 mL, 24.0 mmol). After stirring for 10 min, a saturated NH$_4$Cl solution (150 mL) was added and the resulting mixture was extracted with EtOAc (3×100 mL). The organic layer was washed with a saturated NaCl solution (400 mL), dried (Na$_2$SO$_4$) and concentrated under reduced pressure.

The crude product was purified by flash chromatography (50% EtOAc/hex) to give ethyl 2-(N-methylprop-2-ynoylamino)acetate (1.9 g, 51%) as a yellow oil: TLC (50% EtOAc/hex) $R_f$ 0.50; $^1$H NMR (CDCl$_3$; a mixture of two rotomers) δ 1.26–1.33 (m, 3H), 3.03 (s, 1.2H), 3.29 (s, 1.8H), 3.09 (s, 0.43H), 3.17 (s, 0.57H), 4.16 (s, 1.1H), 4.33 (s, 0.9H), 4.17–4.28 (m, 2H).

Step 3: Preparation of Ethyl 2-[3-(3-methoxyphenyl)-N-methylprop-2-ynoylamino]acetate

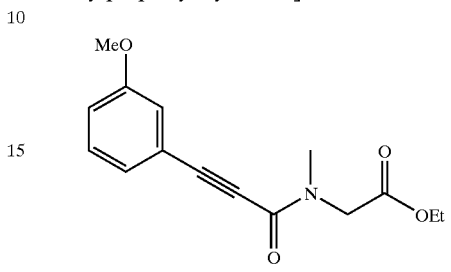

To a solution of ethyl 2-(N-methylprop-2-ynoylamino) acetate (312 mg, 1.84 mmol) in THF (6 mL) was added 3-iodoanisole (475 mg, 0.24 mL, 2.03 mmol), dichlorobis (triphenylphosphine)palladium(II) (133 mg, 0.19 mmol), copper(I) iodide (36 mg, 0.19 mmol) and Et$_3$N (279 mg, 0.39 mL, 2.76 mmol). The resulting mixture was stirred in dark for 2 h. A saturated NH$_4$Cl solution (30 mL) was then added and the mixture was extracted with EtOAc (2×30 mL). The combined organic layers were washed with a saturated NaCl solution (60 mL), dried (Na$_2$SO$_4$) and concentrated under reduced pressure to give a dark oil, which was dissolved in EtOAc and filtered through a pad of silica gel. The filtrate was concentrated under reduced pressure and the residue was purified by flash chromatography (33% EtOAc/hex) to give ethyl 2-[3-(3-methoxyphenyl)-N-methylprop-2-ynoylamino]acetate (175 mg, 35%) as a light yellow oil: $^1$H NMR (CDCl$_3$; a mixture of two rotomers) δ 1.30 (t, J=7.0 Hz, 3H), 3.10 (1.35H), 3.36 (s, 1.65H), 3.81 (s, 1.35H), 3.82 (s, 1.65H), 4.20–4.30 (m, 3.2H), 4.39 (s, 0.8H), 6.97–7.29 (m, 4H); HPLC ES-MS m/z (rel abundance) 276 (MH$^+$, 100%).

Intermediate D

Preparation of Ethyl 2-[3-(2-fluorophenyl)-N-methylprop-2-ynoylamino]acetate

Step 1: Preparation of 3-(2-fluorophenyl)prop-2-ynoic acid

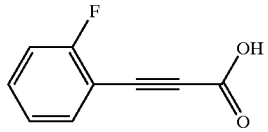

To a −78° C. solution of 1-ethynyl-2-fluorobenzene (0.94 g, 7.83 mmol) in anhyd. THF (25 mL) was added dropwise a solution of n-BuLi (1.6M in hexanes, 5.14 mL, 8.22 mmol). The solution was stirred for 10 min, then ethyl chloroformate (2.24 mL, 23.5 mmol) was added and the reaction mixture was allowed to warm to room temperature. The resulting mixture was poured onto ice water (200 mL) and extracted with Et$_2$O. The organic layer was dried (MgSO$_4$) and concentrated under reduced pressure to give ethyl 3-(2-fluorophenyl)prop-2-ynoate (1.68 g) as a yellow oil. The crude product was dissolved in MeOH (10 mL) and was added to a 5° C. mixture of a 1N NaOH solution (12.5 mL) and MeOH (30 mL). The reaction mixture was allowed to warm to room temperature, stirred for 1 h, treated with a 1N HCl solution (15 mL) and a saturated NaCl solution (20 mL). The resulting mixture was extracted with EtOAc, dried (MgSO$_4$) and concentrated under reduced pressure to give 3-(2-fluorophenyl)prop-2-ynoic acid (1.22 g, 95% for two steps) as a tan solid: TLC (100% EtOAc) R$_f$ 0.18; $^1$H NMR (acetone-d$_6$) δ 7.30 (m, 2H), 7.60 (m, 2H), 12.0 (s, 1H).

Step 2: Preparation of Ethyl 2-[3-(2-fluorophenyl)-N-methylprop-2-ynoylamino]acetate

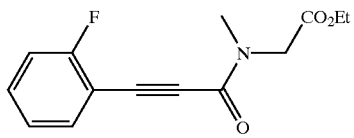

To a solution of sarcosine ethyl ester hydrochloride (1.14 g, 7.44 mmol) and 3-(2-fluorophenyl)prop-2-ynoic acid (1.22 g, 7.44 mmol) in anhyd. CH$_2$Cl$_2$ was added NMM (10 mL, 8.93 mmol), followed by EDCI.HCl (1.86 g, 9.67 mmol) and DMAP (0.99 g, 8.2 mmol). The reaction mixture was stirred for 5 h at room temperature and diluted with CH$_2$Cl$_2$. The resulting solution was washed with a 0.5N HCl solution (2×25 mL), a 0.5N NaOH solution (2×25 mL) and a saturated NaCl solution. The organic layer was dried (MgSO$_4$), concentrated onto silica gel under reduced pressure and purified by flash chromatography (30% EtOAc/hex) to yield ethyl 2-[3-(2-fluorophenyl)-N-methylprop-2-ynoylamino]acetate (1.50 g, 77%) as a yellow oil: TLC (50% EtOAc/hex) R$_f$ 0.54; HPLC ES-MS m/z (rel abundance) 264 (100%).

Intermediate E: Preparation of 2-(4-fluorophenylthio)thiophene

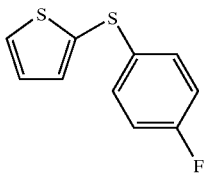

To a degassed mixture of 2-iodothiophene (0.87 mL, 7.88 mmol), Cu$_2$O (0.56 g, 3.9 mmol) and KOH (0.44 g, 7.8 mmol) in DMF (7.8 mL) was slowly added 4-fluorobenzenethiol (0.33 mL, 7.8 mmol). The resulting mixture was heated at 135° C. for 15 h, allowed to cool to room temperature and poured into a 0° C. 6N HCl solution. After 15 min. the precipitate was filtered and washed with benzene. The filtrate was extracted with benzene, dried (MgSO$_4$) and concentrated under reduced pressure to give 2-(4-fluorophenylthio)thiophene (1.13 g, 69%) as a pale yellow oil: TLC (10% EtOAc/hex) R$_f$ 0.49; HPLC ES-MS m/z (rel intensity) 210 (M$^+$, 100).

Intermediate F

Preparation of 4-chloro-1-(2-thienylsulfonyl)benzene

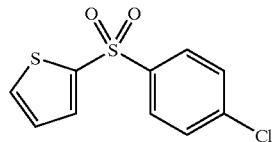

To a 0° C. solution of 2-(4-chlorophenylthio)thiophene (0.49 g, 2.2 mmol) in MeOH (8 mL) was added a solution of Oxone® 3.98 g, 6.5 mmol) in water (8 mL). The resulting slurry was allowed to warm to room temperature, stirred for 4 h, then diluted with water and extracted with CH$_2$Cl$_2$. The organic layer was washed with water and a saturated NaCl solution, dried (Na$_2$SO$_4$) and concentrated under reduced pressure to give 4-chloro-1-(2-thienylsulfonyl)benzene (0.69 g, 100%) as a white solid: TLC (20% EtOAc/hex) R$_f$ 0.36; $^1$H NMR (CDCl$_3$) δ 7.09–7.12 (m, 1H), 7.47–7.52 (m, 2H), 7.66–7.71 (m, 2H), 7.90–7.95 (m, 2H).

Intermediate G

Preparation of 2-[(4-fluorophenyl)sulfonyl]thiophene

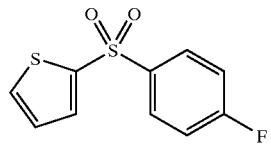

To a solution of 2-(4-fluorophenylthio)thiophene (1.09 g, 5.18 mmol) in acetic acid (14.3 mL) was added a 30% aqueous solution of H$_2$O$_2$ (1.30 mL). The reaction mixture was heated at 100° C. for 45 min, then was treated with water. The resulting suspension was extracted with CH$_2$Cl$_2$. The combined organic layers were washed with a saturated NaHCO$_3$ solution, dried (MgSO$_4$) and concentrated under reduced pressure to yield 2-[(4-fluorophenyl)sulfonyl]thiophene (0.79 g, 63%) as a white solid: TLC (hex) R$_f$ 0.08; $^1$H NMR (CDCl$_3$) δ 7.09–7.27 (m, 3H), 7.67–7.71 (m, 2H), 7.99–8.04 (m, 2H).

Intermediate H

Preparation of 2-(2-thienyl)-1-(trimethylsilyl)acetylene

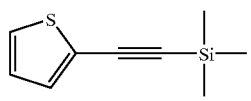

To a mixture of piperidine (10 mL, 93.9 mmol), 2-bromothiophene (3.21 g, 19.7 mmol), and (trimethylsilyl)acetylene (2.13 g, 21.7 mmol) was added Pd(PPh$_3$)$_4$ (0.03 g, 0.026 mmol), followed by CuI (0.01 g, 0.05 mmol) and PPh$_3$ (0.015 g, 0.057 mmol). The reaction mixture was heated at the reflux temperature for 45 min., and was allowed to cool to room temperature. The resulting dark brown slurry was diluted with pentane (20 mL) and water (20 mL) and the aqueous layer was extracted with pentane (2×20 mL). The organic layers were washed with a saturated NH$_4$Cl solution (4 mL) and a 3M HCl solution (4 mL), dried (MgSO$_4$) and concentrated under reduced pressure to give 2-(2-thienyl)-1-trimethylsilylacetylene (2.79 g, 79%) as a reddish brown oil: GC-MS m/z (rel abundance) 180 (M$^+$, 30%); $^1$H NMR (CDCl$_3$) δ 0.15 (s, 9H), 6.79 (m, 1H), 7.15 (m, 2H).

Intermediate I

Preparation of (3-carboxyphenyl)boronic acid

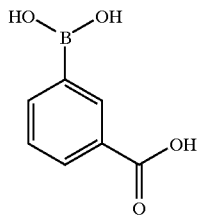

A solution of KMnO$_4$ (3.7 g, 23.4 mmol) in water (100 mL) was slowly added to a solution of (3-methylphenyl) boronic acid (1.5 g, 11 mmol) and NaOH (1 g, 25 mmol) in water (60 mL), while the temperature was maintained between 30° C. and 40° C. using a water bath. The resulting brown suspension was heated at 55° C. for 2 h and allowed to cool to room temperature. EtOH (1 mL) was added, the resulting slurry was filtered and the filtrate concentrated to 100 mL under reduced pressure. The resulting mixture was acidified with conc. HCl (1.5 mL) and kept at 5° C. overnight. The white suspension was filtered to give (3-carboxyphenyl)boronic acid (1.44 g, 79%) as a white solid: $^1$H NMR (D$_2$O) δ 7.51 (m, 1H), 7.99 (m, 1H), 8.07 (m, 1H), 8.4 (s, 1H).

Intermediate J

Preparation of Dimethyl(5-(2-thienyl)(2-pyridyl)) amine

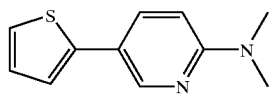

To a suspension of magnesium (0.119 g, 4.97 mmol) in THF (3 mL) was added 2-bromothiophene (0.811 g, 4.97 mmol) and the reaction mixture was stirred for 3 h. Another equivalent of 2-bromothiophene (0.811 g, 4.97 mmol) was added and the reaction mixture was heated at the reflux temperature for 2 h, then allowed to cool to room temperature. The resulting mixture was added to a solution of 5-bromo-2-dimethylaminopyridine (1.0 g, 4.97 mmol) in THF (12 mL) and the reaction was heated at the reflux temperature for 11 h, then was allowed to cool to room temperature. The resulting mixture was treated with water (10 mL), extracted with EtOAc (3×30 mL), dried (MgSO$_4$) and concentrated under reduced pressure. The crude product was purified by flash chromatography (10% EtOAc/hex) to give 5-(2-thienyl)-2-dimethylaminopyridine (0.3 g, 29%): TLC (10% EtOAc/hex) R$_f$ 0.24; HPLC ES-MS m/z (relative abundance) 205 (MH$^+$, 100%).

Intermediate K

Preparation of 2-(5-methyl-2-pyridyl)thiophene

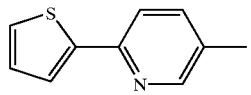

A mixture of 2-thiopheneboronic acid (0.483 g, 3.78 mmol), 2-bromo-5-methylpyridine (0.5 g, 2.91 mmol), a solution of Na$_2$CO$_3$ (1M in H$_2$O, 7.8 mL, 7.8 mmol) and a catalytic amount of Pd(PPh$_3$)$_4$ in DME (10 mL) was heated at the reflux temperature for 3 h., then allowed to cool to room temperature and poured onto ice. The resulting mixture was stirred for 10 min and extracted with CH$_2$Cl$_2$ (2×25 mL), dried (MgSO$_4$) and concentrated under reduced pressure. The crude product was purified by flash chromatography (70% EtOAc/hex) to give 2-(5-methyl-2-pyridyl) thiophene (0.499 g, 98%): GC-MS m/z (rel abundance) 176 (MH$^+$, 100%); $^1$H NMR (CDCl$_3$) δ 1.39 (s, 3H), 7.15 (m, 1H), 7.39 (m, 1H), 7.61–7.43 (m, 3H), 8.41 (s, 1H).

Intermediate L

Preparation of 5-bromo-2-{[4-(4-fluorophenyl) piperazinyl]sulfonyl}thiophene

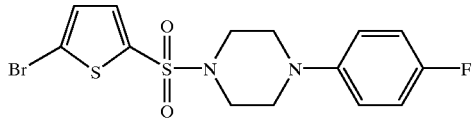

To a solution of (5-bromo(2-thienyl))chlorosulfone (1.09 g, 4.16 mmol) in CH$_2$Cl$_2$ (30 mL) was added triethylamine (0.4 mL, 3.052 mmol), followed by (4-fluorophenyl) piperazine (500 mg, 2.77 mmol). The resulting mixture was stirred at room temperature overnight. The reaction was treated with a saturated NaHCO$_3$ solution (1 mL) and extracted with EtOAc (3×10 mL). The combined organic layers were washed with a saturated NaCl solution (10 mL), dried (MgSO$_4$) and concentrated under reduced pressure to give a brown solid. The crude product was purified flash chromatography (10% EtOAc/hex) to give 5-bromo-2-{[4-(4-fluorophenyl)piperazinyl]sulfonyl}thiophene (1.12 g, 100%) as a white solid: mp 123–124° C.; TLC (EtOAc) R$_f$ 0.44; HPLC ES-MS m/z 406 (MH$^+$).

Intermediate M

Preparation of 5-[(1Z)-2-(4-fluorophenyl)vinyl]-2-bromothiophene and 5-[(1E)-2-(4-fluorophenyl) vinyl]-2-bromothiophene

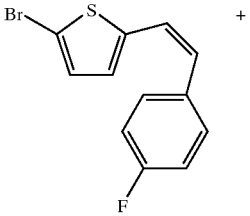

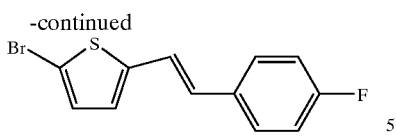

To a 0° C. suspension of 4-fluorobenzyl triphenylphosphonium chloride (1.82 g, 4.47 mmol) in THF (20 mL) was added a solution of n-BuLi (2.5M in hexane, 1.8 mL, 4.47 mmol) and the reaction mixture was stirred for 1 h. 5-Bromothiophene-2-carbaldehyde was added, the reaction was allowed to warm to room temperature and stirred for 1 h. The resulting mixture was treated with water and extracted with Et$_2$O. The crude product was purified by preparative TLC (30% EtOAc/hex) to give 5-[(1Z)-2-(4-fluorophenyl)vinyl]-2-bromothiophene (170 mg, 13%) as a colorless oil: $^1$H NMR (CDCl$_3$) δ 6.51 (d, J=11.9 Hz, 1H), 6.59 (d, J=11.9 Hz, 1H), 6.72 (d, J=4.3 Hz, 1H), 6.85 (d, J=3.8 Hz, 1H), 7.04–7.11 (m, 2H), 7.27–7.33 (m, 2H) and 5-[(1E)-2-(4-fluorophenyl)vinyl]-2-bromothiophene (200 mg, 16%) as a white solid: $^1$H NMR (CDCl$_3$) δ 6.74–6.80 (m, 2H), 6.95–7.07 (m, 4H), 7.39–7.44 (m, 2H).

Intermediate N

Preparation of 2-(4-fluorobenzyl)thiophene

Step 1: Preparation of (4-fluorophenyl)-2-thienylmethan-1-ol

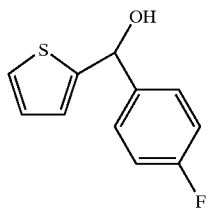

To a solution of 2-(4-fluorobenzoyl)thiophene (5.09 g, 24.7 mmol) in Et$_2$O (100 mL) was added a solution of LiAlH$_4$ (1M in THF, 30 mL, 30 mmol) and the reaction mixture was stirred overnight. The resulting mixture was cooled to 0° C., poured onto ice, extracted with Et$_2$O, dried (Na$_2$SO$_4$) and concentrated under reduced pressure to give (4-fluorophenyl)-2-thienylmethan-1-ol as a yellow oil. The crude product was used without further purification.

Step 2: Preparation of 2-(4-fluorobenzyl)thiophene

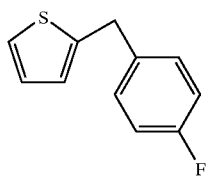

To a suspension of NaI (8 g, 53 mmol) in CH$_3$CN (100 mL) was added TMSCl (6.8 mL, 54 mmol). The resulting mixture was cooled to 0° C. and treated with (4-fluorophenyl)-2-thienylmethan-1-ol, allowed to warm to room temperature, stirred overnight, then cooled to 0° C. and treated with water. The resulting mixture was extracted with EtOAc. The organic layer was washed with a saturated Na$_2$S$_2$O$_3$ solution, water and a saturated NaCl solution, then concentrated under reduced pressure. The crude product was purified by flash chromatography (hex) to give 2-(4-fluorobenzyl)thiophene (1.89 g, 40% overall yield) as a pink oil: TLC (hex) R$_f$ 0.69; $^1$H NMR (CDCl$_3$) δ 4.14 (s, 2H), 6.80–6.82 (m, 1H), 6.93–7.04 (s, 3H), 7.16–7.28 (m, 3H).

Intermediate O

Preparation of 2-(4-fluorophenyl)-thiophene

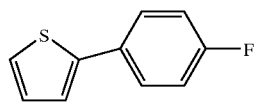

To a solution of 2-bromothiophene (1.0 g, 6.14 mmol) in 1,2-dimethoxyethane (11 mL) was added 4-fluorophenylboronic acid (1.12 g, 7.99 mmol), followed by Pd(PPh3)$_4$ (360 mg, 0.31 mmol) and a 2M Na$_2$CO$_3$ aq. solution (8 mL). The reaction mixture was heated at 80° C. for 4 h, then was poured onto a mixture of ice and CH$_2$Cl$_2$. The aqueous layer was extracted with CH$_2$Cl$_2$ (3×20 mL). The organic layers were dried (MgSO$_4$) and concentrated under reduced pressure to yield a yellow oil. The crude product was filtered through a plug of silica with the aid of hexanes to give 4-fluorophenylthiphene (1.04 g, 95%). TLC (hex) R$_f$=0.40.

Intermediate P

Preparation of 1-(4-bromophenyl)-4-tert-butyldimethylsilyloxy Benzene

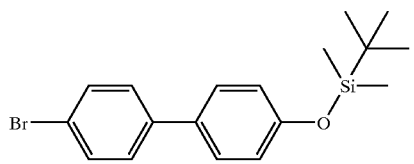

To a 0° C. solution of 4-(4-bromophenyl)phenol (1.0 g, 4.0 mmol) and pyridine (0.65 mL, 8 mmol) in CH$_2$Cl$_2$ (20 mL) was added chloro-tert-butyldimethylsilane (0.72 g, 4.8 mmol). The resulting mixture was allowed to warm to room temperature and stirred for 3 days, then diluted with water and extracted with CH$_2$Cl$_2$. The organic layer was washed with a 2N HCl solution, a 1N KOH solution, dried (MgSO$_4$) and concentrated under reduced pressure to yield 1-(4-bromophenyl)-4-tert-butyldimethylsilyloxybenzene (0.89 g, 61%) as a white solid: TLC (33% EtOAc/hex) R$_f$ 0.57.

Intermediate Q

Preparation of 2-(4-trimethylsilyloxyphenyl)thiophene

Step 1: Preparation of 4-(2-thienyl)phenol

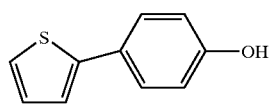

To a −78° C. solution of 2-(4-methoxyphenyl)thiophene (0.501 g, 2.64 mmol) in anh. CH$_2$Cl$_2$ (40 mL) was added a solution of BBr$_3$ (1M in CH$_2$Cl$_2$, 6.6 mL, 6.6 mmol), keeping the temperature below −60° C. The reaction mixture was allowed to warm to room temperature and stirred overnight. The resulting mixture cooled to 0° C. and treated with a saturated NaHCO$_3$ solution. After separation the aqueous layer was extracted with CH₂Cl₂ and EtOAc. The combined organic layers were washed with a saturated NaCl solution, dried (Na₂SO₄) and concentrated under reduced pressure. The crude product was purified by flash chromatography (20% EtOAc/hex) to give 4-(2-thienyl)phenol: TLC (20% EtOAc/hex) R_f 0.29.

Step 2: Preparation of 2-(4-trimethylsilyloxyphenyl)thiophene

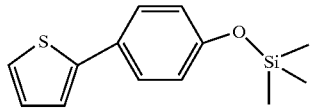

To a solution of 4-(2-thienyl)phenol in anhyd. THF (10 mL) was added Et₃N (0.9 mL, 6.5 mmol), followed by TMSCl (0.4 mL, 3.2 mmol). The reaction mixture was stirred at room temperature overnight, then filtered and concentrated under reduced pressure to give 2-(4-trimethylsilyloxyphenyl)thiophene: TLC (20% EtOAc/hex) R_f 0.69. This material was used without further purification.

Intermediate R

Preparation of N-{2-[(4S)-2-oxo-4-benzyl(1,3-oxazolidin-3-yl)]-2-oxoethyl}-N-methyl-3-phenylprop-2-ynamide Method 1:

Step 1: Preparation of N-{2-[(4S)-2-oxo-4-benzyl(1,3-oxazolidin-3-yl)]-2-oxoethyl}(tert-butoxy)-N-methylcarboxamide

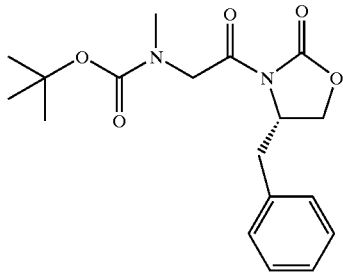

A −78° C. solution of (S)-(−)-4-benzyl-2-oxazolidinone (3.54 g, 20 mmol) in anhyd. THF (50 mL) was treated with a solution of n-BuLi (2.5M in hexanes, 13.2 mL, 21 mmol, 1.05 equiv) at such a rate that the temperature was maintained below −65° C. The reaction was stirred at −78° C. for 10 minutes following the addition. Meanwhile, a 0° C. solution of N-BOC-sarcosine (4.16 g, 22 mmol, 1.1 equiv) and Et₃N (5.6 mL, 40 mmol, 2 equiv) in anhyd. THF (80 mL) was treated dropwise with a solution of PivCl (2.8 mL, 23 mmol, 1.15 equiv) in THF (20 mL). The resulting white slurry was stirred for 10 min, allowed to warm to 0° C., then cooled back to −78° C.

To this mixture was added via cannula a −78° C. solution of the oxazolidinone/BuLi mixture prepared above. The reaction was stirred for 2 h, allowed to warm to 0° C. over 30 minutes and treated with a saturated NH₄Cl solution (20 mL). The resulting mixture was partitioned between water (50 mL) and EtOAc (50 mL). The organic layer was washed with a saturated NaHCO₃ solution (50 mL) and a saturated NaCl solution (50 mL), dried (Na₂SO₄) and concentrated under reduced pressure to give N-{2-[(4S)-2-oxo-4-benzyl(1,3-oxazolidin-3-yl)]-2-oxoethyl}(tert-butoxy)-N-methylcarboxamide (7.45 g, 100%) as a colorless oil: TLC (30% EtOAc/hex) R_f 0.42; HPLC ES-MS m/z (rel abundance) 348 (MH⁺, 8%).

Step 2: Preparation of (4S)-3-[2-(methylamino)acetyl]-4-benzyl-1,3-oxazolidin-2-one

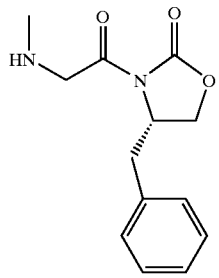

HCl gas was bubbled into a solution of N-{2-[(4S)-2-oxo4-benzyl(1,3-oxazolidin-3-yl)]-2-oxoethyl}(tert-butoxy)-N-methylcarboxamide (7.2 g, 21 mmol) in Et₂O (150 mL) over 30 min. The resulting white slurry was stirred for 2 h, allowed to warm to room temperature, and stirred for 2 h. A solution of HCl (1M in Et₂O, 20 mL, 20 mmol, 3.6 equiv) was added and the reaction mixture was stirred overnight, then treated with TFA (10 mL), and stirred for 2 h. HCl gas was again bubbled into the mixture over 15 min, and the reaction was stirred for 3 h. The resulting mixture was concentrated under reduced pressure and the residue was triturated (100 mL of 50% EtOAc/hexanes). The resulting precipitate was filtered and washed with hexanes to give (4S)-3-[2-(methylamino)acetyl]-4-benzyl-1,3-oxazolidin-2-one (5.69 g, 96%) as a white solid: ¹H NMR (CDCl₃) δ 2.62 (br s, 3H), 2.91–3.04 (m, 2H), 4.22–4.44 (m, 4H), 4.65–4.73 (m, 1H), 7.22–7.34 (m, 5H), 9.26 (br s, 2H); HPLC ES-MS m/z (rel abundance) 249 (MH⁺, 100%).

Step 3: Preparation of N-{2-[(4S)-2-oxo-4-benzyl(1,3-oxazolidin-3-yl)]-2-oxoethyl}-N-methyl-3-phenylprop-2-ynamide

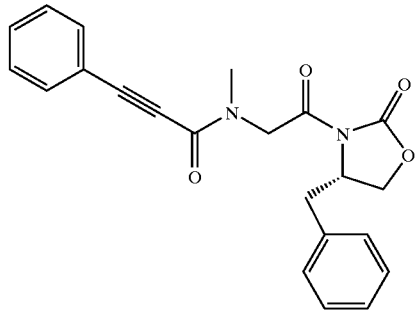

A 0° C. solution of (4S)-3-[2-(methylamino)acetyl]-4-benzyl-1,3-oxazolidin-2-one (in 5.0 g, 18 mmol) in CH₂Cl₂ (100 mL) was treated with DMAP (2.14 g, 18 mmol), NMM (4.8 mL, 44 mmol), phenylpropiolic acid (2.8 g, 19 mmol) and EDCI.HCl (3.7 g, 19 mmol). The reaction mixture was allowed to warm to room temperature and stirred overnight. The resulting mixture was concentrated under reduced pressure and the residue was partitioned between EtOAc (100 mL) and water (100 mL). The organic layer was washed with a 5% citric acid solution (2×50 mL), a saturated NaHCO₃ solution (2×50 mL) and a saturated NaCl solution (50 mL), dried (Na₂SO₄) and concentrated under reduced pressure. The crude product was purified by flash chromatography (gradient from 15% to 35% EtOAc/hex) to afford N-{2-[(4S)-2-oxo-4-benzyl(1,3-oxazolidin-3-yl)]-2- oxoethyl}-N-methyl-3-phenylprop-2-ynamide (4.02 g, 61%) as a white foam: TLC (40% EtOAc/hex) $R_f$ 0.28; $^1$H NMR (CDCl$_3$) δ 2.77–2.89 (m, 1H), 3.12 (s, 1H), 3.23–3.38 (m, 1H), 3.39 (s, 2H), 4.23–4.34 (m, 2H), 4.66–4.85 (m, 2.2H), 4.96 (d, J=19.1 Hz, 0.4H), 5.13 (d, J=19.1 Hz, 0.4H), 7.13–7.61 (m, 10H); HPLC ES-MS m/z (rel abundance) 377 (MH$^+$, 100%).

Method 2:

Step 1: Preparation of 2-(N-methyl-3-phenylprop-2-ynoylamino)acetic Acid

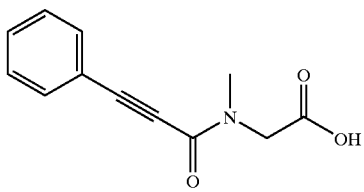

To a 0° C. solution of ethyl 2-(N-methyl-3-phenylprop-2-ynoylamino)acetate (prepared according to the procedure described for Intermediate A, 124.4 g, 0.507 mol) in MeOH (750 mL) was added a solution of NaOH (30.4 g, 0.760 mol, 1.5 equiv) in water (1000 mL). The resulting red reaction mixture was stirred for 20 min, then allowed to warm to room temperature and stirred for 2 h. The reaction was washed with CH$_2$Cl$_2$ (3×500 mL). The aqueous layer was cooled in an ice bath and acidified to pH 3 using conc. HCl. A light orange oil formed, which was extracted into EtOAc (4×500 mL). The combined EtOAc layers were washed with water (3×200 mL) and a saturated NaCl solution (2×300 mL), dried (Na$_2$SO$_4$) and concentrated under reduced pressure to give 2-(N-methyl-3-phenylprop-2-ynoylamino) acetic acid (102.5 g, 93%) as an orange solid: TLC (1% AcOH/5% MeOH/CH$_2$Cl$_2$) $R_f$ 0.20; $^1$H NMR (CDCl$_3$) δ 3.09 (s, 1.1H, N—CH$_3$), 3.36 (s, 1.9H, N—CH$_3$), 4.27 (s, 1.2H, N—CH$_3$), 4.45 (s, 0.8H, N—CH$_3$), 7.30–7.56 (m, 5H), 9.58 (br s, 1H).

Step 2: Preparation of N-{2-[(4S)-2-oxo-4-benzyl(1,3-oxazolidin-3-yl)]-2-oxoethyl}-N-methyl-3-phenylprop-2-ynamide

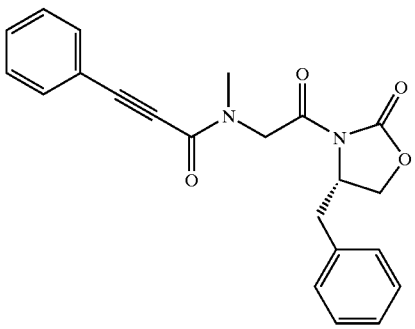

To a −30° C. solution of 2-(N-methyl-3-phenylprop-2-ynoylamino)acetic acid (100.0 g, 0.460 mol, 1.1 equiv) and Et$_3$N (117 mL, 0.836 mol, 2 equiv) in THF (1100 mL) was added a solution of PivCl (57 mL, 0.460 mol, 1.1 equiv) in THF (100 mL) at such a rate that the temperature was maintained below −20° C. The resulting white slurry was stirred at −20° C. Meanwhile, a −78° C. solution of (S)-(−)-4-benzyl-2-oxazolidinone (74.1 g, 0.418 mol) in THF (900 mL) was treated with a solution of n-BuLi (2.5M in hexane, 185 mL, 0.460 mol, 1.1 equiv) at such a rate that the temperature was maintained below −68° C. The reaction was stirred at −78° C. for 15 min. To this mixture was added via cannula a −78° C. solution of the mixed anhydride prepared above. The reaction was allowed to warm to −10° C. over 30 min and treated with a saturated NH$_4$Cl solution (500 mL). The resulting mixture was concentrated under reduced pressure and the residue was partitioned between water (200 mL) and EtOAc (500 mL). The organic layer was washed with water (3×300 mL), a saturated NaHCO$_3$ solution (2×300 mL) and a saturated NaCl solution (2×300 mL), dried (Na$_2$SO$_4$) and concentrated under reduced pressure. The crude product was purified by flash chromatography (gradient from 25% to 65% EtOAc/hex) to give N-{2-[(4S)-2-oxo-4-benzyl(1,3-oxazolidin-3-yl)]-2-oxoethyl}-N-methyl-3-phenylprop-2-ynamide (119.6 g, 74%) as a white foam. Analytical data of this product was identical to Intermediate R obtained by Method 1.

Intermediate S

Preparation of (4R,5R)-5-(ethoxycarbonyl)-4-phenylpyrrolidin-2-one

Step 1: Preparation of Ethyl 2-{[(1S)-1-(4-methoxyphenyl)ethyl]amino}acetate

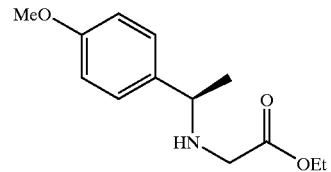

To a 0° C. solution of (S)-(−)-1-(4-methoxyphenyl) ethylamine (25 g, 165 mmol) and Et$_3$N (46 mL, 330 mmol) in THF (350 mL) was added a solution of ethyl bromoacetate (27.5 mL, 248 mmol) in THF (50 mL) dropwise over 30 min. The reaction mixture was allowed to warm to room temperature, stirred overnight, then diluted with EtOAc and washed with water and a saturated NaCl solution. The organic layer was dried (Na$_2$SO$_4$) and concentrated under reduced pressure to give ethyl 2-{[(1S)-1-(4-methoxyphenyl)ethyl]amino}acetate (40 g, 100%) as a colorless oil: TLC (40% EtOAc/hex) $R_f$ 0.4; $^1$H NMR (CDCl$_3$) δ 1.25 (t, J=7.2 Hz, 3H), 1.37 (d, J=6.6 Hz, 3H), 2.03 (br s, 1H), 3.21 (d, J=17.6 Hz, 1H), 3.29 (d, J=17.6 Hz, 1H),), 3.76 (q, J=6.6 Hz, 1H), 3.81 (s, 3H), 4.16 (q, J=7.2 Hz, 2H), 6.87 (d, J=8.7 Hz, 2H), 7.23 (d, J=8.7 Hz, 2H); $^{13}$C NMR (CDCl$_3$) δ 14.1, 24.2, 48.8, 55.2, 57.0, 60.6, 113.8, 127.8, 136.6, 158.7, 172.6; HPLC ES-MS m/z (rel abundance) 238 (MH$^+$, 100%).

Step 2: Preparation of Ethyl 2-{N-[(1S)-1-(4-methoxyphenyl)ethyl]-3-phenylprop-2-ynoylamino}acetate

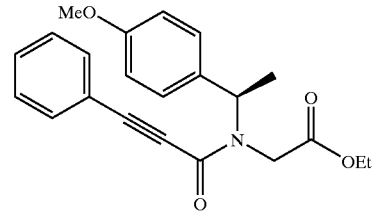

A mixture of phenylpropiolic acid (10 g, 68.4 mmol) and thionyl chloride (6 mL, 76.6 mmol) in Et$_2$O (50 mL) was stirred overnight at room temperature. The resulting mixture was concentrated under reduced pressure, then diluted with THF (100 mL). This acid chloride solution was added to a 0° C. solution of ethyl 2-{[(1S)-1-(4-methoxyphenyl)ethyl]amino}acetate (15 g, 63.2 mmol) and Et₃N (22 mL, 156 mmol) in THF (250 mL) dropwise over 25 min. The reaction mixture was allowed to warm to room temperature, stirred for 1.5 h, then treated with water and extracted with EtOAc. The organic layer was washed with a 1N HCl solution, water, a saturated NaHCO₃ solution and a saturated NaCl solution. The organic layer was dried (Na₂SO₄) and concentrated under reduced pressure to give ethyl 2-{N-[(1S)-1-(4-methoxyphenyl)ethyl]-3-phenylprop-2-ynoylamino}acetate (18.9 g, 82%) as a slightly yellow oil: TLC (40% EtOAc/hex) $R_f$ 0.40; $^1$H NMR (CDCl₃) δ 1.14–1.33 (m, 3H), 1.66 (d, J=7.0 Hz, 3H), 3.82 (s, 3H), 4.06–4.21 (m, 4H), 5.59 (q, J=7.4 Hz, 0.6H), 6.03 (q, J=7.4 Hz, 0.4H), 6.86–6.93 (m, 2H), 7.25–7.61 (m, 7H); HPLC ES-MS m/z (rel abundance) 388 (MH⁺, 100%).

Step 3: Preparation of Ethyl 1-[(1S)-1-(4-methoxyphenyl)ethyl]-5-oxo-3-phenyl-3-pyrroline-2-carboxylate

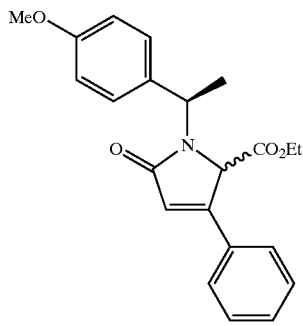

To a –10° C. degassed solution of LiN(SiMe₃)₂ (1M in THF, 46.2 mL, 46.2 mmol) in THF (70 mL) was added a solution of ethyl 2-{N-[(1S)-1-(4-methoxyphenyl)ethyl]-3-phenylprop-2-ynoylamino}acetate (13.5 g, 36.9 mmol) in THF (60 mL) dropwise over 30 min. The reaction mixture was allowed to warm to room temperature, stirred for 1.5 h, then acidified with a 1N HCl solution. The resulting mixture was extracted with EtOAc, washed with water and a saturated NaCl solution. The organic layer was dried (Na₂SO₄) and concentrated under reduced pressure to give a yellow oil (15 g). The crude product was purified by flash chromatography (25% EtOAc/hex) to give ethyl 1-[(1S)-1-(4-methoxyphenyl)ethyl]-5-oxo-3-phenyl-3-pyrroline-2-carboxylate (13 g, 96%): $^1$H NMR (CDCl₃) δ 0.82 (dt, J=1.1, 7.4 Hz, 1.5H), 1.09 (dt, J=1.1, 7.5 Hz, 1.5H), 1.59 (d, J=7.0 Hz, 1.5H), 1.71 (d, J=7.5 Hz, 1.5H), 3.32–3.60 (m, 1H), 3.81 (s, 1.5H), 3.82 (s, 1.5H), 4.07 (q, J=7.5 Hz, 1H), 4.81 (s, 0.5H), 5.17 (s, 0.5H), 5.53 (q, J=7.0 Hz, 0.5H), 5.63 (q, J=7.0 Hz, 0.5H), 6.46 (app t, 0.5H), 6.49 (app t, 0.5H), 6.84 (d, J=8.6 Hz, 1H), 6.90 (d, J=8.1 Hz, 1H), 7.26–7.63 (m, 7H); HPLC ES MS m/z (rel abundance) 366 (MH⁺, 100%).

Step 4: Preparation of (4R,5R)-5-(ethoxycarbonyl)-1-(4-methoxyphenyl)ethyl]-4-phenylpyrrolidin-2-one

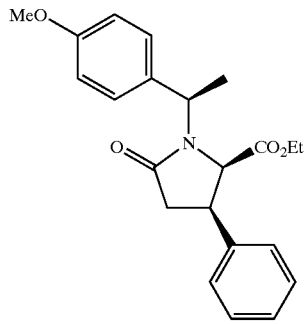

A mixture of ethyl 1-[(1S)-1-(4-methoxyphenyl)ethyl]-5-oxo-3-phenyl-3-pyrroline-2-carboxylate (5 g, 13.7 mmol) and 10% palladium on carbon (0.5 g) was maintained under a H₂ atmosphere (55 psi) overnight. The resulting mixture was filtered through a plug of Celite© and silica gel to give ethyl cis-1-[(1S)-1-(4-methoxyphenyl)ethyl]-5-oxo-3-phenylpyrrolidine-2-carboxylate (5 g, 100%). The mixture of diastereomers was triturated (Et₂O) to give (4R,5R)-5-(ethoxycarbonyl)-1-(4-methoxyphenyl)ethyl]-4-phenylpyrrolidin-2-one (2.0 g, 40%): $^1$H NMR (CDCl₃) δ 0.62 (t, J=7.1 Hz, 3H). 1.60 (d, J=6.9 Hz, 3H), 2.60 (q, J=8.1 Hz, 1H), 3.09–3.30 (m, 3H), 3.70–3.88 (m, 4H), 4.31 (d, J=8.3 Hz, 1H), 5.52 (q, J=7.3 Hz, 1H), 6.76–6.82 (m, 2H), 7.15–7.31 (m, 7H); HPLC ES-MS m/z (rel abundance) 368 (MH⁺, 100%).

Step 5: Preparation of (4R,5R)-5-(ethoxycarbonyl)-4-phenylpyrrolidin-2-one

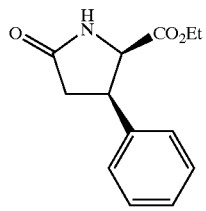

A solution of (NH₄)₂Ce(NO₃)₆ (6.91 g, 12.7 mmol) in water 50 mL was added dropwise to a –10° C. solution of (4R,5R)-5-(ethoxycarbonyl)-1-(4-methoxyphenyl)ethyl]-4-phenylpyrrolidin-2-one (1.56 g, 10 mmol) in acetonitrile (75 mL). The resulting mixture was stirred for 30 min, then diluted with water (100 mL) and extracted with EtOAc. The organic layer was washed with a saturated NaHCO₃ solution, a 40% NaHSO₃ solution and a 1:1 mixture of a saturated NaHCO₃ solution and a saturated NaCl solution. The organic layer was dried (Na₂SO₄) and concentrated under reduced pressure to give (4R,5R)-5-(ethoxycarbonyl)-4-phenylpyrrolidin-2-one (1.5 g, 64%): $[\alpha]^{20}_D$+172° (c 1 MeOH); $^1$H NMR (CDCl₃) δ 0.82 (t, J=7.1 Hz, 3H), 2.74 (d, J=8.0 Hz, 2H), 3.60–3.90 (m, 2H), 3.97 (q, J=7.9 Hz, 1H), 4.53 (d, J=7.9 Hz, 1H), 6.05 (br s, 1H), 7.21–7.29 (m, 5H); HPLC ES-MS m/z (rel abundance) 234 (MH⁺, 100%).

Intermediate T

Preparation of (4R,5R)-5-(hydroxymethyl)-1-methyl-4-phenylpyrrolidin-2-one

Method 1:

Step 1: Preparation of (4S)-3-[((2R)-1-methyl-5-oxo-3-phenyl(3-pyrrolin-2-yl)carbonyl]-4-benzyl-1,3-oxazolidin-2-one and (4S)-3-[((2S)-1-methyl-5-oxo-3-phenyl(3-pyrrolin-2-yl))carbonyl]-4-benzyl-1,3-oxazolidin-2-one

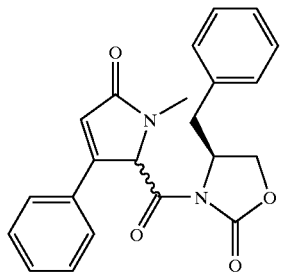

To a 0° C. solution of N-{2-[(4S)-2-oxo-4-benzyl(1,3-oxazolidin-3-yl)]-2-oxoethyl}-N-methyl-3-phenylprop-2-ynamide (Intermediate R, Method 1, 120 g, 0.317 mol) in THF (1100 mL) was added a solution of LiN(SiMe₃)₂ (1M in THF, 317.8 mL, 0.317 mol). The resulting mixture was allowed to warm to room temperature and stirred for 3 h. The reaction was cooled to 0° C., treated with a saturated NH₄Cl solution (250 mL) and concentrated under reduced pressure. The residue was extracted with EtOAc (3×250 mL). The combined organic layers were washed with a 0.1N HCl solution (2×200 mL) and a saturated NaCl solution (200 mL), dried (Na2SO₄) and concentrated under reduced pressure. The crude product was purified by flash chromatography (gradient from 0% to 30% EtOAc/CH₂Cl₂) to give a 1.3:1 diastereomeric ratio of (4S)-3-[((2R)-1-methyl-5-oxo-3-phenyl(3-pyrrolin-2-yl)carbonyl]-4-benzyl-1,3-oxazolidin-2-one and (4S)-3-[((2S)-1-methyl-5-oxo-3-phenyl(3-pyrrolin-2-yl))carbonyl]-4-benzyl-1,3-oxazolidin-2-one (78.5 g, 65%) as a white foam: TLC (50% EtOAc/hex) $R_f$ 0.28; partial ¹H NMR (CDCl₃) δ 3.04 (s, 1.7H), 3.07 (s, 1.3H), 4.42–4.50 (m, 0.9H), 4.65–4.74 (m, 1.1H); HPLC ES-MS m/z (rel abundance) 377 (MH⁺, 100%).

Step 2: Preparation of 3-[((2R,3R)-1-methyl-5-oxo-3-phenylpyrrolidin-2-yl)carbonyl](4S)4-benzyl-1,3-oxazolidin-2-one

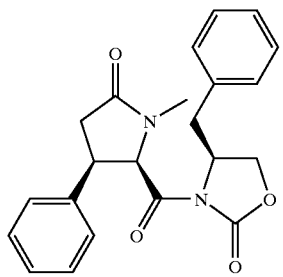

To a slurry of 10% palladium on carbon (7.0 g) in EtOAc (700 mL) was added a solution of diastereomers 3-[((2R)-1-methyl-5-oxo-3-phenyl(3-pyrrolin-2-yl)carbonyl](4S)-4-benzyl-1,3-oxazolidin-2-one and (4S)-3-[((2S)-1-methyl-5-oxo-3-phenyl(3-pyrrolin-2-yl))carbonyl]-4-benzyl-1,3-oxazolidin-2-one (78.5 g, 0.208 mol) in EtOH (100 mL) and the reaction mixture was stirred under a H₂ atmosphere (1 Atm) for 2 days. The reaction mixture was filtered through a pad of Celite® with the aid of EtOAc. The filtrate was concentrated under reduced pressure and purified by flash chromatography (gradient from 15% to 65% EtOAc/hex) to give diastereomer 3-[((2R,3R)-1-methyl-5-oxo-3-phenylpyrrolidin-2-yl)carbonyl](4S)-4-benzyl-1,3-oxazolidin-2-one as a single diastereomer (41.02 g, 52%): TLC (15% i-PrOH/hex) $R_f$ 0.25; ¹H NMR (CDCl₃) δ 1.39 (dd, J=11.4, 13.6 Hz, 1H), 2.45–2.51 (dd, J=3.3, 13.6 Hz, 1H), 2.87–2.91 (m, 5H), 3.91 (dd, J=9.2, 2.9 Hz, 1H), 4.03–4.23 (m, 3H), 4.36–4.43 (m, 1H), 5.75 (d, J=9.2 Hz, 1H), 7.01–7.03 (m, 2H), 7.21–7.39 (m, 8H); HPLC ES-MS m/z (rel abundance) 377 (MH⁺, 100%).

Step 3: Preparation of (4R,5R)-5-(hydroxymethyl)-1-methyl-4-phenylpyrrolidin-2-one

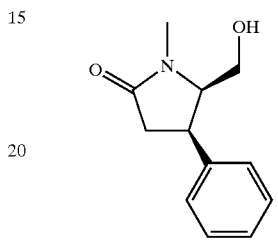

To a 0° C. solution of 3-[((2R,3R)-1-methyl-5-oxo-3-phenylpyrrolidin-2-yl)carbonyl](4S)4-benzyl-1,3-oxazolidin-2-one (41.02 g, 0.108 mol) and MeOH (4.83 mL, 0.119 mol, 1.1 equiv) in THF (500 mL) was added LiBH₄ (2.60 g, 0.119 mol, 1.1 equiv) in two portions. The reaction was allowed to warm to room temperature and stirred overnight, then cooled to 0° C. and treated with a saturated NH₄Cl solution (100 mL). The resulting mixture was concentrated under reduced pressure and the residue was extracted with EtOAc (3×200 mL). The combined organic layers were washed with a saturated NaCl solution (200 mL), dried (Na₂SO₄) and concentrated under reduced pressure. The crude product was dissolved in a minimal amount of CH₂Cl₂, then diluted with Et₂O. The resulting precipitate was collected by filtration and washed with Et₂O to give (4R,5R)-5-(hydroxymethyl)-1-methyl-4-phenylpyrrolidin-2-one (10.4 g, 47%) as a white solid: TLC (5% MeOH/CH₂Cl₂) $R_f$ 0.48; ¹H NMR (CDCl₃) δ 2.54 (dd, J=8.4, 16.6 Hz, 1H), 2.79 (s, 1H), 2.90–3.03 (m, 4H), 3.33 (dd, J=8.4, 16.6 Hz, 1H), 3.61–3.83 (m, 3H), 7.25–7.39 (m, 5H); ¹³C NMR (CDCl₃) δ 28.6, 35.6, 41.6, 59.6, 65.5, 127.2, 128.0, 128.7, 137.7, 146.5, 175.2; HPLC ES-MS m/z (rel abundance) 206 (MH⁺, 100%).

Method 2:

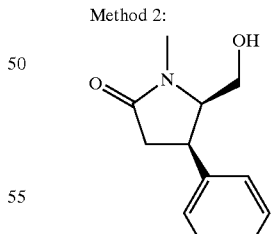

(±)-(4R*,5R*)-5-(ethoxycarbonyl)-1-methyl-4-phenylpyrrolidin-2-one, and (±-(4R*,5R*)-5-(hydroxymethyl)-1-methyl-4-phenylpyrrolidin-2-one were synthesized using the literature method (W. Hartwig and L. Born, *J. Org. Chem.* 1987, 52, 4352 or Rudorf, W.-D., Schwarz, R. *Z. Chem.* 1988, 28, 101). The conversion of the ester to the alcohol was carried out as follows:

Lithium triethylborohydride solution (4.24 L, 1.0M/THF) was steadily added (over 45 minutes) to a cold (−20° C.), stirred solution containing (±)-(4R*,5R*)-5-(Ethoxycarbonyl)-1-methyl-4-phenylpyrrolidin-2-one (500 g, 2.02 mole) in tetrahydrofuran (4L). The internal temperature was kept below −15° C. during the addition; the reaction was then allowed to warm to 0° C. and stirred for 1 hour. The reaction mixture was then cooled back down to −5° C. and cold 4N hydrochloric acid solution (made from 1000 mL ice water and 500 mL conc. HCl) was added over a 7–8 minute period with vigorous stirring. After stirring for 30 minutes (internal temp. ~12° C.) the pH was adjusted to 7–8 by adding solid potassium carbonate. The reaction mixture was allowed to warm to room temperature, at which time the organic layer was separated and washed with brine (4 L). The organic layer was concentrated to near dryness, and hexane (200 ml) was added to precipitate a yellow solid. The solid was filtered, washed with hexane (500 ml) and dried under vacuum to give 345.12g (83%) of (±)-(4R*,5R*)-5-(hydroxymethyl)-1-methyl-4-phenylpyrrolidin-2-one. NMR (CDCl$_3$) δ 2.35 (br s, 1H, OH), 2.56 (m, 1H, CH$_2$), 2.94 (s, 3H, CH$_3$), 3.01 (m, 1H, CH$_2$), 3.34 (dd, J=13.5, 3.1 Hz, 1H, CH), 3.63 (dd, J=12.2, 3.4 Hz, 1H, CH), 3.75 (m, 2H, CH$_2$), 7.31 (m, 5H, Ar).

The enantiomer, (−)-(4R,5R)-5-(hydroxymethyl)-1-methyl-4-phenyl-pyrrolidin-2-one, was obtained from (±)-(4R*,5R*)-5-(hydroxymethyl)-1-methyl-4-phenylpyrrolidin-2-one using the HPLC Separation D apparatus as follows:

Injection Solution Preparation: A round bottom flask fitted with a mechanical stirring apparatus was charged with ethanol and (±)-(4R*,5R*)-5-(hydroxymethyl)-1-methyl-4-phenylpyrrolidin-2-one was added via spatula such that the final ratio of ethanol/compound was ca. 4/1 (v/w). The suspension was stirred overnight, and the residue removed by vacuum filtration.

Chromatography: Flow Rate: 400 mL/min; Temp: Ambient; Eluant: Isocratic 1/1 EtOH/Hexanes; Run Time: 15 min; Injection volume: 20 mL of injection solution; Detection at 254 nM; Retention time for least retained peak: 3.3 min; Retention time for most retained peak (desired): 6.8 min.

Intermediate U

Preparation of (±)-(4R*,5R*)-5-ethoxycarbonyl-1-methyl-4-(4-aminophenyl)pyrrolidin-2-one Step 1: Preparation of (±)-(4R*,5R*)-5-ethoxycarbonyl-1-methyl-4-(4-nitrophenyl)pyrrolidin-2-one

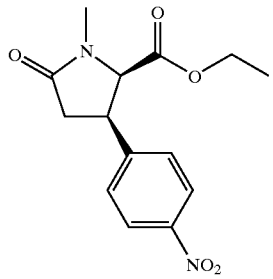

To (±)-(4R*,5R*)-5-ethoxycarbonyl-1-methyl-4-phenyl-pyrrolidin-2-one (prepared according to the procedure of Intermediate T, Method 2, 1.00 g, 4.04 mmol) was added sulfuric acid (4.0 mL). To the resulting yellow solution was added potassium nitrate (0.50 g, 4.85 mmol) in portions, keeping the reaction temperature below 30° C. The reaction mixture was stirred for 18 h, then poured onto ice water (30 mL) and extracted with CH$_2$Cl$_2$, dried (MgSO$_4$) and concentrated under reduced pressure. The oily residue was diluted with EtOAc and the resulting precipitate was collected by filtration. The solid was washed with Et$_2$O to give (±)-(4R 5R*)-5-ethoxycarbonyl-1-methyl-4-(4-nitrophenyl)pyrrolidin-2-one (374 mg, 32%) as a white solid: mp 142–143° C.; TLC (33% EtOAc/hex) Rf 0.23; HPLC ES-MS m/z 293 (MH$^+$).

Step 2: Preparation of (±)-(4R*,5R*)-5-ethoxycarbonyl-1-methyl-4-(4-aminophenyl)pyrrolidin-2-one

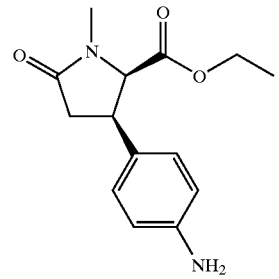

A solution of (±)-(4R*,5R*)-5-ethoxycarbonyl-1-methyl-4-(4-nitrophenyl)pyrrolidin-2-one (2.00 g, 6.85 mmol) in EtOAc (15 mL) was added to an argon flushed flask containing 10% palladium on carbon (160 mg). The resulting mixture was placed under an atmosphere of H$_2$ and stirred for 18 h. The reaction mixture then was filtered through a pad of Celite®. The filtrate was concentrated under reduced pressure to give (±)-(4R*,5R*)-5-ethoxycarbonyl-1-methyl-4-(4-aminophenyl)pyrrolidin-2-one (1.66 g, 92%) as a pale oil: TLC (EtOAc) R$_f$0.48; HPLC ES-MS m/z (rel abundance) 263 (MH$^+$, 100%).

Intermediate V

Preparation of (±)-(4R*,5R*)-5-ethoxycarbonyl-1-methyl-4-(4-iodophenyl)pyrrolidin-2-one

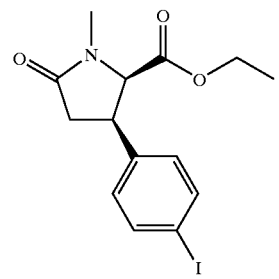

To a 0° C. solution of sodium nitrite (80 mg, 1.15 mmol) in sulfuric acid (2 mL) was added dropwise a solution of (±)-(4R*,5R)-5-ethoxycarbonyl-1-methyl-4-(4-aminophenyl)pyrrolidin-2-one (prepared according to the procedure for Intermediate U, 200 mg, 0.763 mmol) in glacial acetic acid (2 mL). The mixture was allowed to warm to room temperature and stirred for 40 min. The reaction was then cooled to 0° C. and a solution of potassium iodide (300 mg) and iodine (233 mg) in water (2 mL) was added in one portion. The dark mixture was stirred for 10 min at 0° C., followed by addition of enough aqueous solution of saturated sodium thiosulfate to lighten the reaction color. The mixture was then diluted with water (10 mL) and extracted with EtOAc. The combined organic layers were dried (MgSO$_4$) and concentrated under reduced pressure. The oily residue was purified by flash chromatography (gradient from 75% EtOAc/hex to 100% EtOAc) to give (±)-(4R*,5R*)-5- ethoxycarbonyl-1-methyl-4-(4-iodophenyl)pyrrolidin-2-one (125 mg, 44%) as a white powder: mp 120–121° C.; TLC (EtOAc) R$_f$ 0.59; HPLC ES-MS m/z (rel abundance) 374 (MH$^+$, 100%).

Intermediate W

Preparation of (±)-(4R*,5R*)-5-ethoxycarbonyl-1-methyl-4-(4-hydroxyphenyl)-pyrrolidin-2-one

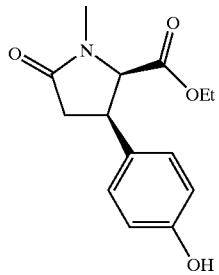

A 2° C. solution of (±)-(4R*,5R*)-5-ethoxycarbonyl-1-methyl-4-(4-aminophenyl)pyrrolidin-2-one (prepared according to the procedure for Intermediate U, 3.25 g, 12.4 mmol) in 42% aqueous HBF$_4$ (6 mL) and water (6 mL) was treated dropwise with a solution of NaNO$_2$ (856 mg, 12.4 mmol) in water (6 mL), keeping the reaction temperature below 10° C. The reaction mixture was stirred for 35 min, then poured in one portion into a 90° C. solution of H$_2$SO$_4$ (24 mL) in water (360 mL). The resulting solution was heated at 90° C. for 45 min, cooled to room temperature, diluted with ice (200 g) and extracted with CH$_2$Cl$_2$. The organic layer was dried (MgSo$_4$) and concentrated under reduced pressure to yield (±)-(4R*,5R*)-5-ethoxycarbonyl-1-methyl-4-(4-hydroxyphenyl)-pyrrolidin-2-one (2.90 g, 89%) as an orange oil: $^1$H NMR (DMSO-d$_6$) δ 0.76 (t, J=6.4 Hz, 3H), 2.41–2.67 (m, 5H), 3.59–3.87 (m, 3H), 4.38 (d, J=8.5 Hz, 1H), 6.63–6.68 (m, 2H), 6.97–7.02 (m, 2H), 9.30 (s, 1H).

Intermediate X

Preparation of (±)-(4R*,5R*)-5-ethoxycarbonyl-1-methyl-4-(4-methoxyphenyl)pyrrolidin-2-one

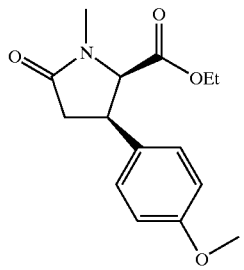

To a solution of (±)-(4R*,5R*)-5-ethoxycarbonyl-1-methyl-4-(4-hydroxyphenyl)pyrrolidin-2-one (prepared according to the procedure described for Intermediate W, 0.74 g, 2.81 mmol) in acetone (10 mL) was added Cs$_2$CO$_3$ (2.03 g, 5.62 mmol), followed by iodomethane (0.19 mL, 3.1 mmol). The reaction was stirred at room temperature for 72 h and filtered. The filtrate was concentrated under reduced pressure. The resulting oil was purified by flash chromatography (EtOAc) to yield (±)-(4R*,5R*)-5-ethoxycarbonyl-1-methyl-4-(4-methoxy-phenyl)pyrrolidin-2-one (0.72 g, 93%) as a white solid: $^1$H NMR (DMSO-d$_6$) δ 0.73 (t, J=6.0 Hz, 3H), 2.44–2.71 (m, 5H), 3.56–3.78 (m, 5H), 3.88 (q, J=8.8 Hz, 1H), 4.42 (d, J=8.8 Hz, 1H), 6.82–6.87 (m, 2H), 7.11–7.16 (m, 2H).

Intermediate Y

Preparation of (±)-(4R*,5R*)-5-ethoxycarbonyl-1-methyl-4-[4-(1,1,2,2-tetramethyl-1-silapropoxy)phenyl]pyrrolidin-2-one

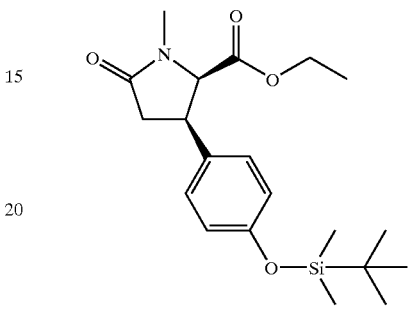

To a solution of (±)-(4R*,5R*)-5-ethoxycarbonyl-1-methyl-4-(4-hydroxyphenyl)pyrrolidin-2-one (Intermediate W, 0.400 g, 1.53 mmol) in anhyd. DMF (1.5 mL) was added imidazole (0.240 g, 3.05 mmol), followed by TBDMSCl (0.250 g, 1.68 mmol) and the mixture stirred at room temperature for 18 h. The resulting mixture was poured into a 0.5N HCl solution and extracted with EtOAc. The combined organic layers were dried (MgsO4) and concentrated under reduced pressure give a clear oil which was purified by flash chromatography (gradient from 67% to 100% EtOAc/hex) to yield (±)-(4R*,5R*)-5-ethoxycarbonyl-1-methyl-4-[4-(1,1,2,2-tetramethyl-1-silapropoxy)-phenyl)pyrrolidin-2-one (512 mg, 89%) as a light yellow oil: $^1$H NMR (DMSO-d$_6$) δ 0.13 (s, 6H), 0.75 (t, J=7.0 Hz, 3H), 0.91 (s, 9H), 0.24–0.70 (m, 5H), 3.55–3.76 (m, 2H), 3.88 (q, J=9.1 Hz, 1H), 4.43 (d, J=9.1 Hz, 1H), 6.75–6.79 (m, 2H), 7.07–7.13 (m, 2H).

Intermediate Z

Preparation of (4R*,5R*)-5-formyl-1-methyl-4-phenylpyrrolidin-2-one

Method 1:

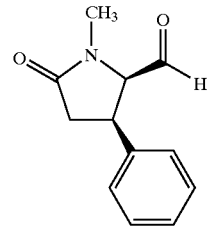

(±)-(4R*,5R*)-5-Formyl-1-methyl-4-phenylpyrrolidin-2-one was prepared substantially as reported in the literature (W. Hartwig and L. Born, *J. Org. Chem.*, 1987,52,4352 or Rudorf, W.-D., Schwarz, R. *Z. Chem.*, 1988,28, 101), as follows:

A cold (−76° C.), stirred solution of oxalyl chloride (0.8 mole) in dichloromethane (1.4 L) was treated with dimethyl sulfoxide (116 mL, 1.64 mole) over 40 minutes while keeping the internal temperature below −60° C. After stirring the solution for 45 minutes, a solution containing (−)-(4R*,5R*)-5-hydroxymethyl-1-methyl-4-phenylpyrrolidin-2-one (150 g, 0.73 mole) in dichloromethane (1L) was added over a 30 minute period (T<−60° C.) and stirring continued for 45 minutes. Hunig's base (diisopropylethylamine, 509 mL, 2.92 mole) was then added dropwise (T<−60° C.), the mixture was stirred for 45 minutes and then quenched with 1N hydrochloric acid solution (cold, 1.5L) while warming to 0° C. The layers were separated and the organic layer was washed twice with hydrochloric acid (700 mL of 2N, then 500 mL of 1N), dried over magnesium sulfate, filtered and concentrated in vacuo to give (−)-(4R*,5R*)-5-formyl-1-methyl-4-phenylpyrrolidin-2-one as tan, crystalline solids, 137 g (93%). NMR (CDCl$_3$) 67 2.81 (m, 2, CH$_2$), 2.91 (s,3H, CH$_3$) 4.02 (q, J=9 Hz, 1H, CH), 4.38 (dd, J=9.1, 1.9 Hz), 7.21–7.39 (m, 5H, Ar), 9.17 (d, J=1.9 Hz, 1H, CHO).

Method 2:

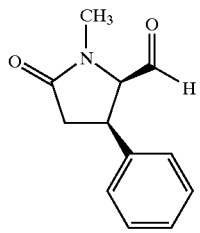

To a solution of (±)-(4R*,5R*)-5-(hydroxymethyl)-1-methyl-4-phenylpyrrolidin-2-one (prepared according to the procedure for Intermediate T, Method 2, 1.31 g, 6.38 mmol) in CH$_2$Cl$_2$ (14.50 mL) was added Dess-Martin Periodinane (3.26 g, 7.69 mmol). The resulting heterogeneous mixture was stirred for 45 minute, then treated with a 1:1 ratio of saturated Na$_2$S$_2$O$_3$ and NaHCO$_3$ solutions (30 mL) and extracted with Et$_2$O (3×50 mL). The organic layers were dried (MgSO$_4$) and concentrated under reduced pressure. The residue was dissolved in benzene and concentrated under reduced pressure. The resulting (±)-(4R*,5R*)-5-formyl-1-methyl-4-phenylpyrrolidin-2-one was dissolved in anhyd. THF (5.00 mL) and used without further purification: TLC (EtOAc) R$_f$ 0.31;

Intermediate AA

Preparation of (±)-(4R*,5R*)-5-(ethoxycarbonyl)-1-methyl-4-phenylpyrrolidin-2-one Step 1: Preparation of racemic ethyl 1-methyl-5-oxo-3-phenyl-3-pyrroline-2-carboxylate

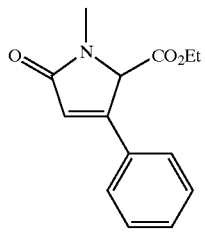

To a 0° C. solution of ethyl 2-(N-methyl-3-phenylprop-2-ynoylamino)acetate (prepared according to the procedure described for Intermediate A, 20 g, 82 mmol) in THF (100 mL) was added a solution of Li(SiMe$_3$)$_2$ (1M in THF, 82 mL, 82 mmol). The resulting mixture was stirred for 2 h, then was slowly treated with water (20 mL) and diluted with CH$_2$Cl$_2$ (200 mL). The organic layer was washed with water (150 mL), a 1N HCl solution (150 mL) and water (150 mL), dried (Na$_2$SO$_4$) and concentrated under reduced pressure. The crude product was purified by flash chromatography (gradient from 0% to 50% EtOAc/hex) to give racemic ethyl 1-methyl-5-oxo-3-phenyl-3-pyrroline-2-carboxylate (14 g, 70%) as a brown oil: TLC (40% EtOAc/hex) R$_f$ 0.13; $^1$H NMR (CDCl$_3$) δ 1.10 (t, J=7.4 Hz, 3H), 3.03 (s, 3H), 4.12 (m, 2H), 5.13 (s, 1H), 6.46 (s, 1H), 7.39–7.41 (m, 3H), 7.53–7.60 (m, 2H); HPLC ES-MS m/z (rel abundance) 246 (MH$^+$, 100%).

Step 2: Preparation of (±)-(4R*,5R*)-5-(ethoxycarbonyl)-1-methyl-4-phenylpyrrolidin-2-one

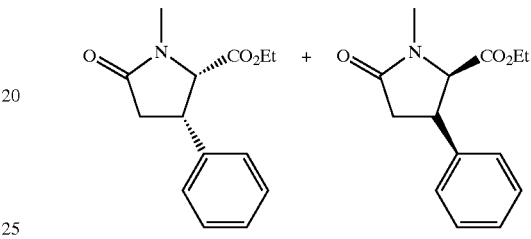

A mixture of ethyl 1-methyl-5-oxo-3-phenyl-3-pyrroline-2-carboxylate (1 g, 4 mmol) and 10% palladium on carbon (0.1 g) in EtOH (30 mL) was stirred under a H$_2$ atmosphere (1 Atm) for 1 hour. The reaction mixture was filtered through a pad of Celite® with the aid of CH$_2$Cl$_2$. The filtrate was concentrated under reduced pressure to yield (±)-(4R*,5R*)-5-(ethoxycarbonyl)-1-methyl-4-phenylpyrrolidin-2-one (1 g, 100%): TLC (40% EtOAc/hex) R$_f$ 0.13; $^1$H NMR (CDCl$_3$) δ 0.83 (t, J=7.4 Hz, 3H), 2.64–2.72 (dd, J=8.8, 16.5 Hz, 1H), 2.88–3.0 (m, 4H), 3.65–4.0 (m, 4H), 4.34–4.36 (d, J=8.9 Hz, 1H), 7.2–7.35 (m, 5H), HPLC ES-MS m/z (rel abundance) 248 (MH$^+$, 100%).

Intermediate BB

Preparation of (±)-(4R*,5R*)-5-{(1R*)3-(3-aminophenyl)-1-tert-butyldimethylsilyloxyprop-2-ynyl}-1-methyl-4-phenylpyrrolidin-2-one Step 1: Preparation of (±)-(4R*,5R*)-5-{(1R*)3-[3-(2,5-dimethylpyrrolyl)phenyl]-1-tert-butyldimethyl-silyloxyprop-2-ynyl}-1-methyl-4-phenylpyrrolidin-2-one

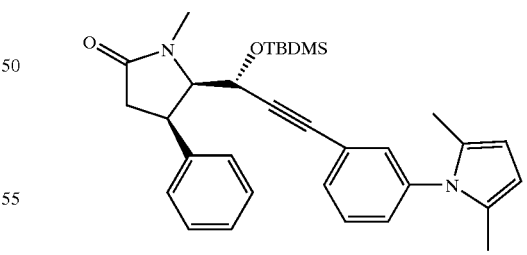

To a 0° C. solution of (±)-(4R*5R*)-5-{(1R*)-3-[3-(2,5-dimethylpyrrolyl)phenyl]-1-hydroxyprop-2-ynyl}-1-methyl-4-phenylpyrrolidin-2-one (prepared according to the procedure described for Example 8, 0.15 g, 0.37 mmol) and 2,6-lutidine (0.1 mL, 0.93 mmol) in CH$_2$Cl$_2$ (10 mL) was added TBDMSOTf (0.13 mL, 0.55 mmol). The reaction mixture was stirred for 2 h, allowed to warm to room temperature and treated with water. The resulting mixture was extracted with CH$_2$Cl$_2$, dried (Na$_2$SO$_4$) and concentrated under reduced pressure. The crude product was purified by flash chromatography (80% EtOAc/hex) to give (±)-(4R*,5R*)-5-{(1R*)3-[3-(2,5-dimethylpyrrolyl)phenyl]-1-tert-butyldimethyl-silyloxyprop-2-ynyl}-1-methyl-4-phenylpyrrolidin-2-one (90 mg, 47%): mp 156–158° C.; TLC (50% EtOAc/hex) $R_f$ 0.41.

Step 2: Preparation of (±)-(4R*,5R*)-5-{(1R*)3-(3-aminophenyl)-1-tert-butyldimethylsilyloxyprop-2-ynyl}-1-methyl-4-phenylpyrrolidin-2-one

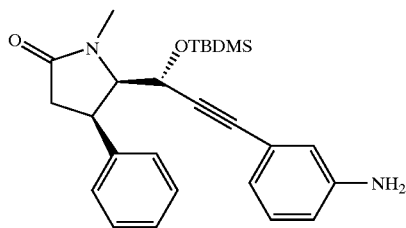

To a solution of (±)-(4R*,5R*)-5-{(1R*)3-[3-(2,5-dimethylpyrrolyl)phenyl]-(-1-tert-butyldimethylsilyloxyprop-2-ynyl}-1-methyl-4-phenylpyrrolidin-2-one (85 mg, 0.17 mmol) in EtOH (4 mL) was added a solution of KOH (0.2 g, 3.6 mmol) and $NH_2OH·HCl$ (0.34 g, 4.9 mmol) in water (1 mL). The reaction mixture was heated at the reflux temperature for 3 days, then was treated with a 1N NaOH solution. The resulting mixture was extracted with $CH_2Cl_2$. The organic layer was washed with a saturated NaCl solution, dried ($Na_2SO_4$) and concentrated under reduced pressure. The crude product was purified by preparatory TLC (80% EtOAc/hex) to give (±)-(4R*,5R*)-5-{(1R*)3-(3-aminophenyl)-1-tert-butyldimethylsilyloxyprop-2-ynyl}-1-methyl-4-phenylpyrrolidin-2-one (57 mg, 73%) as a yellow oil: TLC (80% EtOAc/hex) $R_f$ 0.65.

Intermediate CC

Preparation of (4S,5S)-4-(2-fluorophenyl)-5-(hydroxymethyl)-1-methylpyrrolidin-2-one Step 1: Preparation of 3-{[(2R)-3-(2-fluorophenyl)-1-methyl-5-oxo(3-pyrrolin-2-yl)]carbonyl}(4S)-4-benzyl-1,3-oxazolidin-2-one and (4S)-3-{[(2S)-3-(2-flourophenyl)-1-methyl-5-oxo(3-pyrrolin-2-yl)]carbonyl}-4-benzyl-1,3-oxazolidin-2-one

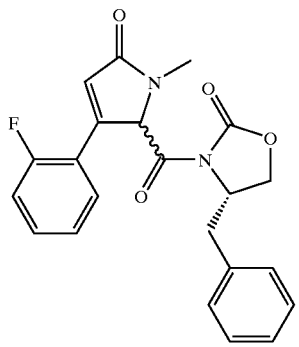

A solution of N-{2-[(4S)-2-oxo-4-benzyl(1,3-oxazolidin-3-yl)]-2-oxoethyl}-3-(2-fluorophenyl)-N-methylprop-2-ynamide (prepared according to the procedure for Intermediate R, 142 g, 0.36 mol) in DMSO (1 L) was placed in water bath and was slowly treated with a solution of KOtBu (42.5 g, 0.38 mol. 1.05 equiv) in DMSO (500 mL). Throughout the addition, which took 50 min, the reaction temperature rose from 20° C. to 29° C. and the orange solution turned deep red. The reaction mixture was stirred for 90 min, treated with a saturated $NH_4Cl$ solution (500 mL) and concentrated under reduced pressure. The residue was dissolved in EtOAc (2 L) and washed with water (1 L, then 3×500 mL). The aqueous layers were back-extracted with EtOAc (1 L). The organic layers were combined and washed with a saturated NaCl solution (2×500 mL), dried ($Na_2SO_4$) and concentrated under reduced pressure to afford a diastereomeric mixture of 3-{[(2R)-3-(2-fluorophenyl)-1-methyl-5-oxo(3-pyrrolin-2-yl)]carbonyl}(4S)-4-benzyl-1,3-oxazolidin-2-one and (4S)-3-{[(2S)-3-(2-fluorophenyl)-1-methyl-5-oxo(3-pyrrolin-2-yl)]carbonyl}-4-benzyl-1,3-oxazolidin-2-one (151 g, 100%) as a yellow solid: TLC (60% EtOAc/benzene) $R_f$ 0.66; partial $^1H$ NMR (CDCl$_3$) δ 2.28 (dd, J=10.3, 13.2 Hz, 0.57H), 2.77 (dd, J=10.1, 13.3 Hz, 0.43H), 3.02 (s, 1.71H), 3.06 (s, 1.29H), 4.55–4.63 (m, 0.43H), 4.66–4.74 (m, 0.57H); HPLC ES-MS m/z (rel abundance) 395 (MH$^+$, 75%).

Step 2: Preparation of (4S)-3-{[(2S,3S)-3-(2-fluorophenyl)-1-methyl-5-oxopyrrolidin-2-yl]carbonyl}-4-benzyl-1,3-oxazolidin-2-one and 3-{[(2R,3R)-3-(2-fluorophenyl)-1-methyl-5-oxopyrrolidin-2-yl]carbonyl}(4S)-4-benzyl-1,3-oxazolidin-2-one

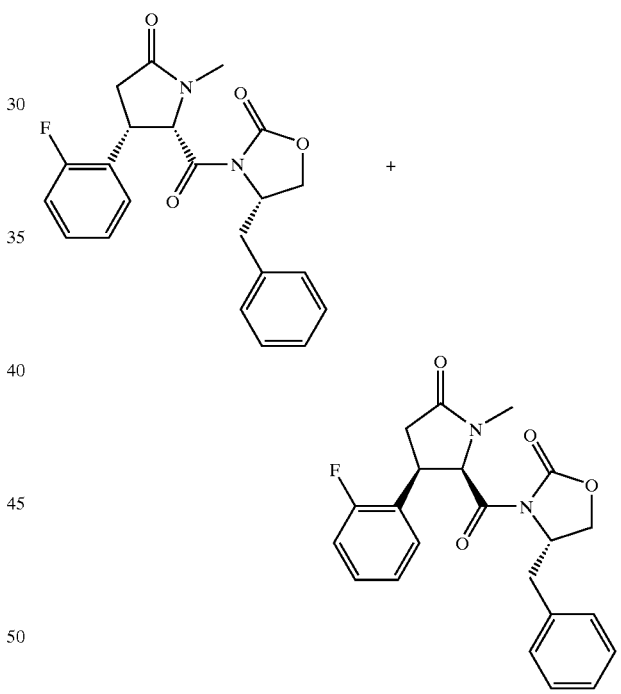

To a slurry of 20% palladium on carbon (10 g, 0.06 equiv) in EtOH (1 L) was added a solution of diastereomeric mixture of 3-{[(2R)-3-(2-fluorophenyl)-1-methyl-5-oxo(3-pyrrolin-2-yl)carbonyl(4S)-4-benzyl-1,3-oxazolidin-2-one and (4S)-3-{[(2S)-3-(2-fluorophenyl)-1-methyl-5-oxo(3-pyrrolin-2-yl)]carbonyl}-4-benzyl-1,3-oxazolidin-2-one (154 g, 0.36 mol) in EtOH (1 L) and the resulting mixture was vigorously stirred under a $H_2$ atmosphere (1 Atm) for 17 h. The reaction mixture was filtered through a pad of Celite®. NMR analysis of the filtrate showed only partial reduction, and the reaction mixture was treated with 10% palladium on carbon (Degussa type, 30 g, 0.1 equiv) in EtOH (4 L). After stirring under a $H_2$ atmosphere (1 Atm) for 17 h, the reaction mixture was filtered through a pad of Celite®. The filtrate was concentrated under reduced pressure onto silica gel (250 g), then filtered through a plug of silica gel eluting with EtOAc. The filtrate was concentrated under reduced pressure onto silica gel (400 g) and purified by flash chromatography (2.5 kg silica gel, gradient from 25% to 60% EtOAc/hex) to afford (4S)-3-{[(2S,3S)-3-(2-fluorophenyl)-1-methyl-5-oxopyrrolidin-2-yl]carbonyl}-4-benzyl-1,3-oxazolidin-2-one (48 g, 30%) as a yellow solid: TLC (50% EtOAc/hex) $R_f$ 0.22; $^1$H NMR (CDCl$_3$; rotomeric mixture) δ 2.63 (dd, J=4.9, 9.5 Hz, 1H), 2.74–2.85 (m, 4H), 3.07 (dd, J=3.4, 13.2 Hz, 1H), 3.34 (t, J=8.3 Hz, 1H), 3.84–4.09 (m, 3H), 4.27 (dd, J=9.6, 18.8 Hz, 1H), 5.77 (d, J=8.8 Hz, 1H), 6.95–7.26 (m, 10H); HPLC ESMS m/z (rel abundance) 397 (MH$^+$, 75%); and 3-{[(2R,3R)-3-(2-fluorophenyl)-1-methyl-5-oxopyrrolidin-2-yl]carbonyl} (4S)-4-benzyl-1,3-oxazolidin-2-one (48 g, 30%) as a yellow solid: TLC (50% EtOAc/hex) $R_f$ 0.13; $^1$H NMR (CDCl$_3$; rotomeric mixture) δ 1.63 (dd, J=11.2, 13.4 Hz, 1H), 2.64 (dd, J=2.8, 13.1 Hz, 1H), 2.75–2.93 (m, 5H), 3.95 (dd, J=3.4, 9.2 Hz, 1H), 4.09 (t, J=7.8 Hz, 1H), 4.40–4.50 (m, 2H), 5.77 (d, J=8.6 Hz, 1H), 7.04–7.12 (m, 4H), 7.21–7.32 (m, 5H); HPLC ES-MS m/z (rel abundance) 397 (MH$^+$, 90%); and a mixture of the two diastereomers (17 g, 11%).

Step 3: Preparation of (4S,5S)-4-(2-fluorophenyl)-5-(hydroxymethyl)-1-methylpyrrolidin-2-one

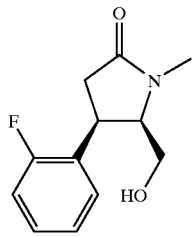

To a −78° C. solution of (4S)-3-{[(2S,3S)-3-(2-fluorophenyl)-1-methyl-5-oxopyrrolidin-2-yl]carbonyl}-4-benzyl-1,3-oxazolidin-2-one (1.0 g, 2.5 mmol) in anhyd. THF (30 mL) was added a solution of LiAlH$_4$ (1M in THF, 2.5 mL, 2.5 mmol, 1 equiv). After 2 h a solution of LiAlH4 (1M in THF, 0.5 mL, 0.5 mmol, 0.2 equiv) was added and after 30 min the reaction was treated with a saturated NH$_4$Cl solution (10 mL). The resulting mixture was allowed to warm to room temperature and filtered. The filtrate was concentrated under reduced pressure and purified by flash chromatography (50 g silica gel, gradient from 0% to 10% MeOH/EtOAc) to afford (4S,5S)-4-(2-fluorophenyl)-5-(hydroxymethyl)-1-methylpyrrolidin-2-one (340 mg, 61%) as a white solid: TLC (5% MeOH/EtOAc) $R_f$ 0.40; $^1$H NMR (CDCl$_3$) δ 2.41 (dd, J=8.4, 15.8 Hz, 1H), 2.94 (s, 3H), 3.03 (dd, J=11.6, 16.0 Hz, 1H), 3.21 (dd, J=2.2, 12.5 Hz, 1H), 3.53 (br s, 1H), 3.67 (dd, J=2.2, 12.5 Hz, 1H), 3.81–3.85 (m, 1H), 3.94–4.03 (m, 1H), 7.04 (t, J=9.0 Hz, 1H), 7.15 (t, J=7.5 Hz, 1H), 7.22–7.29 (m, 1H), 7.38 (t, J=7.5 Hz, 1H); HPLC ES-MS m/z (rel abundance) 224 (MH$^+$, 100%).

Alternatively, (4S,5S)-4-(2-fluorophenyl)-5-(hydroxymethyl)-1-methyl-pyrrolidin-2-one could be isolated from (±)-(4S*,5S*)-4-(2-fluorophenyl)-5-(hydroxymethyl)-1-methylpyrrolidin-2-one using the HPLC Separation D apparatus.

Intermediate DD

Preparation of 2-(2-fluoro-4-methylphenyl)-thiophene

To a mixture of magnesium (0.25 g, 10.58 mmol) in anhydrous THF (5.3 mL) was added 2-bromothiophene (1.73 g, 10.58 mmol) dropwise. The mixture was heated at reflux under argon for 0.5 h. An additional 0.35 g of 2-bromothiophene was added to consume the remaining magnesium. The reaction mixture was heated for additional 1.5 h to afford a solution which was transferred to a mixture of 1-bromo-2-fluoro-4-methylbenzene (2.0 g, 10.58 mmol), Pd(PPh$_3$)$_4$ (0.61 g, 0.53 mmol), and THF (23.5 mL). The resulting mixture was heated under argon for 3 h. The reaction was allowed to cool to rt and quenched with water. The mixture was extracted with CH$_2$Cl$_2$. The organic layer was dried over MgSO$_4$ and concentrated down under reduced pressure. The crude product was purified by flash column chromatography eluting with hexane to afford a colorless liquid (1.46 g, 72%): $^1$H NMR (CDCl$_3$), δ 7.48–7.02 (m, 6H), 2.36 (s, 3H), GC/MS m/z 192 (M$^+$, 100).

EXAMPLE 1

Preparation of (±)-(4R*,5R*)-5-((1S*)-hydroxy-2-thienylmethyl)-1-methyl-4-phenylpyrrolidin-2-thione

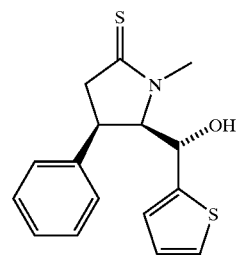

(±)-(4R*,5R*)-5-((1S*)-Hydroxy-2-thienylmethyl)-1-methyl-4-phenyl-pyrrolidin-2-one (Example 5, 0.30 g, 1.06 mmol) and Lawesson's Reagent ([2,4-bis(4-methoxyphenyl)-1,2-dithia-2,4-diphosphetane-2,4-disulfide; 0.22 g, 0.53 mmol) were mixed in DME (3 mL) at rt for 18 h then heated to 65° C. for another 18 h. The reaction was cooled to rt and the solvent was concentrated under reduced pressure to give a dark oil. The crude product was purified by flash chromatography (1% MeOH/99% CH$_2$Cl$_2$) to give (±)-(4R*,5R*)-5-((1S*)-hydroxy-2-thienylmethyl)-1-methyl-4-phenylpyrrolidin-2-thione (46 mg, 15% yield) as a yellow solid; TLC (75% EtOAc/25% hexanes) $R_f$ 0.36; HPLC ES-MZ m/z (rel abundance) 304 ([MH]$^+$, 100%) AT 4.8 min.

EXAMPLE 2

Preparation of (±)-(4R*,5R*)-5-[(3-chlorophenoxy)methyl]-1-methyl-4-phenylpyrrolidin-2-one

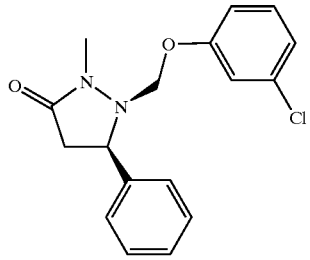

To a solution of (±)-(4R*,5R*)-5-(hydroxymethyl)-1-methyl-4-phenylpyrrolidin-2-one (Intermediate T prepared by Method 2, 220 mg, 1.1 mmol), PPh$_3$ (422 mg, 1.6 mmol) and 3-chlorophenol (0.13 mL, 1.6 mmol) in THF (10 mL) was added DIAD (0.31 mL, 1.6 mmol). The reaction mixture was stirred overnight, then concentrated under reduced pressure and purified by flash chromatography (30% EtOAc/CH$_2$Cl$_2$) to afford (±)-(4R*,5R*)-5-[(3-chlorophenoxy)methyl]-1-methyl-4-phenylpyrrolidin-2-one (80 mg, 23%) as a colorless oil. TLC (75% EtoAc/25% hexanes) R$_f$ 0.29, CI m/z (rel abundance) 316 ([MH]$^+$, 100%).

EXAMPLE 3a

Preparation of (±)-(4R*,5R*)-5–1(1S*)[5-(4-fluorophenyl)(2-thienyl)]hydroxymethyl}-1-methyl-4-phenylpyrrolidin-2-one

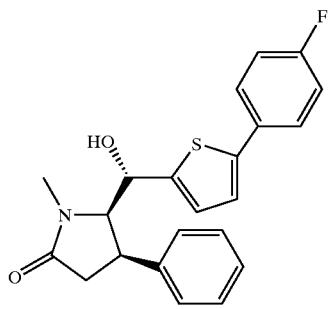

To a −65° C. solution of 2-(4-fluorophenyl)thiophene (Intermediate O; 853.6 mg, 5.79 mmol) in THF (5 mL) was added a solution of n-BuLi (2.5M in hexane, 1.8 mL, 4.5 mmol). The reaction mixture was allowed to warm to −20° C. over the period of 1 h. After cooling down to −65° C. again, a solution of (±)-(4R*,5R*)-5-formyl-1-methyl-4-phenylpyrrolidin-2-one (Intermediate Z, 6.38 mmol) in THF (5 mL) was added. The reaction mixture was stirred for 1 h, while allowing to warm to −20° C., then treated with a saturated NH$_4$Cl solution (15 mL). The resulting mixture was extracted with EtOAc (4×15 mL), dried (MgSO$_4$) and concentrated under reduced pressure. The crude brown solid was triturated (Et$_2$O/hex) to give (±)-(4R*,5R*)-5-{(1S*)[5-(4-fluorophenyl)(2-thienyl)]hydroxymethyl}-1-methyl-4-phenylpyrrolidin-2-one (330 mg, 24%) as a fine brown solid: mp 110° C. (dec); TLC (EtOAc) R$_f$ 0.52.

EXAMPLE 3b

Preparation of (4R*,5R*)-5–1(1S)-hydroxy[5-(3-pyridinyl)-2-thienyl]methyl}-1-methyl-4-phenyl-2-pyrrolidinone

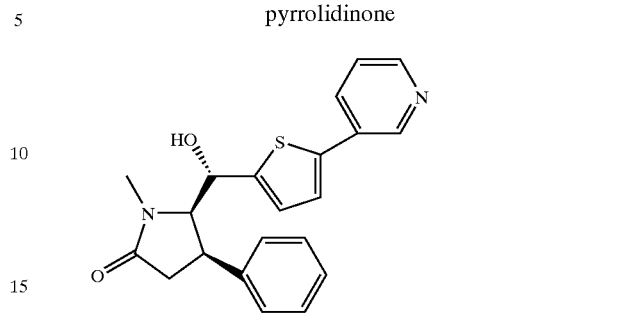

A stirred solution containing 2-(3-pyridyl)thiophene (87.1 g, 0.54 moles) in anhydrous THF (1L) was cooled to −76° C. and n-butyllithium (1.6M in hexanes, 338 mL, 0.54 moles) was added dropwise, maintaining an internal temperature below −60° C. After stirring the mixture for 0.5 h at −76° C. tetramethylethylenediamine (163 mL, 1.08 moles) was added dropwise and stirring was continued for 0.5 h. A solution containing (−)-(4R*,5R*)-5-formyl-1-methyl-4-phenylpyrrolidin-2-one (Intermediate Z, 100 g, 0.49 moles) in THF (0.5 L) was then added dropwise and the mixture was allowed to react for 1 h at −76° C. The reaction was quenched with saturated ammonium chloride solution (1L) and water (1L), then ethyl acetate (2L) was added and the mixture was vigorously stirred overnight. The precipitated solids were filtered, washed with water (2×500 mL) and ethyl acetate (2×500 mL). The product was dried overnight under high vacuum (45° C.) to give 119 g (66%) of light tan solids, mp 232–232° C. NMR (DMSO-d$_6$) δ 2.27 (m, 1H, CH$_2$), 2.48 (s, 3H, CH$_3$), 2.99 (dd, J=12.4, 15 Hz, 1H, CH$_2$), 3.84 (dt, J=12, 8.1 Hz 1H, CH), 4.21 (dd, J=8, 1.8 Hz, 1H, CH), 4.46 (br s, 1H, CH), 6.05 (d, 1H, OH), 6.92 (dd, J=4, 1.1 Hz, 1H, CH), 7.25 (m, 1H, CH), 7.37(m, 5H, Ar), 7.47 (d, J=3.6 Hz, 1H, CH), 7.95 (m, 1H, CH), 8.43 (dd, J=4.9, 1.5 Hz, 1H, CH), 8.81 (d, 2 Hz, 1H, CH); MS (EI): m/z 365.2 (MH+).

EXAMPLE 4

Preparation of (±)-5-[(1S*)(5-(N-phenylcarbamoyl)(2-thienyl))hydroxymethyl](4R*,5R*)-1-methyl-4-phenylpyrrolidin-2-one Step 1: Preparation of (±)-(4R*,5R*)-5-[(1S*)(5-bromo(2-thienyl))hydroxymethyl]-1-methyl-4-phenyl-pyrrolidin-2-one

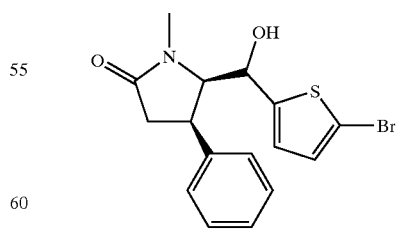

To a −78° C. solution of 2,5-dibromothiophene (7.2 g, 29.6 mmol, 1.02 equiv) in anhyd. THF (100 mL) was added dropwise a solution of n-BuLi (1.6M in hexane, 18.5 mL, 29.6 mmol, 1.02 equiv) keeping the reaction temperature below −70° C. The resulting brown solution was stirred for 2.5 h. A solution of (±)-(4R*,5R*)-5-formyl-1-methyl-4-phenylpyrrolidin-2-one (Intermediate Z, 5.9 g, 29.1 mmol) in benzene (30 mL) was added, keeping the reaction temperature below −70° C. The reaction mixture was diluted with THF (30 mL) and after 30 min was treated with a saturated NH$_4$Cl solution (150 mL). The resulting mixture was extracted with EtOAc (200 mL) and CH$_2$Cl$_2$ (2×200 mL) and dried (Na$_2$SO$_4$). The combined organic layers were concentrated under reduced pressure. The crude product was triturated (MeOH) to give (±)-(4R*,5R*)-5-[(1S*)(5-bromo(2-thienyl))hydroxymethyl]-1-methyl-4-phenyl-pyrrolidin-2-one (6.2 g) as a white solid. The filtrate was treated with silica gel (15 g), concentrated under reduced pressure and purified by flash chromatography to afford an additional 0.92 g of product (total 7.12 g, 67%) as an off-white solid: TLC (60% EtOAc/hex) R$_f$ 0.39; $^1$H NMR (CDCl$_3$) δ 2.24 (dd, J=6.2, 15.1 Hz, 1H), 2.42 (s, 3H), 2.95 (t, J=13.8 Hz, 1H), 3.76–3.85 (m, 1H), 4.15 (d, J=8.0 Hz, 1H), 4.36 (d, J=4.5 Hz, 1H), 6.06 (d, J=5.6 Hz, 1H), 6.70–7.15 (m, 1H), 7.02 (dd, J=1.9, 4.0 Hz, 1H), 7.22–7.44 (m, 5H).

Step 2: Preparation of (±)-5-[(1S*)(5-(N-phenylcarbamoyl)(2-thienyl))hydroxymethyl](4R*,5R*)-1-methyl-4-phenylpyrrolidin-2-one

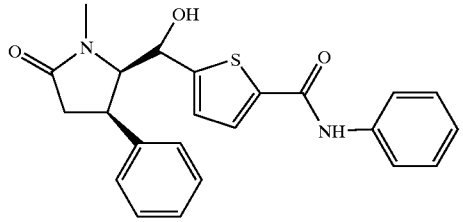

To a solution of (4R*,5R*)-5-[(1S*)(5-bromo(2-thienyl))hydroxymethyl]-1-methyl-4-phenylpyrrolidin-2-one (200 mg, 0.55 mmol) in DMSO (20 mL) was added Et$_3$N (166 mg, 1.64 mmol, 3 equiv), followed by dppf (23 mg, 0.05 mmol, 0.1 equiv), aniline (508 mg, 5.5 mmol, 10 equiv) and palladium(II) acetate (12 mg, 0.05 mmol, 0.1 equiv). The reaction mixture was heated to 80° C. under a CO atmosphere (1 Atm) overnight. The resulting mixture was treated with water (100 mL) and extracted with CH$_2$Cl$_2$ (100 mL). The organic layer was washed with a 1N HCl solution (100 mL) and a saturated NaCl solution (100 mL), dried (Na$_2$SO$_4$) and concentrated under reduced pressure. The residue was triturated (CH$_2$Cl$_2$) to give (±)-5-[(1S*)(5-(N-phenylcarbamoyl)(2-thienyl))hydroxymethyl](4R*,5R*)-1-methyl-4-phenylpyrrolidin-2-one (41 mg, 18%) as a white solid: mp 223–227° C.; TLC (80% EtOAc/hex) R$_f$ 0.26; HPLC ES-MS m/z (rel abundance) 407 (MH$^+$, 100%).

EXAMPLE 5

Preparation of (±)-(4R*,5R*)-5-{(1S*)[5-(3-chloro-4-fluorophenyl)(2-thienyl)]hydroxymethyl}-1-methyl-4-phenylpyrrolidin-2-one Step 1: preparation of (±)-(4R*,5R*)-5-((1S*)-hydroxy-2-thienylmethyl)-1-methyl-4-phenylpyrrolidin-2-one

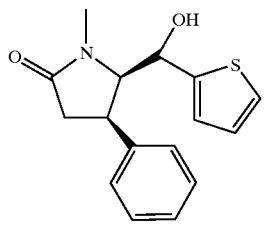

To a −50° C. solution of lithium thiophene (1M in THF, 170 mL, 170 mmol) was added a solution of (±)-(4R*,5R*)-5-formyl-1-methyl-4-phenylpyrrolidin-2-one (Intermediate Z, 127 mmol) in THF (10 mL). The reaction mixture was allowed to warm to 0° C. over 45 min and treated with a saturated NH$_4$Cl solution. The resulting mixture was extracted with EtOAc, dried (MgSO$_4$) and concentrated under reduced pressure. The crude product was purified by flash chromatography (67% EtOAc/hex) to give (±)-(4R*,5R*)-5-((1S*)-hydroxy-2-thienylmethyl)-1-methyl-4-phenylpyrrolidin-2-one (9.76 g, 27%): TLC (EtOAc) R$_f$ 0.42.

Step 2: preparation of (±)-(4R*,5R*)-5-[(1S*)(5-bromo(2-thienyl))hydroxymethyl]-1-methyl-4-phenylpyrrolidin-2-one

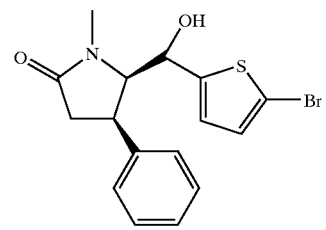

To 0° C. solution of (±)-(4R*,5R*)-5-((1S*)-hydroxy-2-thienylmethyl)-1-methyl-4-phenylpyrrolidin-2-one (9.76 g, 34 mmol) in AcOH (246 mL) was added bromine (2 mL 38.8 mmol). The reaction mixture was allowed to warm to room temperature, stirred for 2 h, then poured into water (500 mL). The resulting mustard colored precipitate was isolated via filtration and washed with water to yield (±)-(4R*,5R*)-5-[(1S*)(5-bromo(2-thienyl))hydroxymethyl]-1-methyl-4-phenylpyrrolidin-2-one (6.47 g, 52%): mp 105° C.; TLC (EtOAc) R$_f$ 0.48.

Step 3: Preparation of (±)-(4R*,5R*)-5-{(1S*)[5-(3-chloro-4-fluorophenyl)(2-thienyl)]hydroxymethyl}-1-methyl-4-phenylpyrrolidin-2-one

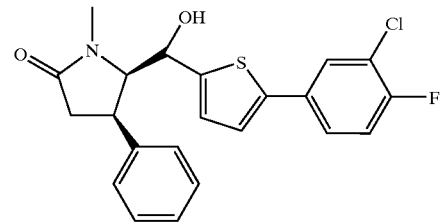

To a solution of (±)-(4R*,5R*)-5-[(1S*)(5-bromo(2-thienyl))hydroxymethyl]-1-methyl-4-phenylpyrrolidin-2-one (300 mg, 0.82 mmol) in 1,2-dimethoxyethane (2.8 mL) was added 3-chloro-4-fluorobenzeneboronic acid (85.9 mg, 1.07 mmol), followed by a 1M Na$_2$CO$_3$ solution (2.2 mL). A catalytic amount of Pd(PPh$_3$)$_4$ was added and the reaction mixture was heated at the reflux temperature for 3 h, then allowed to cool to room temperature and poured onto a mixture of ice and CH$_2$Cl$_2$. The resulting mixture was extracted with CH$_2$Cl$_2$, dried (MgSO$_4$) and concentrated under reduced pressure. The crude product was triturated (Et$_2$O/ cyclohexane) to give (±)-(4R*,5R*)-5-{(1S*)[5-(3-chloro-4-fluorophenyl)(2-thienyl)]hydroxymethyl}-1-methyl-4-phenylpyrrolidin-2-one (235 mg, 69%): mp 194° C.; TLC (EtOAc) R$_f$ 0.47

EXAMPLE 6

Preparation of (±)-(4R*,5R*)-5-[(1S*)-hydroxy(5-methyl(2-thienyl))methyl]-1-methyl-4-phenylpyrrolidin-2-one

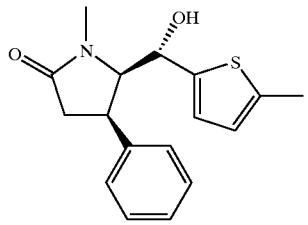

The synthesis was performed using literature method (Hartwig et al. *J. Org. Chem.* 1987,52,4352).

A portion (1 mL) of a solution of 2-bromo-5-methylthiophene (0.56 mL, 5.5 mmol) in THF (20 mL) was added to Mg turnings (135 mg, 5.5 mmol). The mixture was gently heated until the magnesium started to be consumed. The remaining thiophene solution was added in 1 mL increments to maintain a constant gentle reflux. After the addition was complete, the solution was heated at the reflux temperature for 3 min, then was allowed to cool to room temperature. To a −78° C. solution of (±)-(4R*,5R*)-5-formyl-1-methyl-4-phenylpyrrolidin-2-one (Intermediate Z, 190 mg, 1 mmol) in THF (7.5 mL) was slowly added the freshly prepared Grignard reagent and the reaction mixture was allowed to warm to room temperature. After 2 h a saturated $NH_4Cl$ solution was added and the mixture was extracted with EtOAc, dried ($MgSO_4$) and concentrated under reduced pressure. The residue was purified by flash chromatography (100% EtOAc) to give (±)-(4R*,5R*)-5-[(1S*)-hydroxy(5-methyl(2-thienyl))methyl]-1-methyl-4-phenylpyrrolidin-2-one (156 mg, 52%) as a white powder: mp 185–188° C.

EXAMPLE 7

Preparation of (±)-(4R*,5R*)-5-[(1R*)hydroxy(3-methylphenyl)methyl]-1-methyl-4-phenylpyrrolidin-2-one

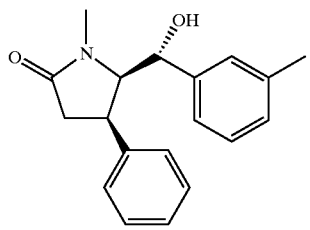

To a 0° C. solution of (±)-(4R*,5R*)-5-formyl-1-methyl-4-phenylpyrrolidin-2-one (Intermediate Z, 74 mg, 0.4 mmol) in anhyd. THF (5 mL) was added a solution of m-tolyl magnesium chloride (1M in THF, 0.5 mL, 0.5 mmol, 1.25 equiv). The reaction mixture was stirred for 1 h, then treated with a saturated $NH_4Cl$ solution and water. The resulting mixture was extracted with EtOAc, dried ($Na_2SO_4$) and concentrated under reduced pressure. The residue was triturated ($Et_2O$/hex) to give (±)-(4R*,5R*)-5-[(1R*) hydroxy(3-methylphenyl)methyl]-1-methyl-4-phenylpyrrolidin-2-one (82 mg, 77%): mp 163–165° C.; TLC (EtOAc) $R_f$ 0.45.

EXAMPLE 8

Synthesis of (±)-5-((1R*)-1-hydroxy-3-phenylprop-2-ynyl)(4R*,5R*)-1-methyl-4-phenylpyrrolidin-2-one

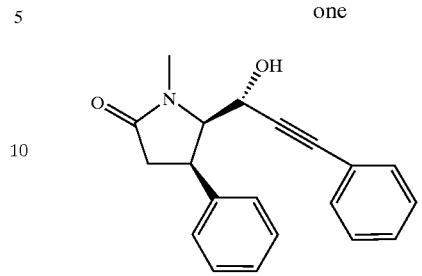

To a −20° C. solution of phenylacetylene (0.29 mL, 2.69 mmol) in anhyd. THF (1 mL) was added a solution of n-BuLi (1.6M in hexane, 1.56 mL, 2.50 mmol). The reaction mixture was stirred for 2 h at −20° C., then was cooled to −78° C. A solution of (±)-(4R*,5R*)-5-formyl-1-methyl-4-phenylpyrrolidin-2-one (Intermediate Z, 389 mg, 1.92 mmol) in THF (2 mL) was added dropwise. The reaction mixture was allowed to warm to room temperature, stirred for 18 h, then treated with a saturated $NH_4Cl$ solution and extracted with $CH_2Cl_2$. The combined organic layers were washed with a saturated NaCl solution, dried ($Na_2SO_4$) and concentrated under reduced pressure. The crude product was purified by flash chromatography (90% EtOAc/hex) to give (±)-(4R*,5R*)-5-((1R*)-1-hydroxy-3-phenylprop-2-ynyl)-1-methyl-4-phenyl-pyrrolidin-2-one (230 mg, 40%) as a white solid: mp 152–153° C.; $^1$H NMR ($CDCl_3$) δ 2.78–3.09 (m, 5H), 4.02 (q, J=9.0 Hz, 1H), 4.38 (dd, J=9.0 Hz, 2.0 Hz, 1H), 7.22–7.40 (m, 10H), 9.18 (d,J=2.0 Hz, 1H).

EXAMPLE 9

Preparation of (±)-(4R*,5R*)-5-[(1R*)-2-(3-chlorophenyt)-1-hydroxyethyl]-1-methyl-4-phenylpyrrolidin-2-one

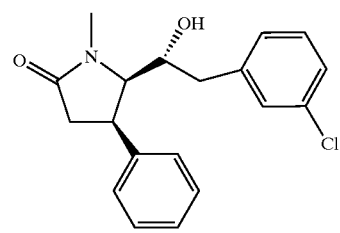

A portion of a mixture of 3-chlorobenzyl bromide (0.53 mL, 4.0 mmol) and $Et_2O$ (0.5 mL) was added to Mg turnings and $I_2$ (catalytic amount) in $Et_2O$ (4 mL). Once the reaction was initiated, the rest of the 3-chlorobenzyl bromide was added. When the reaction subsided, the resulting green mixture was transferred into a −78° C. suspension of $CeCl_3$ (1.05 g, 4.3 mmol) in THF (4 mL). A solution of the (±)-(4R*,5R*)-5-formyl-1-methyl-4-phenylpyrrolidin-2-one (Intermediate Z, 1M in THF, 3 mL, 3 mmol) was added and the reaction mixture was allowed to warm to room temperature, then was treated with a saturated $NH_4Cl$ solution and extracted with EtOAc. The combined organic layers were washed with water and a saturated NaCl solution, dried ($Na_2SO_4$) and concentrated under reduced pressure. The crude green oil was purified by flash chromatography (EtOAc) to give (±)-(4R*,5R*)-5-[(1R*)-2-(3- chlorophenyl)-1-hydroxyethyl]-1-methyl-4-phenylpyrrolidin-2-one (340 mg, 34%): mp 50–52° C.; TLC (EtOAc) R$_f$ 0.25.

EXAMPLE 10

Preparation of (±)-(4R*,5R*)-5-(indol-2-ylmethylthiomethyl)-1-methyl-4-phenylpyrrolidin-2-one

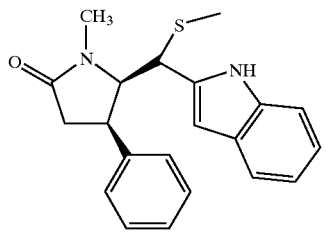

To a −60° C. mixture of DMSO (1.4 mL, 15.8 mmol) and CH$_2$Cl$_2$ (8 mL) was added a solution of trifluoroacetic anhydride (1.7 mL, 11.8 mL) in CH$_2$Cl$_2$ (3.2 mL) while the temperature rose to −40° C. A solution of (±)-(4R*,5R*)-5-(hydroxymethyl)-1-methyl-4-phenylpyrrolidin-2-one (Intermediate T, Method 2, 1.62 g, 7.9 mmol) in CH$_2$Cl$_2$ (7.9 mL) was added dropwise, keeping the reaction temperature below −60° C. The resulting mixture was allowed to warm to −30° C., stirred for 10 min, then cooled back to −60° C. Triethylamine (3.2 mL, 22.6 mmol) was added and the reaction mixture was stirred for 30 min, then allowed to warm to room temperature and treated with water. The aqueous layer was extracted with CH$_2$Cl$_2$. The organic layer was washed with water, dried (MgSO$_4$) and concentrated under reduced pressure to give a crude oil, which was stored as a THF solution and used without further purification.

To a −78° C. solution of tert-butyl N-indolecarboxylate (0.86 g, 3.95 mmol) in THF (4 mL) was added dropwise a solution of tert-BuLi (1.5M in THF, 2.6 mL, 3.95 mmol) and the reaction mixture was stirred for 2.5 h. To this was added a solution of the crude oil in THF (4 mL) and the reaction mixture was stirred for 1 h, then treated with a saturated NH$_4$Cl solution. The resulting mixture was extracted with CH$_2$Cl$_2$, concentrated under reduced pressure and purified by flash chromatography (gradient from 30% EtOAc/hex to 100% EtOAc) to afford (±)-(4R*,5R*)-5-(indol-2-ylmethylthiomethyl)-1-methyl-4-phenylpyrrolidin-2-one (17 mg, 1%) as a white solid: TLC (EtOAc) R$_f$ 0.67; HPLC ES-MS m/z 350 (M$^+$).

EXAMPLE 11

Preparation of (4R,5R)-5-[(1R)-hydroxy(5-phenyl(2-thienyl))methyl]-1-methyl-4-phenylpyrrolidin-2-one Step 1: Preparation of (4R,5R)-1-methyl-4-phenyl-5-[(5-phenyl(2-thienyl))carbonyl]pyrrolidin-2-one

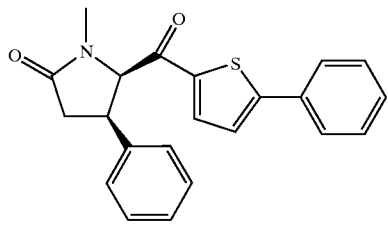

(4R,5R)-5-[(1S)-Hydroxy(5-phenyl(2-thienyl))methyl]-1-methyl-4-phenyl-pyrrolidin-2-one was prepared from Intermediate Z and 2-bromo-5-phenylthiophene by a method analogous to that described for Example 6, then separated using the HPLC Separation B apparatus.

To a suspension of this compound (84 mg, 0.23 mmol) in CH$_3$CN (3 mL) was then added Dess-Martin periodinane (117 mg, 276 mmol). The reaction mixture was heated at 55° C. for 1.5 h, allowed to cool to room temperature and treated with a 1:1 mixture of saturated NaHCO$_3$ and Na$_2$S$_2$O$_3$ solutions (10 mL). The resulting mixture was diluted with EtOAc, concentrated under reduced pressure onto silica gel and purified by flash chromatography (EtOAc) to give (4R,5R)-1-methyl-4-phenyl-5-[(5-phenyl(2-thienyl))carbonyl]pyrrolidin-2-one (62 mg, 75%): TLC (EtOAc) R$_f$ 0.23.

Step 2: Preparation of (4R,5R)-5-[(1R)-hydroxy(5-phenyl(2-thienyl))methyl]-1-methyl-4-phenylpyrrolidin-2-one

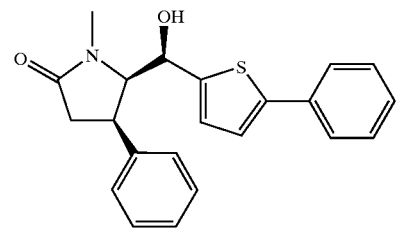

To a solution of (4R,5R)-1-methyl-4-phenyl-5-[(5-phenyl(2-thienyl))-carbonyl]pyrrolidin-2-one (60 mg, 0.17 mmol) in THF (2 mL) was added a solution of LiBH$_4$ (2M in THF, 0.1 mL, 0.2 mmol) and the reaction mixture was heated at 50° C. for 2 h. The resulting pale yellow suspension was treated with water and a saturated NH$_4$Cl solution, extracted with EtOAc, dried (Na$_2$SO$_4$), concentrated onto silica gel and purified by flash chromatography to give (4R,5R)-5-[(1R)-hydroxy(5-phenyl(2-thienyl))methyl]-1-methyl-4-phenylpyrrolidin-2-one (43 mg, 71%) as a yellow solid: TLC (EtOAc) R$_f$ 0.36; HPLC ES-MS m/z 364 (MH$^+$).

EXAMPLE 12

Preparation of (±)-(4R*,5R*)-5-((1S*)-methoxy-2-thienylmethyl)-1-methyl-4-phenylpyrrolidin-2-one

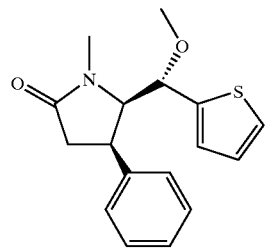

To a slurry of NaH (60%, 32 mg, 1.0 mmol) in DMF (15 mL) was added (±)-(4R*,5R*)-5-((1S)-hydroxy-2-thienylmethyl)-1-methyl-4-phenylpyrrolidin-2-one (Example 5 step 1, 250 mg, 0.9 mmol). The resulting mixture was stirred for 30 min, then methyl iodide (0.08 mL, 1.3 mmol) was added. After 2 h water was added and the resulting mixture was extracted with EtOAc, dried (MgSO$_4$) and concentrated under reduced pressure. The residue was purified by flash chromatography (EtOAc) to give (±)-(4R*,5R*)-5-((1S*)-methoxy-2-thienylmethyl)-1-methyl-4-phenylpyrrolidin-2-one (125 mg, 46%) as a white solid: mp 101–102° C.; TLC (EtOAc/hex) R$_f$ 0.50.

EXAMPLE 13

Preparation of (±)-(4R*,5R*)-5-1(1S*)[5-(4-fluorophenyl)(2-thienyl)]-acetyloxymethyl}-1-methyl4-phenylpyrrolidin-2-one

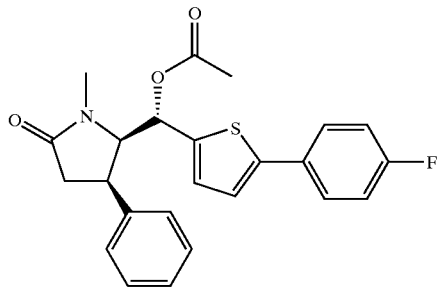

To a mixture of (±)-(4R*5R*)-5-{(1S*)[5-(4-fluorophenyl)(2-thienyl)]hydroxymethyl}-1-methyl-4-phenylpyrrolidin-2-one (Example 3a, 0.05 g, 0.131 mmol), pyridine (0.5 mL, 0.25 mmol) and DMAP (1.6 mg, 0.0131 mmol) was added Ac₂O (20 μL, 0.2 mmol) and the reaction mixture was stirred at room temperature for 17 h. The resulting mixture was diluted with EtOAc (20 mL), washed with a 10% HCl solution (10 mL), dried (MgSO₄) and concentrated under reduced pressure. The crude product was purified by flash chromatography (67% EtOAc/hex) to give (±)-(4R*,5R*)5-{(1S*)[5-(4-fluorophenyl)(2-thienyl)]acetyloxymethyl}-1-methyl4-phenylpyrrolidin-2-one (0.045g, 80%): mp 75° C.; TLC (CH₂Cl₂) $R_f$ 0.25.

EXAMPLE 14

Preparation of (±)-(4R*,5R*)-5-((1R*)-fluoro-2-thienylmethyl)-1-methyl-4-phenylpyrrolidin-2-one and (±)-(4R*,5R*)-5-((1S*)-fluoro-2-thienylmethyl)-1-methyl-4-phenylpyrrolidin-2-one

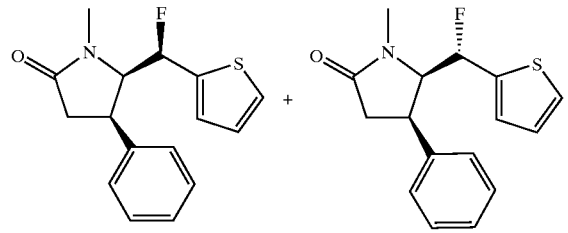

To a slurry of (±)-4R*,5R*)-5-((1S*)-hydroxy-2-thienylmethyl)-1-methyl-4-phenylpyrrolidin-2-one (Example 5 step 1, 0.14 g, 0.49 mmol) in CH₂Cl₂ (10 mL) was added DAST (0.13 mL, 0.98 mmol). The reaction mixture was stirred overnight, then treated with a saturated NH₄Cl solution and extracted with CH₂Cl₂ and concentrated under reduced pressure. The crude product was purified by flash chromatography (80% EtOAc/hex) to give a 5:1 diastereomeric mixture of (±)-(4R*,5R*)-5-((1R*)-fluoro-2-thienylmethyl)-1-methyl-4-phenylpyrrolidin-2-one and (±)-(4R*,5R*)-5-((1S*)-fluoro-2-thienylmethyl)-1-methyl-4-phenylpyrrolidin-2-one (92 mg, 65%): TLC (EtOAc) $R_f$ 0.55; ¹H NMR (CDCl₃) δ 2.66 (dd, J=14.4, 8.4 Hz, 1H), 2.81–2.96 (m, 4H), 3.72 (q, J=8.4 Hz, 1H), 4.14–4.25 (m, 1H), 5.29–5.32 (d, J=5.4 Hz, 0.85H), 5.39 (d, J=2.5 Hz, 0.15H), 5.47 (d, J=4.7 Hz, 0.85H), 5.54 (d, J=2.5 Hz, 0.15H), 6.67–6.68 (m, 1H), 6.89–6.91 (m, 1H), 7.06–7.13 (m, 2H), 7.25–7.34 (m, 4H).

EXAMPLE 15

Preparation of (±)-(4R*,5R*)-5-1(2E)1R*)-3-(4-fluorophenyl)-1-hydroxyprop-2-enyl]-1-methyl-4-phenylpyrrolidin-2-one Step 1: preparation of (±)-(4R*,5R*)-5-[(2Z)(1R*)-3-(4-fluorophenyl)-1-hydroxyprop-2-enyl]-1-methyl-4-phenylpyrrolidin-2-one

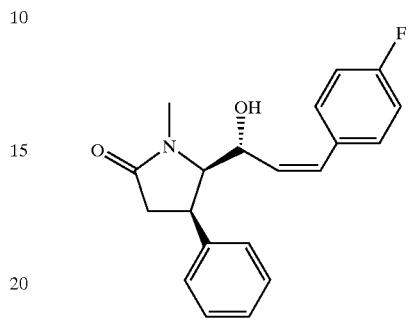

(±)-(4R*,5R*)-5-[(1R*)-3-(4-Fluorophenyl)-1-hydroxyprop-2-ynyl]-1-methyl-4-phenylpyrrolidin-2-one was prepared from 4-fluorophenylacetylene and Intermediate Z using a method analogous to that described for Example 8. To a 300 mg (0.93 mmol)slurry of this compound in hexanes (60 mL) was added Pd on CaCO₃ (80 Mg), followed by pyridine (0.23 mL, 2.8 mmol). The reaction mixture was stir-red overnight, then filtered through a pad of Celite®. The filtrate was concentrated under reduced pressure to give (±)-(4R*,5R*)-5-[(2Z)(1R*)-3-(4-fluorophenyl)-1-hydroxyprop-2-enyl]-1-methyl-4-phenylpyrrolidin-2-one (302 mg, 100%) as a white solid: mp 163–165° C.; ¹H NMR (CD₃OD) δ 2.36 (dd, J=15.8, 7.8 Hz, 1H), 3.01–3.17 (m, 4H), 3.80–3.90 (m, 2H), 4.33 (d, J=8.7 Hz, 1H), 5.74 (dd, J=11.6, 8.8 Hz, 1H), 6.34 (d, J=11.6 Hz, 1H), 6.85–6.97 (m, 4H), 7.18–7.36 (m, 5H).

Step 2: Preparation of (±)-(4R*,5R*)-5-[(2E)(1R*)-3-(4-flourophenyl)-1-hydroxyprop-2-enyl]-1-methyl-4-phenylpyrrolidin-2-one

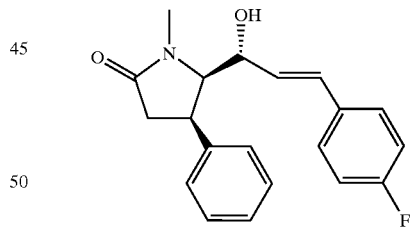

A mixture of (±)-5-[(2Z)(1R*)-3-(4-fluorophenyl)-1-hydroxyprop-2-enyl](4R*,5R*)-1-methyl-4-phenylpyrrolidin-2-one (115 mg, 0.35 mmol), AIBN (10 mg, 0.06 mmol) and thiophenol (12 mg, 0.11 mmol) in benzene (10 mL) was heated at the reflux temperature for 4 h. The resulting mixture was concentrated under reduced pressure and purified by preparatory TLC (90% EtoAc/hex) to give (±)-(4R*,5R*)-5-[(2E)(1R*)-3-(4-fluorophenyl)-1-hydroxyprop-2-enyl]-1-methyl-4-phenylpyrrolidin-2-one (30 mg, 26%) as a white solid: mp 189–191° C.; ¹H NMR (CDCl₃) δ 2.49–2.57 (m, 1H), 2.98 (s, 3H), 3.12–3.21 (m, 1H), 3.84–3.89 (m, 2H), 4.09–4.14 (m, 1H), 6.07 (dd, J=16.2, 5.0 Hz, 1H), 6.40 (dd, J=16.2, 1.7 Hz, 1H), 6.97–7.03 (m, 2H), 7.21–7.42 (m, 7H).

EXAMPLE 16

Preparation of (±)-5-[(2E)(1R*)-3-(4-fluorophenyl)-1-hydroxyprop-2-enyl](4R*),5*)-1-methyl-4-phenylpyrrolidin-2-one

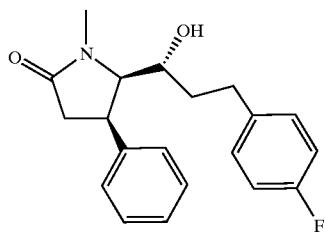

(±)-(4R*,5R*)-5-[(1R*)3-(4-Fluorophenyl)1-hydroxyprop-2-ynyl]-1-methyl-4-phenylpyrrolidin-2-one was prepared from 4-fluorophenyl acetylene and Intermediate Z using a method analogous to that described for Examples 8. A solution of this compound (52 mg, 0.16 mmol) in EtOAc (5 mL) was added to a catalyst slurry prepared by addition of EtOAc (10 mL) to 10% Palladium on carbon (20 mg) under an Ar atmosphere. The reaction mixture was stirred under a H₂ atmosphere (1 Atm) overnight. The resulting mixture was filtered through a pad of Celite® and the filtrate was concentrated under reduced pressure to give (±)-5-[(1R*)-3-(4-fluorophenyl)-1-hydroxypropyl](4R*,5R*)-1-methyl-4-phenylpyrrolidin-2-one (67 mg, 100%) as a white solid: mp 122–124° C.

EXAMPLE 17

Preparation of (±)-(4R*,5R*)-5-[(1S*)-hydroxy(5-phenyl(2-thienyl))methyl]-4-(4-aminophenyl)-1-methylpyrrolidin-2-one

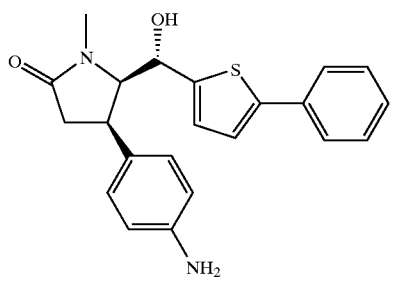

The ester of Intermediate U step 1 was reduced with lithium triethylborohydride using the procedure described as Method 2 in the preparation of Intermediate T. The resulting alcohol was then subjected to Swern oxidation using the procedure described as Method 1 in the preparation of Intermediate Z, followed by a reaction of the resulting aldehyde with 2-phenylthiophene and n-BuLi in a manner analogous to that of Example 3a. To the resulting product, (±)-(4R*,5R*)-5-[(1S*)-hydroxy(5-phenyl(2-thienyl))methyl]-4-(4-nitrophenyl)-1-methylpyrrolidin-2-one (110 mg, 0.27 mmol), in EtOH (10 mL) was added tin(II) chloride dihydrate (312 mg, 1.38 mmol, 5 equiv), and the resulting mixture was heated at 70° C. for 2.5 h, then allowed to cool to room temperature and poured onto ice water. A saturated NaHCO₃ solution was added to adjust the mixture to pH 8. The basic mixture was extracted with EtOAc, dried (MgSO₄) and concentrated under reduced pressure. The crude product was purified by flash chromatography (EtOAc) to give (±)-(4R*,5R*)-5-[(1S*)-hydroxy(5-phenyl(2-thienyl))methyl]-4-(4-aminophenyl)-1-methylpyrrolidin-2-one (63 mg, 60%) as a yellow solid: mp 221–222° C.; TLC (EtOAc) R_f 0.40; HPLC ES-MS m/z (rel abundance) 379 (MH⁺, 100%).

EXAMPLE 18

Preparation of (±)-(4R*,5R* )-5-[(1S*)hydroxy(5-phenyl(2-thienyl))methyl]-1-methyl-4-[4-(methylamino)phenyl]pyrrolidin-2-one

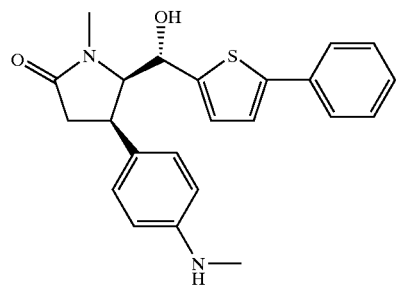

A mixture of (±)-(4R*,5R*)-5-[(1S*)-hydroxy(5-phenyl (2-thienyl))methyl]-4-(4-aminophenyl)-1-methylpyrrolidin-2-one (Example 17, 105 mg, 0.30 mmol), paraformaldehyde (13 mg, 0.42 mmol) and sodium methoxide (81 mg, 1.5 mmol) in methanol (1 mL) was stirred overnight. After adding sodium borohydride (12 mg, 0.30 mmol) the reaction mixture was heated at the reflux temperature for 1 h, then treated with a 1M NaOH solution (1 mL). The resulting mixture was stirred for 10 min, diluted with water (10 mL) and extracted with EtOAc (2×10 mL). The organic layer was washed with a saturated NaCl solution, dried (Na₂SO₄) and concentrated under reduced pressure to give a yellow solid. The crude product was sequentially triturated with EtOAc, Et₂O and hexane to provide (±)-(4R*,5R*)-5-[(1S*)-hydroxy(5-phenyl(2-thienyl))methyl]methyl-4-[4-(methylamino)phenyl]pyrrolidin-2-one (89 mg, 76%) as a white solid: TLC (EtOAc) R_f 0.34; mp: 212° C.

EXAMPLE 19

Preparation of (±)-(4R*,5R*)-5-[(1S*)-hydroxy(5-phenyl(2-thienyl))methyl]-1-methyl-4-[4-(dimethylamino)phenyl]pyrrolidin-2-one

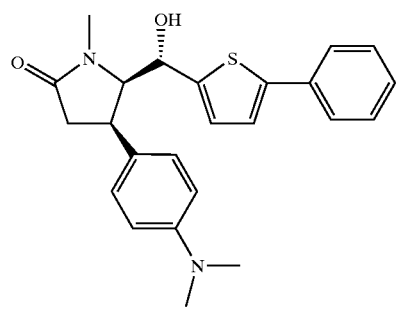

A mixture of (±)-(4R*,5R*)-5-[(1S*)-hydroxy(5-phenyl (2-thienyl))methyl]-1-methyl-4-[4-(methylamino)phenyl] pyrrolidin-2-one (Example 18, 70 mg, 0.18 mmol), methyl iodide (26 mg, 0.18 mmol) and potassium carbonate (49 mg, 0.36 mmol) in acetonitrile (1 mL) was stirred for 3 h. More methyl iodide (0.26 mg, 0.18 mmol) was added and the mixture was heated at the reflux temperature for 2 h. The reaction mixture was treated with sodium methoxide (20 mg, 0.36 mmol) and methanol (1 mL) and heated at the reflux temperature overnight. The resulting mixture was diluted with water (10 mL) and extracted with EtOAc (2×10 mL). The combined organic layers were washed with a saturated NaCl solution, dried (Na$_2$SO$_4$) and concentrated under reduced pressure. The crude product was purified by flash chromatography (EtOAc) to give a colorless oil, which was sequentially triturated with EtOAc, Et$_2$O and hexane to provide (±)-(4R*,5R*)-5-[(1S*)-hydroxy(5-phenyl(2-thienyl))methyl]4-[4-(dimethylamino)phenyl]-1-methylpyrrolidin-2-one (10 mg, 14%) as an off-white solid: TLC (EtOAc) R$_f$ 0.40; HPLC ES-MS m/z (rel abundance) 407 (MH$^+$, 100%).

EXAMPLE 20
Preparation of (±)-(4R*,5R*)-5-[(1S*)-hydroxy(5-phenyl(2-thienyl))methyl]-1-methyl-4-[4-hydroxyphenyl]pyrrolidin-2-one

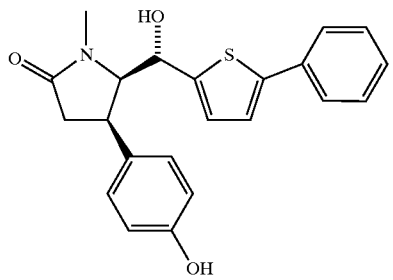

Intermediate Y was reduced with lithium triethylborohydride using the method described as Method 2 in the preparation of Intermediate T. The resulting alcohol was then subjected to Swern oxidation using the procedure described as Method 1 in the preparation of Intermediate Z, followed by a reaction of the resulting aldehyde with 2-phenylthiophene and n-BuLi in a manner analogous to that of Example 3a. The resulting product, (±)-(4R*,5R*)-5 [(1S*)-hydroxy(5-phenyl(2-thienyl))methyl]-1-methyl-4-[4-tert-butyldimethylsilyloxy)phenyl]pyrrolidin-2-one (0.050 g, 0.10 mmol), was dissolved in THF (1 mL) under Ar, a solution of TBAF (1M in THF, 0.11 mL, 0.11 mmol) was added, and the resulting solution was stirred for 4 min. The reaction was treated with water and a saturated NH$_4$Cl solution, then extracted with EtOAc. The combined organic layers were dried (MgSO$_4$) and concentrated under reduced pressure. The crude product was purified by flash chromatography (EtOAc) to yield (±)-(4R*,5R*)-5-[(1S*)-hydroxy(5-phenyl(2-thienyl))methyl]-4-(4-hydroxy-phenyl)-1-methylpyrrolidin-2-one (31 mg, 82%) as a white powder: mp 248–249° C.; TLC (EtOAc) R$_f$ 0.37.

EXAMPLE 21
Preparation of (±)-(4R*,5R*)-5-[(1S*)hydroxy(5-phenyl(2-thienyl))methyl]-4-[4-(hydroxymethyl)phenyl]-1-methylpyrrolidin-2-one Step 1: Preparation of (±)-(4R*,5R*)-5-[(1S*)hydroxy(5-phenyl(2-thienyl))methyl]-4-(4-(ethoxycarbonyl)phenyl)-1-methyl-pyrrolidin-2-one

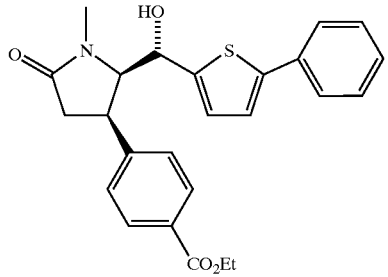

Intermediate V was reduced with lithium triethylborohydride using the method described as Method 2 in the preparation of Intermediate T. The resulting alcohol was then subjected to Swern oxidation using the procedure described as Method I in the preparation of Intermediate Z, followed by a reaction of the resulting aldehyde with 2-phenylthiophene and n-BuLi in a manner analogous to that of Example 3a. The resulting compound, (±)-(4R*,5R*)-5-[(1S*)hydroxy(5-phenyl(2-thienyl))methyl]-4-(4-iodophenyl)-1-methylpyrrolidin-2-one (0.100 g, 0.205 mmol), Et$_3$N (0.1 mL) and Pd(OAC)$_2$ (ca 10 mg) were stirred in EtOH (1 mL) under an atmosphere of carbon monoxide at 60° C. for 36 h. The resulting mixture was concentrated onto silica and the product isolated by flash chromatography (EtOAc) to yield (±)-(4R*,5R*)-5-[(1S*) hydroxy(5-phenyl(2-thienyl))methyl]-4-(4-(ethoxycarbonyl)phenyl)-1-methyl-pyrrolidin-2-one (60 mg, 67%) as an orange solid: mp 177–179° C.; TLC (EtOAc) R$_f$ 0.62.

Step 2: preparation of (±)-(4R*,5R*)-5-[(1S*)hydroxy(5-phenyl(2-thienyl))methyl]-4-[4-(hydroxymethyl)-phenyl]-1-methylpyrrolidin-2-one

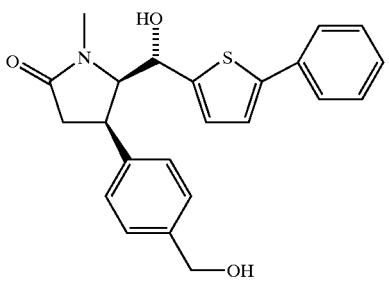

(±)-(4R*,5R*)-5-[(1S*)Hydroxy(5-phenyl(2-thienyl)) methyl]-4-(4-(ethoxycarbonyl)-phenyl)-1-methylpyrrolidin-2-one (0.046 g, 0.106 mmol) was dissolved in THF (1 mL) under Ar. A solution of LiBH$_4$ (2M in THF, 0.10 mL, 0.21 mmol) was added and the resulting mixture was stirred at room temperature for 18 h. Additional LiBH$_4$ solution (0.5 mL, 1.0 mmol) was added and the reaction was stirred for 24 h. The reaction was treated with a 1M HCl solution, followed by water and the resulting mixture was extracted with EtOAc. The combined organic layers were dried (MgSO$_4$) and concentrated under reduced pressure. The crude product was purified by HPLC to yield (±)-(4R*,5R*)-5-[(1S*) hydroxy(5-phenyl(2-thienyl))methyl]-4-[4-(hydroxymethyl)-phenyl]-1-methylpyrrolidin-2-one (9 mg, 20%) as a white solid: mp 205° C.; TLC (EtOAc)R$_f$ 0.24.

EXAMPLE 22
Preparation of (±)-(4R*,5R*)-5-[(1S*)hydroxy(5-phenyl(2-thienyl))-methyl]-4-[4-(4-fluorophenyl)phenyl]-1-methylpyrrolidin-2-one

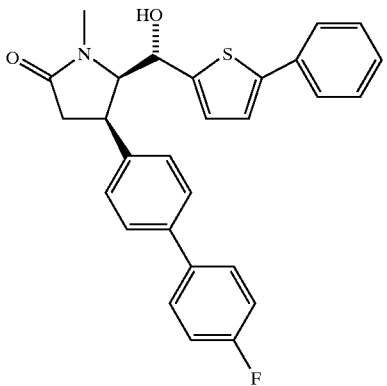

(±)-(4R*,5R*)-5-[(1S*)Hydroxy(5-phenyl(2-thienyl)) methyl]-4-(4-iodophenyl)-1-methylpyrrolidin-2-one prepared as described in Example 21, step 1, (0.100 g, 0.204 mmol), Pd(PPh3)₄ (0.025 g, 0.02 mmol) and 4-flourophenylboronic acid (0.037 g, 0.26 mmol) were stirred in anhyd. DME (1 mL). A 1M solution of Na₂CO₃ (0.55 mL, 0.55 mmol) in water was added and the resulting mixture was heated at the reflux temperature for 18 h. The reaction was cooled to room temperature and diluted with water. The resulting mixture was extracted with EtOAc, dried (MgSO₄) and concentrated under reduced pressure. The crude product was purified by flash chromatography (75% EtoAc/hex) to yield (±)-(4R*,5R*)-5-[(1S*)hydroxy (5-phenyl(2-thienyl))methyl]-4-[4-(4-fluorophenyl)phenyl]-1-methylpyrrolidin-2-one (0.046 g, 50%) as a yellow solid: mp 191–193° C.; ¹H NMR (CDCl₃) δ 2.29 (dd, J=14.5, 7.8 Hz, 1H), 2.96–3.06 (m, 1H), 3.30 (s, 3H), 3.85–3.89 (m, 1H), 4.23 (d, J=7.8 Hz, 1H), 4.50 (d, J=6.5 Hz, 1H), 5.99 (d, J=6.1 Hz, 1H), 6.88 (d, J=3.6 Hz, 1H).

EXAMPLE 23

Preparation of (±)-(4R*,5R*)-5-[(1S*)(5-ethynyl(2-thienyl))hydroxymethyl]-1-methyl-4-phenylpyrrolidin-2-one

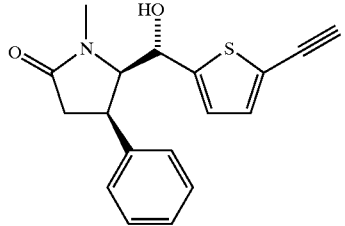

To a 0° C. solution of (±)-(4R*,5R*)-5-1{(1S*) [5-(2-(trimethylsilyl)ethynyl)(2-thienyl)]hydroxymethyl}-1-methyl-4-phenylpyrrolidin-2-one (prepared from Intermediate Z and trimethylsilylacetylene by a method analogous to that described for Example 8), 0.21 g, 0.57 mmol) in a mixture of MeOH (2 mL) and CH₂Cl₂ (3 mL) was added a KOH solution (1.78M in H₂O, 0.32 mL, 0.57 mmol). The reaction mixture was allowed to warm to room temperature, stirred for 17 h, then concentrated under reduced pressure and extracted with CH₂Cl₂ (3×20 mL). The combined organic layers were dried (MgsO₄) and concentrated under reduced pressure to give (±)-(4R*,5R*)-5-[(1S*)(5-ethynyl(2-thienyl))hydroxymethyl]-1-methyl-4-phenylpyrrolidin-2-one (0.175 g, 100%) as a light yellow solid: mp 187° C.; HPLC ES-MS m/z (relative abundance) 312 (MH⁺, 100%).

EXAMPLE 24

Preparation of (±)-(8S*,3aR*,8aR*)-8-hydroxy-1-methyl-8-(5-phenyl(2-thienyl))-indano [2,1-b] pyrrolidin-2-one Step 1: preparation of (±)-(4R*,5R*)-5-carboxy-1-methyl-4-phenylpyrrolidin-2-one

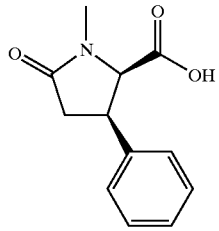

(±)-(4R*,5R*)-5-(Ethoxycarbonyl)-1-methyl-4-phenylpyrrolidin-2-one (16 g, 64.8 mmol), prepared according to the method of W. Hartwig and L. Born, *J. Org. Chem.*, 52, 4352 (1987), was heated at the reflux temperature overnight in a 3:1 mixture of 3M HCl solution and water. The resulting mixture was allowed to cool to room temperature, extracted with EtOAc, dried (Na2SO₄) and concentrated under reduced pressure. The crude product was triturated (Et₂O) to give (±)-(4R*,5R*)-5-carboxy-1-methyl-4-phenylpyrrolidin-2-one (9.5 g, 67%): ¹H NMR (CDCl₃) δ 2.60 (dd, J=8.3, 16.0 Hz, 1H), 2.82–2.91 (m, 4H), 3.90 (q, J=8.9 Hz, 1H), 3.95 (br s, 1H), 4.37 (d, J=8.6 Hz, 1H), 7.19–7.32 (m, 5H).

Step 2: preparation of (±)-(3aR*,8aR*)-1-methylindano[2,1-b]pyrrolidine-2,8-dione

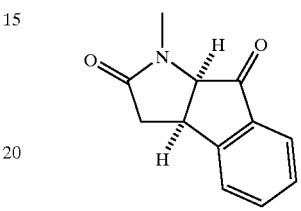

A mixture of (±)-(4R*,5R*)-5-carboxy-1-methyl-4-phenylpyrrolidin-2-one (0.66 g, 3.03 mmol) and thionyl chloride (5 mL) was heated at the reflux temperature for 1 h, then concentrated under reduced pressure. The residue was dissolved in CH₂Cl₂ (10 mL) and treated with aluminum chloride (0.88 g, 6.6 mmol). The resulting brown solution was stirred for 1 h, treated with water and extracted with EtOAc. The organic layer was washed with water, dried (Na₂SO₄) and concentrated under reduced pressure. The crude product was purified by flash chromatography (50% EtOAc/hex), followed by recrystallization (Et₂O) to give (±)-(3aR*,8aR*)-1-methylindano[2,1-b]pyrrolidine-2,8-dione (0.34 g, 55%) as a light-brown solid: mp 95–97° C.

Step 3: preparation of (±)-(8S*,3aR*,8aR*)-8-hydroxy-1-methyl-8-(5-phenyl(2-thienyl))indano[2,1-b]pyrrolidin-2-one

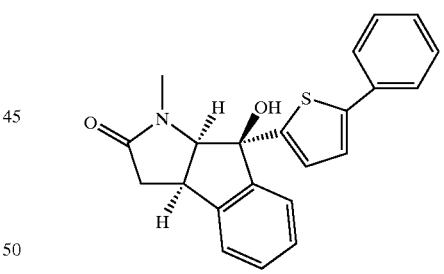

To a –78° C. solution of phenylthiophene (0.16 g, 1.0 mmol) in THF (2 mL) was added a solution of n-BuLi (1.6M in hexanes, 0.7 mL, 1.1 mmol). The reaction mixture was allowed to warm to –10° C., cooled back to –70° C., then treated with (±)-(3aR*,8aR*)-1-methylindano[2,1-b]pyrrolidine-2,8-dione (0.18 g, 0.9 mmol). The resulting mixture was stirred for 1 h, allowed to warm to 0° C., treated with a saturated NH₄Cl solution and extracted with EtOAc. The organic layer was dried (Na₂SO₄), concentrated under reduced pressure onto silica gel and purified by flash chromatography (50% EtOAc/hex) and trituration (Et₂O) to give (±)-(8S*,3aR*,8aR*)-8-hydroxy-1-methyl-8-(5-phenyl(2-thienyl))indano[2,1-b]pyrrolidin-2-one (40 mg, 12%): mp 178–180° C.; TLC (EtoAc) R_f 0.33; HPLC ES-MS m/z 362 (MH⁺).

EXAMPLE 25

Preparation of (±)-(4R*,5R*)-5-{(1S*)[5-(3-{[(4-fluorophenyl)amino]carbonylamino}phenyl)(2-thienyl)]hydroxymethyl}-1-methyl-4-phenylpyrrolidin-2-one

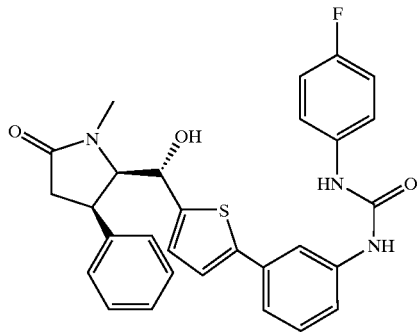

(±)-(4R*,5R*)-5-{(1S*) [5-(3-aminophenyl) (2-thienyl)] hydroxymethyl}-1-methyl-4-phenylpyrrolidin-2-one was prepared from (±)-(4R*,5R*)-5-[(1S*)(5-bromo(2-thienyl)) hydroxymethyl]-1-methyl-4-phenylpyrrolidin-2-one (Example 5, step 2) and 3-aminophenylboronic acid, using a procedure analogous to that described for Examples 5, step 3. A mixture of the resulting compound (0.2 g, 0.53 mmol) and 4-fluorophenylisocyanate (0.073 g, 0.53 mmol) in THF (5 mL) were heated at the reflux temperature for 4 h. The resulting mixture was treated with water and extracted with CH$_2$Cl$_2$. The organic layers were dried (MgSO$_4$) and concentrated under reduced pressure. The crude product was purified by flash chromatography (EtOAc) to give (±)-(4R*,5R*)-5-{1(1S*)[5-(3-{[(4-fluorophenyl)amino] carbonylamino}phenyl)(2-thienyl)]hydroxymethyl}-1-methyl-4-phenylpyrrolidin-2-one (0.15 g, 55%) as an off-white solid: mp: 181° C.; TLC (EtOAc) R$_f$ 0.26.

EXAMPLE 26

Preparation of (4R,5R)-5-{(S)-hydroxy[5-(1-oxido-3-pyridinyl)-2-thienyl]methyl}-1-methyl-4-phenyl 2-pyrrolidinone

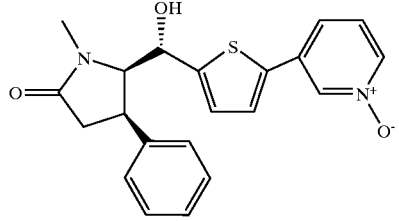

To a solution of (4R,5R)-5-{(1S)-hydroxy[5-(3-pyridinyl)-2-thienyl]methyl}-1-methyl-4-phenyl-2-pyrrolidinone (Example 3b, 0.20 g, 0.55 mmol) in CHCl$_3$ (10 mL) was added mCPBA (0.35 g, 1.4 mmol). The reaction mixture was stirred for 40 min, then was treated with a saturated NaHCO$_3$ solution (10 mL). The organic layer was dried (Na$_2$SO$_4$) and was allowed to stand overnight. The white precipitate was filtered off, the filtrate was concentrated under reduced pressure. The crude product was triturated (Et$_2$O/CH$_2$Cl$_2$) to give (4R,5R)-5-{(S)-hydroxy[5-(1-oxido-3-pyridinyl)-2-thienyl]methyl}-1-methyl-4-phenyl 2-pyrrolidinone: mp 138–140° C.; TLC (10% MeOH/CH$_2$Cl$_2$) R$_f$ 0.20; ES-LRMS m/z 381 (MH$^+$).

Utilizing the above described procedures for Intermediates A–DD and Examples 1–26 alone or in combination, a variety of compounds were prepared as summarized in the following tables.

TABLE 1

(2-Thienyl)hydroxymethyl Analogs

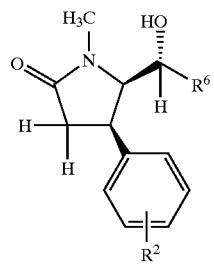

| Ex. No. | R$^6$ | R$^2$ | mp (° C.) | TLC R$_f$ | TLC Solvent System | Mass Spec. [Source] | Synth. Method |
|---|---|---|---|---|---|---|---|
| 27 | (thienyl-pyridinyl-methyl) | H | 173 | 0.26 | EtOAc | | K Z 3a |
| 28 | (thienyl-phenyl-N(CH$_3$)$_2$, F) | H | 173 | 0.43 | 67% EtOAc/hex | | K Z 3a |

TABLE 1-continued (2-Thienyl)hydroxymethyl Analogs

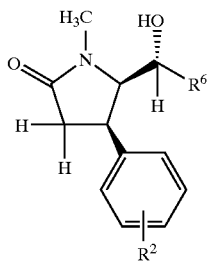

| Ex. No. | R[6] | R[2] | mp (° C.) | TLC $R_f$ | TLC Solvent System | Mass Spec. [Source] | Synth. Method |
|---|---|---|---|---|---|---|---|
| 29 | thiophene-thiophene | H | 152 | 0.49 | 67% EtOAc/hex | | K Z 3a |
| 30 | thiophene-2,6-difluorophenyl | H | | 0.41 | 67% EtOAc/hex | 400 (100%) MH+ ES-LCMS | K Z 3 a |
| 31 | thiophene-3-methoxyphenyl | H | 128 | 0.71 | 70% EtOAc/hex | | K Z 3 a |
| 32 | thiophene-4-CF3-phenyl | H | 206 | 0.39 | 66% EtOAc/hex | | Z 5 |
| 33 | thiophene-3-CO2H-phenyl | H | 231 | 0.26 | 0.5% AcOH/EtOAc | | Z 5 |
| 34 | thiophene-2-CF3-phenyl | H | 192 | 0.54 | 66% EtOAc/hex | | Z 5 |
| 35 | thiophene-SO2-thiomorpholine | H | 197–199 | 0.31 | EtOAc | | L Z 4, step 1 |

TABLE 1-continued
(2-Thienyl)hydroxymethyl Analogs
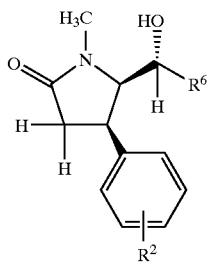
| Ex. No. | R⁶ | R² | mp (° C.) | TLC R_f | TLC Solvent System | Mass Spec. [Source] | Synth. Method |
|---|---|---|---|---|---|---|---|
| 36 | (5-morpholinosulfonyl-2-thienyl) | H | 214–218 | 0.36 | EtOAc | | L Z 4, step 1 |
| 37 | (5-(4-(4-fluorophenyl)piperazin-1-ylsulfonyl)-2-thienyl) | H | 167–175 | 0.55 | EtOAc | | L Z 4, step 1 |
| 38 | (5-methyl-4-phenyl-2-thienyl) | H | 78–82 | | | | Z 3 a |
| 39 | (5-(4-methoxyphenyl)-2-thienyl) | H | 168–170 | | | | Z 3a |
| 40 | (5-(quinolin-2-yl)-2-thienyl) | H | 225–228 | 0.33 | 90% EtOAc/ hex | | Z 3 a |
| 41 | (benzo[b]thien-2-yl) | H | 195 dec | 0.47 | EtOAc | | Z 3 a |

TABLE 1-continued
(2-Thienyl)hydroxymethyl Analogs
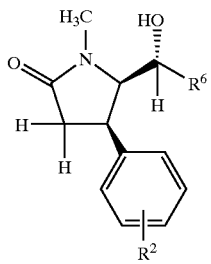
| Ex. No. | R$^6$ | R$^2$ | mp (° C.) | TLC R$_f$ | TLC Solvent System | Mass Spec. [Source] | Synth. Method |
|---|---|---|---|---|---|---|---|
| 42 | | H | 165 | 0.47 | EtOAc | | Z 3 a |
| 43 | | H | 85 | 0.54 | EtOAc | | Z 3 a |
| 44 | | H | 150 | 0.42 | EtOAc | | Z 5 |
| 45 | | H | 160 | 0.48 | EtOAc | | Z 5 |
| 46 | | H | 180 | 0.48 | EtOAc | | Z 5 |
| 47 | | H | 170 | 0.48 | EtOAc | | Z 5 |

TABLE 1-continued (2-Thienyl)hydroxymethyl Analogs

| Ex. No. | R⁶ | R² | mp (° C.) | TLC R$_f$ | TLC Solvent System | Mass Spec. [Source] | Synth. Method |
|---|---|---|---|---|---|---|---|
| 48 | thienyl-phenyl-NHAc | H | 97 | 0.15 | EtOAc | | Z 5 |
| 49 | thienyl-(3,4,5-triOMe-phenyl) | H | 190 dec | 0.33 | EtOAc | | Z 5 |
| 50 | thienyl-(2-pyridyl) | H | 234 dec | 0.37 | EtOAc | | Z 4, step 1 |
| 51 | thienyl-(4-Cl-phenyl) | H | | 0.19 | 70% EtOAc/hex | 398 MH⁺ ES-LCMS | Z 5 |
| 52 | thienyl-(4-OH-phenyl) | H | 184–186 dec. | 0.30 | EtOAc | | Q Z 3 a |
| 53 | 3-methyl-5-fluoro-benzothiophen-2-yl | H | 175–177 | 0.53 | EtOAc | | Z 3 a |
| 54 | benzothiophen-3-yl | H | >210 | 0.45 | EtOAc | | Z 4, step 1 |

TABLE 1-continued (2-Thienyl)hydroxymethyl Analogs

| Ex. No. | R⁶ | R² | mp (° C.) | TLC R$_f$ | TLC Solvent System | Mass Spec. [Source] | Synth. Method |
|---|---|---|---|---|---|---|---|
| 55 | (thienyl-CH=CH-4-F-phenyl, cis) | H | 160–162 dec | 0.60 | EtOAc | 408 MH+ ES-LCMS | M Z 4, step 1 |
| 56 | (thienyl-CH=CH-4-F-phenyl, trans) | H | 194–195 dec | 0.56 | EtOAc | | M Z 4, step 1 |
| 57 | (thienyl-CH₂CH₂-4-F-phenyl) | H | 123–125 | 0.69 | EtOAc | 410 MH⁺ ES-LRMS | M Z 4 16 |
| 58 | (thienyl-SO₂-4-OMe-phenyl) | H | 203–205 | 0.61 | 90% EtOAc/hex | 458 MH⁺ EI LRMS | Z 3 a |
| 59 | (thienyl-CH₂-4-F-phenyl) | H | 155–157 | 0.48 | EtOAc | | N Z 3 a |
| 60 | (thienyl-S-4-Cl-phenyl) | H | 174–176 | 0.60 | EtOAc | | Z 3 a |
| 61 | (thienyl-CH(OH)-4-F-phenyl) | H | | 0.66 | EtOAc | | N Z 3 a |

TABLE 1-continued
(2-Thienyl)hydroxymethyl Analogs
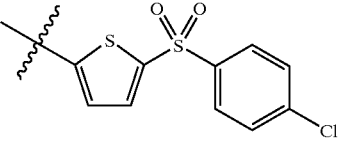
| Ex. No. | R⁶ | R² | mp (° C.) | TLC $R_f$ | TLC Solvent System | Mass Spec. [Source] | Synth. Method |
|---|---|---|---|---|---|---|---|
| 62 | 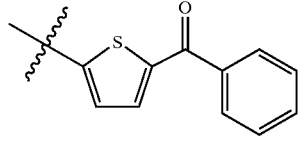 | H | 207–208 | 0.55 | EtOAc | | F Z 3 a |
| 63 | 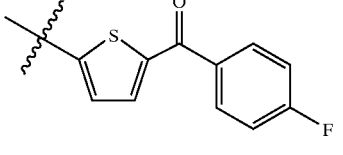 | H | 202 dec | 0.16 | 60% EtOAc/hex | 392 MH⁺ ES-LCMS | Z 4, step 1 |
| 65 | 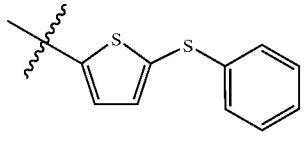 | H | 229–232 dec | 0.15 | 60% EtOAc/hex | 410 MH⁺ ES-LCMS | Z 4 |
| 66 | 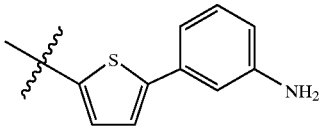 | H | 172 | 0.44 | EtOAc | | Z 3 a |
| 67 | 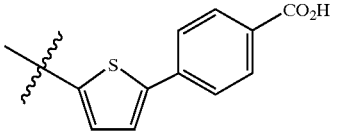 | H | 190 | 0.28 | EtOAc | | Z 5 |
| 68 | 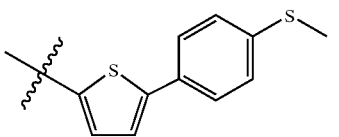 | H | 232 dec | 0.11 | EtOAc | | Z 5 |
| 69 | 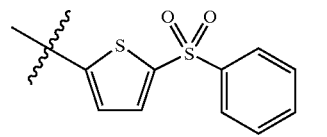 | H | 187 | 0.38 | EtOAc | | Z 5 |
| 70 |  | H | 247 | 0.47 | EtOAc | | Z 3 a |

TABLE 1-continued (2-Thienyl)hydroxymethyl Analogs

| Ex. No. | R[6] | R[2] | mp (° C.) | TLC R$_f$ | TLC Solvent System | Mass Spec. [Source] | Synth. Method |
|---|---|---|---|---|---|---|---|
| 71 | 2-(2-fluorophenyl)thien-5-yl | H | 216 | 0.49 | EtOAc | | DD Z 3 a |
| 72 | 2-(2-fluoro-4-methylphenyl)thien-5-yl | H | 182 | 0.43 | EtOAc | | DD Z 3 a |
| 73 | 2-(3-methanesulfonamidophenyl)thien-5-yl | H | 199 | 0.24 | EtOAc | | Z 5 L |
| 74 | 2-(3-dimethylaminophenyl)thien-5-yl | H | 193 | 0.41 | EtOAc | | K Z 3 a |
| 75 | 2-(2,4,6-trifluorophenyl)thien-5-yl | H | 95 | 0.20 | EtOAc | | K Z 3 a |
| 76 | 2-(4-fluorophenylsulfonyl)thien-5-yl | H | 192 | 0.42 | EtOAc | | G Z 3 a |
| 77 | 2-(2-methylthiopyrimidin-4-yl)thien-5-yl | H | 195 | 0.45 | EtOAc | | Z 4, step 1 |
| 78 | 2-(pyridin-3-yl)thien-5-yl | H | 210 | 0.25 | EtOAc | | Z 3 a |

TABLE 1-continued (2-Thienyl)hydroxymethyl Analogs

| Ex. No. | R⁶ | R² | mp (° C.) | TLC R$_f$ | TLC Solvent System | Mass Spec. [Source] | Synth. Method |
|---|---|---|---|---|---|---|---|
| 79 | thienyl-pyridyl·HCl | H | 175 | | | | Z<br>3 a |
| 80 | thienyl-C₆H₄-CN | H | 146 | 0.36 | EtOAc | | K<br>Z<br>3 a |
| 81 | thienyl-phenyl | 4-F | | 0.65 | EtOAc | | D<br>AA<br>T(2)<br>Z<br>3 a |
| 82 | thienyl-phenyl | 4-MeO | 215 | 0.46 | EtOAc | | X<br>T(2)<br>Z<br>3 a |
| 83 | thienyl-phenyl | 2-F | 219–220 dec | 0.40 | EtOAc | | D<br>AA<br>T(2)<br>Z<br>3 a |
| 84 | thienyl-C₆H₄-F | 2-F | 178 | 0.54 | EtOAc | | D<br>AA<br>T(2)<br>Z<br>3 a |
| 85 | thienyl-C₆H₄-F | 3-F | 195 | 0.54 | EtOAc | 400 MH⁺ ES-LCMS | D<br>AA<br>T(2)<br>Z<br>3 a |
| 86 | thienyl-C₆H₄-F | 4-NH₂ | 209 | 0.24 | EtOAc | | U<br>T(2)<br>Z<br>5<br>17 |

TABLE 1-continued (2-Thienyl)hydroxymethyl Analogs

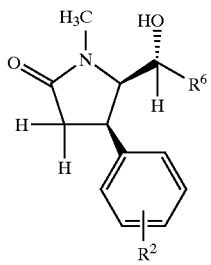

| Ex. No. | R⁶ | R² | mp (° C.) | TLC $R_f$ | TLC Solvent System | Mass Spec. [Source] | Synth. Method |
|---|---|---|---|---|---|---|---|
| 87 | thienyl-(4-fluorophenyl) | 3-MeO | 172 | 0.46 | EtOAc | | D AA T(2) Z 3 a |
| 88 | thienyl-(4-fluorophenyl) | 2-MeO | 179 | 0.45 | EtOAc | | D AA T(2) Z 3 a |
| 89 | thienyl-(phenylsulfonyl) | 2-F | 232 | 0.55 | EtOAc | | D AA T(2) Z 3 a |
| 90 | benzothiophen-3-yl | 2-F | 237–239 | 0.54 | EtOAc | | D AA T(2) Z 3 a |
| 91 | thienyl-(phenylsulfonyl) | 2-MeO | 160 | 0.38 | EtOAc | | D AA T(2) Z 3 a |
| 92 | thienyl-(4-chlorophenylsulfonyl) | 2-MeO | 220 | 0.45 | EtOAc | | D AA T(2) Z 3 a |

TABLE 2

(2-Phenyl)hydroxymethyl Analogs

| Ex. No. | R⁶ | R² | mp (° C.) | TLC R_f | TLC Solvent System | Mass Spec. [Source] | Synth. Method |
|---|---|---|---|---|---|---|---|
| 93 | 4-biphenyl | H | 202 | 0.45 | EtOAc | | Z 4 |
| 94 | 1-naphthyl | H | 255–256 | 0.78 | 90% EtOAc/hex | 332 MH⁺ FAB-LRMS | Z 6 |
| 95 | 4-methylphenyl | H | 129–131 | 0.65 | EtOAc | 296 MH⁺ FAB-LRMS | Z 7 |
| 96 | 3-CF₃-phenyl | H | 155–158 | 0.42 | EtOAc | 350 MH⁺ FAB-LRMS | Z 6 |
| 97 | 3-OMe-phenyl | H | 160–161 | 0.50 | 90% EtOAc/hex | 312 MH⁺ FAB-LRMS | Z 6 |
| 98 | 3-biphenyl | H | 173–176 | 0.46 | 90% EtOAc/hex | | Z 6 |
| 99 | 3,4-dichlorophenyl | H | 193–195 | 0.76 | EtOAc | | Z 6 |

TABLE 2-continued (2-Phenyl)hydroxymethyl Analogs

| Ex. No. | R⁶ | R² | mp (° C.) | TLC R_f | TLC Solvent System | Mass Spec. [Source] | Synth. Method |
|---|---|---|---|---|---|---|---|
| 100 | 4-MeO-C₆H₄- | H | 154–157 | 0.52 | EtOAc | 312 MH⁺ FAB-LRMS | Z 6 |
| 101 | 4-(Me₂N)-C₆H₄- | H | 182–185 | 0.27 | 90% EtOAc/hex | 325 MH⁺ FAB-LRMS | Z 6 |
| 102 | 3'-(AcNH)-biphenyl-3-yl | H | 150 | 0.12 | EtOAc | | Z 6 4, step 1 5, step 3 |
| 103 | 3'-F-biphenyl-3-yl | H | 187 | 0.44 | EtOAc | | Z 6 4, step 1 5, step 3 |
| 104 | 4'-F-biphenyl-3-yl | H | 210 | 0.44 | EtOAc | | Z 6 4, step 1 5, step 3 |
| 105 | 3'-NH₂-biphenyl-3-yl | H | 130 | 0.42 | EtOAc | | Z 6 4, step 1 5, step 3 |

TABLE 2-continued
(2-Phenyl)hydroxymethyl Analogs
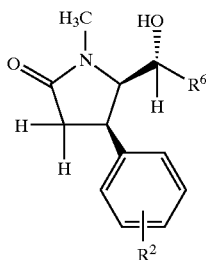
| Ex. No. | R⁶ | R² | mp (° C.) | TLC R_f | TLC Solvent System | Mass Spec. [Source] | Synth. Method |
|---|---|---|---|---|---|---|---|
| 106 | 3'-NO₂-biphenyl-3-yl | H | 183 | 0.48 | EtOAc | | Z<br>6<br>4, step 1<br>5, step 3 |
| 107 | 3'-OMe-biphenyl-3-yl | H | 183 | 0.46 | EtOAc | | Z<br>6<br>4, step 1<br>5, step 3 |
| 108 | benzo[1,3]dioxol-5-yl | H | 211 | 0.34 | EtOAc | | Z<br>6 |
| 110 | 4'-OH-biphenyl-3-yl | H | 230 | 0.3 | EtOAc | | Z<br>P<br>6 |
| 111 | 4'-F-biphenyl-4-yl | H | 117 | 0.49 | EtOAc | | Z<br>6 |

TABLE 3

(2-Furyl)hydroxymethyl Analogs

| Ex. No. | R⁶ | R² | mp (° C.) | TLC R$_f$ | TLC Solvent System | Mass Spec. [Source] | Synth. Method |
|---|---|---|---|---|---|---|---|
| 112 | 2-benzofuranyl | H | 120–122 | 0.4 | EtOAc | | Z 3 a |
| 113 | 5-methoxy-2-benzofuranyl | H | 180–182 | 0.18 | EtOAc | | Z 3 a |
| 114 | 5-(4-fluorophenyl)-2-furyl | H | 168 | 0.36 | EtOAc | | Z 4, step 1 5, step 3 |
| 115 | 5-(4-methylphenyl)-2-furyl | H | 187 | 0.34 | EtOAc | | Z 4, step 1 5, step 3 |
| 116 | 5-(4-methylthiophenyl)-2-furyl | H | 183 | 0.35 | EtOAc | | Z 4, step 1 5, step 3 |
| 117 | 5-phenyl-2-furyl | H | 184 | 0.39 | EtOAc | | Z 4, step 1 5, step 3 |
| 118 | 5-(4-carboxyphenyl)-2-furyl | H | 194 | 0.15 | EtOAc | | Z 4, step 1 5, step 3 |
| 119 | 5-(3-aminophenyl)-2-furyl | H | 98 | 0.27 | EtOAc | | Z 4, step 1 5, step 3 |

TABLE 3-continued (2-Furyl)hydroxymethyl Analogs

| Ex. No. | R⁶ | R² | mp (° C.) | TLC R_f | TLC Solvent System | Mass Spec. [Source] | Synth. Method |
|---|---|---|---|---|---|---|---|
| 120 | furyl-phenyl-OMe | H | 157 | 0.37 | EtOAc | | Z 4, step 1 5, step 3 |
| 121 | furyl-phenyl-NHC(O)CH₃ | H | 193 | 0.12 | EtOAc | | Z 4, step 1 5, step 3 |
| 122 | furyl-phenyl-F | H | 180 | 0.38 | EtOAc | | Z 4, step 1 5, step 3 |
| 123 | furyl-phenyl-NO₂ | H | 100 | 0.31 | EtOAc | | Z 4, step 1 5, step 3 |

TABLE 4

(2-Alkyl)hydroxymethyl Analogs

| Ex. No. | R⁶ | R² | mp (° C.) | TLC R_f | TLC Solvent System | Mass Spec. [Source] | Synth. Method |
|---|---|---|---|---|---|---|---|
| 124 | –C≡C–C₆H₄–F | H | 154–156 | 0.62 | EtOAc | | Z 8 |

TABLE 4-continued (2-Alkyl)hydroxymethyl Analogs

| Ex. No. | R⁶ | R² | mp (° C.) | TLC R_f | TLC Solvent System | Mass Spec. [Source] | Synth. Method |
|---|---|---|---|---|---|---|---|
| 125 | (ethynyl-2-pyridyl) | H | | 0.3 | EtOAc | | Z 8 |
| 126 | (ethynyl-2-chlorophenyl) | H | 139–140 | 0.62 | EtOAc | | Z 8 |
| 127 | (ethynyl-2-fluorophenyl) | H | | 0.62 | EtOAc | | Z 8 |
| 128 | (ethynyl-4-chlorophenyl) | H | | 0.62 | EtOAc | | Z 8 |
| 129 | (ethynyl-4-methylphenyl) | H | | 0.62 | EtOAc | | Z 8 |
| 130 | (propargyl-thiomorpholine-S,S-dioxide) | H | 217–218 | 0.64 | EtOAc | | Z 8 |
| 131 | (ethynyl-3-(2,5-dimethylpyrrolyl)phenyl) | H | 175–176 | 0.58 | EtOAc | | Z 8 |
| 132 | (ethynyl-3-hydroxyphenyl) | H | 210–211 | 0.52 | EtOAc | | Z 8 |

TABLE 4-continued
(2-Alkyl)hydroxymethyl Analogs
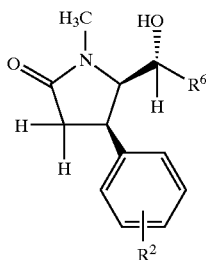
| Ex. No. | R⁶ | R² | mp (° C.) | TLC R_f | TLC Solvent System | Mass Spec. [Source] | Synth. Method |
|---|---|---|---|---|---|---|---|
| 133 | —C≡C—(3-aminophenyl) | H | 205–207 | | | | Z BB 8 |
| 134 | —C≡C—(3-methoxyphenyl) | H | | 0.60 | EtOAc | | Z 8 X |
| 135 | —C≡C—(4-methoxyphenyl) | H | | 0.51 | EtOAc | | Z 8 |
| 136 | —C≡C—(4-phenylphenyl) | H | 217–218 | 0.64 | EtOAc | | Z 8 |
| 137 | —CH₂CH₂—Ph | H | | 0.76 | EtOAc | | Z 8 16 |
| 138 | —CH₂—(4-phenylthiazol-2-yl) | H | 189 | 0.3 | EtOAc | | Z 4, step 1 |

TABLE 5

Miscellaneous Pyrrolidinones

| Ex. No. | Structure | mp (° C.) | TLC $R_f$ | TLC Solvent System | Mass Spec. [Source] | Synth. Method |
|---|---|---|---|---|---|---|
| 139 | 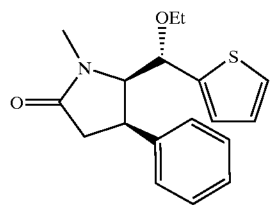 | 142–144 | 0.58 | 90% EtOAc/hex | | 12 |
| 140 | 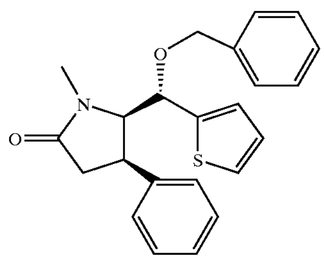 | 129–130 | 0.31 | 50% EtOAc/hex | | 12 |
| 141 | 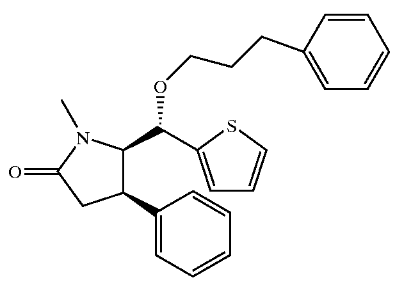 | 76–78 | 0.40 | 70% EtOAc/hex | | 12 |
| 142 | 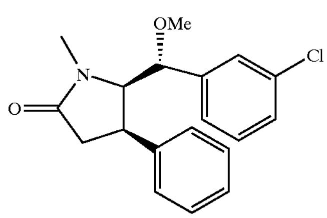 | 95–96 | 0.43 | EtOAc | 330 MH+ CI-LRMS | Z 4, step 1 12 |
| 143 | 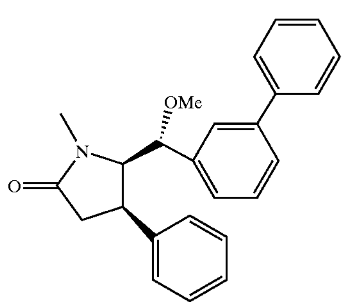 | 136 | 0.53 | EtOAc | | Z 6 12 |

TABLE 5-continued

Miscellaneous Pyrrolidinones

| Ex. No. | Structure | mp (°C.) | TLC $R_f$ | TLC Solvent System | Mass Spec. [Source] | Synth. Method |
|---|---|---|---|---|---|---|
| 144 | 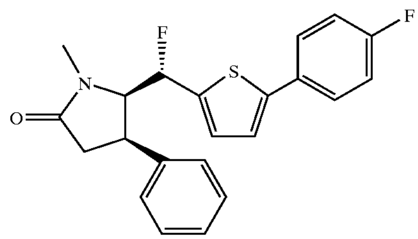 | 121–123 | 0.70 | EtOAc | | O<br>Z<br>3 a<br>14 |

TABLE 6

Enantiomerically Pure Pyrrolidinones

| Ex. No. | Structure | mp (°C.) | HPLC Sep. Method (Ret. Time, min) | HPLC Solvent System | Syn. Method |
|---|---|---|---|---|---|
| 145 | 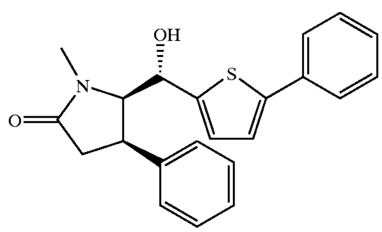 | 216(dec) | B (8) | 50% EtOH/hex | Z<br>3 a |
| 146 | 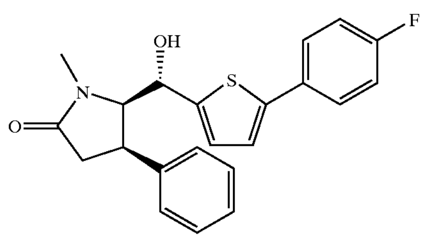 | | C (13) | 50% EtOH/hex | Z<br>3 a |
| 147 | 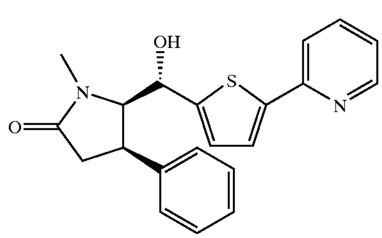 | | B (33) | 50% EtOH/hex | Z<br>4 |
| 148 | 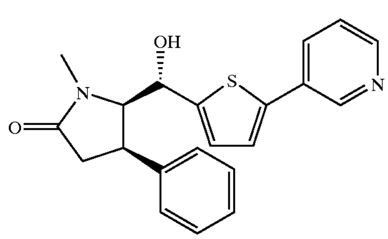 | 232—232 | B (29) | 50% EtOH/hex | Z<br>3 b |

TABLE 6-continued

Enantiomerically Pure Pyrrolidinones

| Ex. No. | Structure | mp (° C.) | HPLC Sep. Method (Ret. Time, min) | HPLC Solvent System | Syn. Method |
|---|---|---|---|---|---|
| 149 | 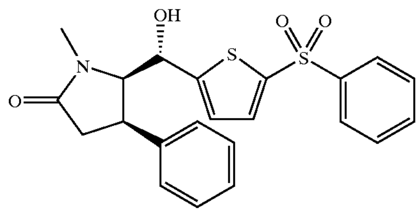 | | B (30) | 70% EtOH/hex | Z 3 a |
| 150 | 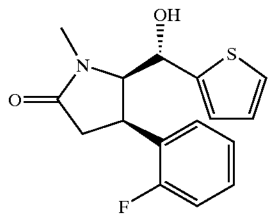 | 212 | D | 50% EtOH/hex | Z 3 a |
| 151 | 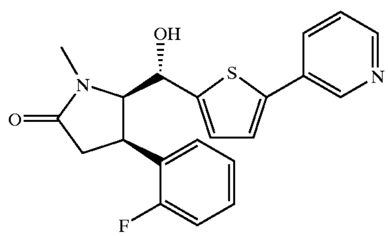 | 195–197 | D | 50% EtOH/hex | Z 3 a |
| 152 | 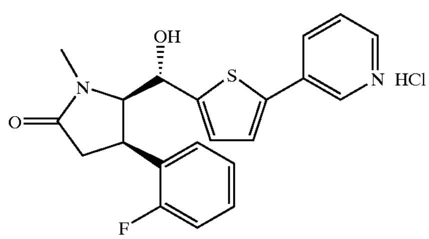 | 180–182 | D | 50% EtOH/hex | Z 3 a |
| 153 | 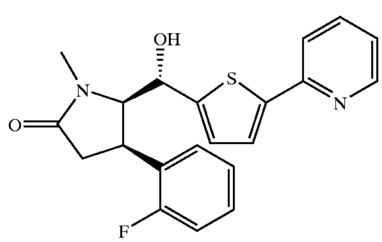 | 213–215 | D | 50% EtOH/hex | Z 4 |
| 154 | 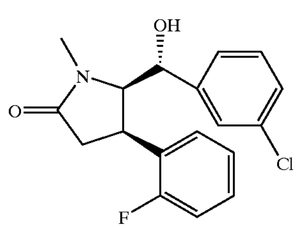 | 184–185 | D | 50% EtOH/hex | Z 6 |

TABLE 6-continued

Enantiomerically Pure Pyrrolidinones

| Ex. No. | Structure | mp (° C.) | HPLC Sep. Method (Ret. Time, min) | HPLC Solvent System | Syn. Method |
|---|---|---|---|---|---|
| 155 | (structure) | 200–202 | D | 50% EtOH/hex | D AA T(2) Z 3 a |

Biological Testing Materials and Methods

HSD II protein purification: The method for purification of baculovirus-expressed HSD II was standardized as follows. The insect cell pellet containing recombinant HSD II was lysed in 2.5 volumes of lysis buffer (40 mM Tris, pH 7.5, 1 mM EDTA, 2 mM DTT, 10 uM NAD) containing 500 uM AEBSF, 10 ug/ml aprotinin, 1 uM pepstatin A, and 100 uM leupeptin. The pellet was nutated for 30 min in this buffer. Subsequently, the pellet was homogenized with 15 strokes using a glass and teflon potter. The volume was doubled with a 2× sucrose/NaCl solution (500 mM sucrose, 300 mM NaCl in lysis buffer). After centrifugation at 10,000×g for 30 min, the supernatant was decanted and stored at −20° C. The pellet was resuspended in 2.5 volumes of lysis buffer containing 250 mM sucrose and 150 mM NaCl. Homogenization was repeated (15 strokes) and the suspension was centrifuged again and the decanted supernatant was stored at −20° C. The pellet was resuspended with 2 times the original pellet volume in lysis buffer containing 150 mM NaCl and 1% Triton X-100. The suspension was nutated for 20 min and then homogenized with 5 strokes. Subsequently, the suspension was centrifuged at 30,000×g for 1 h and supernatant was decanted and poured into a chromatographic column. Sephadex G-25 (fine) was added in small amounts, allowing approximately 15 min after each addition for complete swelling. Sephadex addition was continued until all liquid was absorbed. The protein was eluted with 1 void volume of lysis buffer and eluate monitored at 280 nm optical density. The chromatographic procedure was repeated and an equal volume of glycerol was added to the final eluate.

Primary assay: After titration, the HSD II prep, generated with the standard protocol, was diluted to the appropriate concentration (generally 1/15 dilution). 55 µl of assay buffer (50 mM Hepes, pH 8.0) was added to all wells of a 96 well plate. 5 µl of 5% DMSO were added to wells A1–C1, A2–C2, F1–H1, and F2–H2. A 10 µl aliquot of a 10 mM solution in DMSO of each compound was diluted in 190 µl of assay buffer. The plate with these compound dilutions was then mixed for 15 min on a shaker and a 5 µl aliquot from each well was added to the test pilot. This was followed by 10 µl of HSD II enzyme (1/15 dilution)/estradiol mix in assay buffer containing 1% Triton X-100. The estradiol red from a 20 mM estradiol DMSO stock solution, which was diluted 1/20 (50 µl/ml) in 50 mM Hepes buffer containing 1% Triton X-100. All wells, except F1–H1 and F2–H2, also received 10 µl of 25 mg/ml NAD (SIGMA) in 100 mM Hepes, pH 9. The blank wells F1–H1 and F2–H2 received 10 µl of NAD buffer. 20 µl of PMS:MTS solution (100 µl PMS into 1800 µl MTS, Promega) was added to all wells. The plate was covered with aluminum foil and incubated at room temperature for 1.5 h. The plate was analyzed at 490 nm on a Hewlett Pachard 8453 spectrophotometer and results were calculated.

$IC_{50}$ concentrations were determined for exemplified compounds, and the results are summarized in Table 7.

TABLE 7

Inhibition of 17-Beta HSD II Enzyme

| Compounds with $IC_{50}$ values <500 nM (Example Number) | Compounds with $IC_{50}$ values ≥500 nM and <2 µM (Example Number) | Compounds with $IC_{50}$ values ≥2 µM and <10 µM (Example Number) |
|---|---|---|
| 3 | 4 | 1 |
| 8 | 5 | 2 |
| 10 | 7 | 9 |
| 11 | 13 | 12 |
| 17 | 15 | 14 |
| 20 | 16 | 19 |
| 23 | 18 | 21 |
| 26 | 24 | 22 |
| 29 | 27 | 25 |
| 30 | 33 | 28 |
| 31 | 39 | 32 |
| 34 | 40 | 47 |
| 35 | 41 | 54 |
| 36 | 42 | 69 |
| 37 | 45 | 87 |
| 38 | 46 | 94 |
| 43 | 48 | 104 |
| 44 | 49 | 106 |
| 50 | 56 | 115 |
| 51 | 59 | 116 |
| 52 | 60 | 117 |
| 53 | 61 | 118 |
| 55 | 63 | 120 |
| 57 | 65 | 121 |
| 58 | 75 | 122 |
| 62 | 77 | 123 |
| 66 | 81 | 130 |
| 67 | 82 | 136 |
| 68 | 86 | 138 |
| 70 | 93 | 139 |
| 71 | 95 | 140 |
| 72 | 96 | 141 |
| 73 | 97 | 142 |
| 74 | 100 | |
| 76 | 101 | |
| 78 | 102 | |
| 79 | 103 | |
| 80 | 105 | |
| 83 | 107 | |
| 84 | 108 | |

TABLE 7-continued

Inhibition of 17-Beta HSD II Enzyme

| Compounds with IC$_{50}$ values <500 nM (Example Number) | Compounds with IC$_{50}$ values ≧500 nM and <2 μM (Example Number) | Compounds with IC$_{50}$ values ≧2 μM and <10 μM (Example Number) |
|---|---|---|
| 85 | 110 | |
| 88 | 111 | |
| 89 | 112 | |
| 90 | 113 | |
| 91 | 114 | |
| 92 | 119 | |
| 98 | 125 | |
| 99 | 128 | |
| 124 | 129 | |
| 126 | 132 | |
| 127 | 134 | |
| 131 | 135 | |
| 133 | 137 | |
| 145 | 143 | |
| 146 | 144 | |
| 147 | | |
| 148 | | |
| 149 | | |
| 150 | | |
| 151 | | |
| 152 | | |
| 153 | | |
| 154 | | |
| 155 | | |

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

We claim:

1. A compound having the structural formula

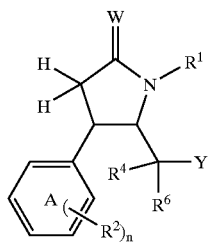

(I)

wherein
the phenyl group labeled A and the group —C(R$^4$)(R$^6$)Y are oriented cis to each other;
W represents O or S;
R$^1$ represents
—H; or
—(C$_1$–C$_4$)alkyl which is optionally substituted with up to three halogens;
n represents 0 or an integer of 1–3;
R$^2$ represents
—N(R$^3$)$_2$,
—OR$^3$,
—SR$^3$,
-halogen,
-phenyl which is optionally substituted with halogen up to perhalo, or
—(C$_1$–C$_4$)alkyl which is optionally substituted with halogen, —OR$^3$, or SR$^3$; the number of said substituents being up to three for halogen, and up to two for any combination of said —OR$^3$ and —SR$^3$ moieties; and wherein
R$^3$ represents —H or —(C$_1$–C$_4$)alkyl which is optionally substituted with up to three halogens;
R$^4$ represents —H or a bond terminating at the ortho position of phenyl ring A;
Y represents fluorine, —OR$^5$, or —SR$^5$; wherein
R$^5$ represents
—H;
—(C$_1$–C$_4$)alkyl optionally substituted with up to three halogens;
-phenyl which is optionally substituted with halogen, —OR$^{3A}$, —SR$^{3A}$, or —R$^{3A}$, the number of said substituents being up to perhalo for halogen, and up to two for any combination of said —QR$^{3A}$, —SR$^{3A}$, and —R$^{3A}$ moieties; wherein
R$^{3A}$ represents —(C$_1$–C$_4$)alkyl optionally substituted with up to three halogens; and
with the proviso that R$^5$ may represent an optionally substituted phenyl group only if R$^6$ represents H;
—(C$_1$–C$_4$)alkyl-phenyl in which the alkyl portion is optionally substituted with up to three halogens; and the phenyl portion is optionally substituted with halogen, —OR$^{3A}$, —SR$^{3A}$, or —R$^{3A}$, the number of substituents on said phenyl portion being up to perhalo for halogen, and up to two for any combination of said —OR$^{3A}$, —SR$^{3A}$, and —R$^{3A}$ moieties; or
—(C$_1$–C$_4$)acyl optionally substituted with up to three halogens;
R$^6$ represents
1) —H; with the proviso that when R$^6$ is H, then Y is OR$^5$ wherein R$^5$ is phenyl which is optionally substituted with halogen, —OR$^{3A}$, —SR$^{3A}$, or —R$^{3A}$; the number of said substituents being up to perhalo for halogen, and up to two for any combination of said —OR$^{3A}$, —SR$^{3A}$, and —R$^{3A}$ moieties;

wherein
m represents 0 or an integer of 1–3; with the further proviso that when W is O and Y is OH, at least one of m and n is nonzero;
X represents O or S;
R$^8$ represents
a) —(C$_6$–C$_{10}$)aryl, which is optionally substituted with one or more substituents selected from
-halogen,
—NCR$^3$)$_2$;
—OR$^3$;
—SR$^3$;
—CO$_2$R$^3$;
—NO$_2$;
—CN;
—(C$_1$–C$_6$)alkyl optionally substituted with up to three halogens;
-phenyl which is optionally substituted with halogen, —OR$^{3A}$, —SR$^{3A}$, or
—R$^{3A}$; the number of said substituents being up to perhalo for halogen, and up to two for any combination of said —OR³ᴬ, —SR³ᴬ, and —R³ᴬ moieties;
-heteroaryl of 5 members and containing 1–2 heteroatoms selected from N, O, and S;
—NHCOR⁹; in which R⁹ represents R³ᴬ or -phenyl which is optionally substituted with halogen up to perhalo;
—NHCONHR⁹; and
—NHSO₂R⁹;
the number of substituents on said (C₆–C₁₀)aryl group being up to perhalo for halogen, and up to three for any combination of said —N(R³)₂, —OR³, —SR³, —CO₂R³, —NO₂, —CN, —(C₁–C₆)alkyl, -phenyl, -heteroaryl, —NHCOR⁹, —NHCONHR⁹, and —NHSO₂R⁹ moieties;
b) -heteroaryl of 5–10 members and containing 1–3 heteroatoms selected from
N, O, and S; and being optionally substituted with halogen, —N(R³)₂, —OR³ᴬ, SR³ᴬ—CO₂R³, —NO₂, —CN, or
—(C₁–C₆)alkyl which is optionally substituted with up to three halogens;
the number of said substituents on the heteroaryl group being up to perhalo for halogen, and up to two for any combination of said —N(R³)₂, —OR³ᴬ, —SR³ᴬ, —CO₂R³, —NO₂, —CN, and —(C₁–C₆)alkyl moieties;
c) —(C₂)alkynyl-R¹⁰ wherein
R¹⁰ represents H; R³ᴬ; or -phenyl which is optionally substituted with halogen, —OR³, —SR³, or —R³ᴬ; the number of said substituents being up to perhalo for halogen, and up to two for any combination of said —OR³, —SR³, and —R³ᴬ moieties;
d) —(C₁–C₄)alkyl-R¹¹ wherein
the alkyl portion is optionally substituted with halogen, —OR³, or
—SR³; the number of said substituents being up to three for halogen, and up to two for any combination of said —OR³ and —SR³ moieties; and
R¹¹ represents
—H, provided that m is 2 or 3; or
-phenyl optionally substituted with halogen up to perhalo;
e) —S(O)₀₋₂R¹² wherein
R¹² represents
—(C₁–C₆)alkyl optionally substituted with halogen;

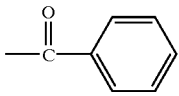

wherein
Z represents O, S(O)₀₋₂, C(R³)₂, or NR¹³ wherein R¹³ represents R³ᴬ; or -phenyl which is optionally substituted with halogen, —OR³ᴬ, SR³ᴬ, or —(C₁–C₂)alkyl optionally substituted with up to three halogens; the number of said substituents on phenyl being up to perhalo for halogen, and up to two for any combination of said —OR³ᴬ, SR³ᴬ, and —(C₁–C₂)alkyl moieties;
-phenyl, optionally substituted with halogen, —OR³ or —R³ᴬ; the number of said substituents being up to perhalo for halogen, and up to two for any combination of said —OR³ and —R³ᴬ moieties; or -heteroaryl of 5–6 members and containing 1–3 heteroatoms selected from N, O, and S;
f) —C(R¹⁴)=CHR¹⁴ wherein
R¹⁴ represents H; -halogen; —OR³ᴬ; or phenyl optionally substituted with halogen or with —R³ᴬ; the number of said substituents being up to perhalo for halogen, and up to two for —R³ᴬ moieties; and
with the proviso that when 2 such alkenyl groups are adjacent to each other, they may be joined, and taken together with the ring atoms to which they are attached, constitute a fused 6-membered ring;
g)

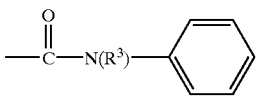

optionally substituted with halogen, —OR³ᴬ or —(C₁–C₆)alkyl optionally substituted with up to three halogens; the number of said substituents on phenyl being up to perhalo for halogen, and up to two for any combination of said —OR³ᴬ or —(C₁–C₆)alkyl moieties;
h)

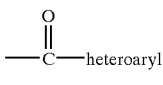

wherein the phenyl ring is optionally substituted with halogen, —OR³ᴬ, or —(C₁–C₆)alkyl optionally substituted with up to three halogens; the number of said substituents on phenyl being up to perhalo for halogen, and up to two for any combination of said —OR³ᴬ and —(C₁–C₆)alkyl moieties;
i)

$$\overset{O}{\underset{\|}{-C}}-\text{heteroaryl}$$

wherein the heteroaryl ring contains 5–6 members and up to 3 heteroatoms selected from N, O, and S, and is optionally substituted with up to 2 substitutents R³ᴬ;
3) —(C₁–C₄)alkyl-R¹⁵ wherein
the alkyl portion is optionally substituted with up to three halogens; and
R¹⁵ represents
-phenyl optionally substituted with halogen, —R³ᴬ, —OR³ᴬ, or with
-phenyl' optionally substituted with halogen up to perhalo; the number of said substituents on said phenyl being up to perhalo for halogen, and up to two for any combination of said —R³ᴬ, —OR³ᴬ, or -phenyl' moieties; or
a heteroaryl ring of 5–6 members and containing up to 3 heteroatoms selected from N, O, and S, and optionally bearing up to 2 substituents selected from halogen, —R³ᴬ, —OR³ᴬ, and -phenyl optionally substituted with halogen up to perhalo;
4) —CH=CH—(C₆–C₁₀)aryl-(R¹⁶)ₛ wherein
s represents 0 or an integer of 1–4;
R¹⁶ represents a substituent selected from halogen, —R³ᴬ, —N(R³)₂, —OR³ᴬ, —SR³ᴬ, —NO₂, and —CO₂R³;

5) —CH═CH-heteroaryl wherein the heteroaryl ring contains 5–6 members and up to 3 heteroatoms selected from N, O, and S; and is optionally substituted with $R^{3A}$;

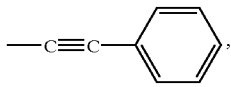

6) optionally substituted with halogen, —$R^{3A}$; —$N(R^3)_2$; —$OR^{3A}$; —$SR^{3A}$; —$NO_2$; —$CO_2R^3$; phenyl' optionally substituted with halogen up to perhalo; and -heteroaryl of 5–6 members and containing up to 3 heteroatoms selected from N, O, and S and optionally substituted with up to 2 substituents $R^{3A}$; the number of said substituents on phenyl being up to perhalo for halogen, and up to two for any combination of said —$R^{3A}$; —$N(R^3)_2$; —$OR^{3A}$; —$SR^{3A}$; —$NO_2$; —$CO_2R^3$; and phenyl' moieties;

7) —C≡C-heteroaryl wherein the heteroaryl ring contains 5–6 members and up to 3 heteroatoms selected from N, O, and S, and is optionally substituted with up to 2 substituents $R^{3A}$;

8) —C═C—$CH_2$—$R^{12}$ 9) phenyl, optionally substituted with halogen up to perhalo, with the proviso that when this phenyl group is unsubstituted or bears a halogen substituent, then ring A also bears at least one substituent; this phenyl being also optionally substituted with up to 2 substituents selected from
  -phenyl', optionally substituted with halogen, —$NHCOR^3$, —$N(R^3)_2$, —$OR^3$, or
    —$NO_2$; the number of said substituents being up to perhalo for halogen,
    and up to two for any combination of said —$NHCOR^3$, —$N(R^3)_2$, —$OR^3$,
    and —$NO_2$ moieties;
  -heteroaryl of 5–6 members and containing up to 3 heteroatoms selected from N, O, and S;

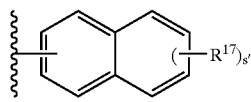

10) wherein
  s' represents 0, 1, or 2; and
  $R^{17}$ represents halogen; $R^{3A}$; —$OR^3$; or —$N(R^3)_2$;

11)

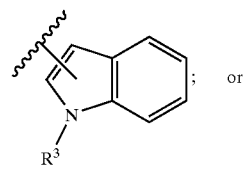; or

12)

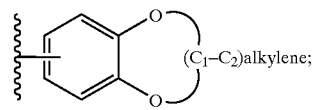

and with the further provisos that:
  an aliphatic carbon atom attached to oxygen may not also bear a halogen substituent;
  when any alkyl group is attached to O, S, or N, and bears a hydroxyl substituent, then said hydroxyl substituent is separated by at least two carbon atoms from the O, S, or N to which the alkyl group is attached; and
  two alkyl groups located on the same N atom they may be linked by a bond, an O, an S, or $NR^3$ to form a N-containing heterocycle of 5–7 ring atoms;
or a pharmaceutically acceptable salt thereof or N-oxide thereof.

2. A compound of claim 1 wherein $R^4$ represents H, $R^6$ represents H, and Y represents an —O-phenyl moiety.

3. A compound of claim 1 wherein $R^4$ represents H and $R^6$ represents

4. A compound of claim 1 wherein $R^4$ represents H and $R^6$ represents —$(C_1–C_4)$alkyl-$R^{15}$.

5. A compound of claim 1 wherein $R^4$ represents H and $R^6$ represents —CH═CH—$(C_6–C_{10})$aryl-$(R^{16})_3$.

6. A compound of claim 1 wherein $R^4$ represents H and $R^6$ represents —CH═CH-heteroaryl.

7. A compound of claim 1 wherein $R^4$ represents H and $R^6$ represents

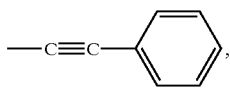

—C═C-heteroaryl, or —C═C—$CH_2$—$R^{12}$.

8. A compound of claim 1 wherein $R^4$ represents H and $R^6$ represents optionally substituted phenyl.

9. A compound of claim 1 wherein $R^4$ represents H and $R^6$ represents

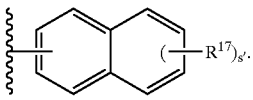

10. A compound of claim 1 wherein $R^4$ represents H and $R^6$ represents

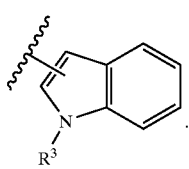

11. A compound of claim 1 wherein R⁴ represents H and R⁶ represents

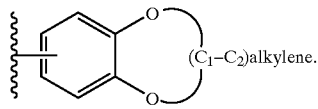

12. A compound of claim 1 wherein R⁴ represents a bond to the ortho position of ring A and R⁶ represents

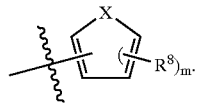

13. A compound of claim 1 wherein R⁴ represents a bond to the ortho position of ring A and R⁶ represents optionally substituted phenyl.

14. A compound of claim 1 selected from the group consisting of

| Example Number | IUPAC Name |
|---|---|
| 3a | rel-(4R,5R)-5-[[5-(4-fluorophenyl)-2-thienyl](hydroxy)methyl]-1-methyl-4-phenylpyrrolidin-2-one; |
| 3b | rel-(4R,5R)-5-{(1S)-hydroxy[5-(3-pyridinyl)-2-thienyl]methyl}-1-methyl-4-phenyl-2-pyrrolidinone; |
| 8 | rel-5-((1R)-1-hydroxy-3-phenylprop-2-ynyl)(4R,5R)-1-methyl-4-phenylpyrrolidin-2-one; |
| 10 | rel-(4R,5R)-5-[1H-indol-2-yl(methylthio)methyl]-1-methyl-4-phenylpyrrolidin-2-one; |
| 11 | (4R,5R)-5-[(1R)-hydroxy(5-phenyl(2-thienyl))methyl]-1-methyl-4-phenylpyrrolidin-2-one; |
| 17 | rel-(4R,5R)-4-(4-aminophenyl-5-[hydroxy(5-phenyl-2-thienyl)methyl]-1-methylpyrrolidin-2-one; |
| 20 | rel-(4R,5R)-4-(4-hydroxyphenyl)-5-[hydroxy(5-phenyl-2-thienyl)methyl]-1-methylpyrrolidin-2-one; |
| 23 | rel-(4R,5R)-5-[(5-ethynyl-2-thienyl)(hydroxy)methyl]-1-methyl-4-phenylpyrrolidine-2-one; |
| 26 | rel-(4R,5R)-5-{hydroxy[5-(1-oxidopyridin-3-yl)-2-thienyl]methyl}-1-methyl-4-phenylpyrrolidin-2-one; |
| 29 | rel-(4R,5R)-5-[2,2'-bithien-5-yl)hydroxy)methyl]-1-methyl-4-phenylpyrrolidin-2-one; |
| 30 | rel-(4R,5R)-5-[[5-(2,6-difluorophenyl)-2-thienyl](hydroxy)methyl]-1-methyl-4-phenylpyrrolidin-2-one; |
| 31 | rel-(4R,5R)-5-{hydroxy[5-(3-methoxyphenyl)-2-thienyl]methyl}-1-methyl-4-phenylpyrrolidin-2-one; |
| 34 | rel-(4R,5R)-5-(hydroxy{5-[2-(trifluoromethyl)phenyl]-2-thienyl}methyl)-1-methyl-4-phenylpyrrolidin-2-one; |
| 35 | rel-(4R,5R)-5-{hydroxy[5-(thiomorpholin-4-ylsulfonyl)-2-thienyl]methyl}-1-methyl-4-phenylpyrrolidin-2-one; |
| 36 | rel-(4R,5R)-5-{hydroxy[5-(morpholin-4-ylsulfonyl)-2-thienyl]methyl}-1-methyl-4-phenylpyrrolidin-2-one; |
| 37 | rel-(4R,5R)-5-[(5-{[4-(4-fluorophenyl)piperazin-1-yl]sulfonyl}-2-thienyl)(hydroxy)methyl]-1-methyl-4-phenylpyrrolidin-2-one; |
| 38 | rel-(4R,5R)-5-[hydroxy(5-methyl-4-phenyl-2-thienyl)methyl]-1-methyl-4-phenylpyrrolidin-2-one; |
| 43 | rel-(4R,5R)-5-[hydroxy(5-methyl-3-phenyl-2-thienyl)methyl]-1-methyl-4-phenylpyrrolidin-2-one; |
| 44 | rel-(4R,5R)-5-{hydroxy[5-(3-nitrophenyl)-2-thienyl]methyl}-1-methyl-4-phenylpyrrolidin-2-one; |
| 50 | rel-(4R,5R)-5-[hydroxy(5-pyridin-2-yl-2-thienyl)methyl]-1-methyl-4-phenylpyrrolidin-2-one; |
| 51 | rel-(4R,5R)-5-[[5-(4-chlorophenyl)-2-thienyl](hydroxy)methyl]-1-methyl-4-phenylpyrrolidin-2-one; |
| 52 | rel-(4R,5R)-5-{hydroxy[5-(4-hydroxyphenyl)-2-thienyl]methyl}-1-methyl-4-phenylpyrrolidin-2-one; |
| 53 | rel-5-[(5-fluoro-3-methyl-1-benzothien-2-yl)(hydroxy)methyl]-1-methyl-4-phenylpyrrolidin-2-one; |
| 55 | rel-(4R,5R)-5-[{5-[(E)-2-(4-fluorophenyl)vinyl]-2-thienyl}(hydroxy)methyl]-1-methyl-4-phenylpyrrolidin-2-one; |
| 57 | rel-(4R,5R)-5-[{5-[2-(4-fluorophenyl)ethyl]-2-thienyl}-(hydroxy)methyl]-1-methyl-4-phenylpyrrolidin-2-one; |
| 58 | rel-(4R,5R)-5-(hydroxy{5-[(4-methoxyphenyl)sulfonyl]-2-thienyl}methyl)-1-methyl-4-phenylpyrrolidin-2-one; |
| 62 | rel-(4R,5R)-5-[{5-[(4-chlorophenyl)sulfonyl]-2-thienyl}-(hydroxy)methyl]-1-methyl-4-phenylpyrrolidin-2-one; |
| 66 | rel-(4R,5R)-5-{hydroxy[5-(phenylthio)-2-thienyl]methyl}-1-methyl-4-phenylpyrrolidin-2-one; |
| 67 | rel-(4R,5R)-5-[[5-(3-aminophenyl)-2-thienyl](hydroxy)methyl]-1-methyl-4-phenylpyrrolidin-2-one; |
| 68 | rel-4-(5-{hydroxy[(2R,3R)-1-methyl-5-oxo-3-phenylpyrrolin-2-yl]methyl}-2-thienyl)benzoic acid; |
| 70 | rel-(4R,5R)-5-{hydroxy[5-(phenylsulfonyl)-2-thienyl]methyl}-1-methyl-4-phenylpyrrolidin-2-one; |
| 71 | rel-(4R,5R)-5-[[5-(2-fluorophenyl)-2-thienyl]-(hydroxy)methyl]-1-methyl-4-phenylpyrrolidin-2-one; |
| 72 | rel-(4R,5R)-5-[[5-(2-fluoro-4-methylphenyl)-2-thienyl]-(hydroxy)methyl]-1-methyl-4-phenylpyrrolidin-2-one; |
| 73 | rel-N-[3-(5-{hydroxy[(2R,3R)-1-methyl-5-oxo-3-phenyl-pyrrolidin-2-yl]methyl}-2-thienyl)phenyl]-methanesulfonamide; |
| 74 | rel-(4R,5R)-5-[{5-[3-(dimethylamino)phenyl]-2-thienyl}-(hydroxy)methyl]-1-methyl-4-phenylpyrrolidin-2-one; |
| 76 | rel-(4R,5R)-5-[{5-[(4-fluorophenyl)sulfonyl]-2-thienyl}-(hydroxy)methyl]-1-methyl-4-phenylpyrrolidin-2-one; |
| 78 | rel-(4R,5R)-5-[hydroxy(5-pyridin-3-yl-2-thienyl)methyl]-1-methyl-4-phenylpyrrolidin-2-one; |
| 79 | rel-(4R,5R)-5-[hydroxy(5-pyridin-3-yl-2-thienyl)methyl]-1-methyl-4-phenylpyrrolidin-2-one hydrochloride; |
| 80 | rel-4-(5-{hydroxy[(2R,3R)-1-methyl-5-oxo-3-phenylpyrrolidin-2-yl]methyl}-2-thienyl)benzonitrile; |
| 83 | rel-(4R,5R)-4-(2-fluorophenyl)-5-[hydroxy(5-phenyl-2-thienyl)-methyl]-1-methylpyrrolidin-2-one; |
| 84 | rel-(4R,5R)-4-(2-fluorophenyl)-5-[[5-(4-fluorophenyl)-2-thienyl](hydroxy)methyl]-1-methylpyrrolidin-2-one; |
| 85 | rel-(4R,5R)-4-(3-fluorophenyl)-5-[[5-(4-fluorophenyl)-2-thienyl](hydroxy)methyl]-1-methylpyrrolidin-2-one; |
| 88 | rel-(4R,5R)-5-[[(4-fluorophenyl)-2-thienyl](hydroxy)methyl]-4-(2-methoxyphenyl)-1-methylpyrrolidin-2-one; |
| 89 | rel-(4R,5R)-4-(2-fluorophenyl)-5-{hydroxy[5-(phenyl-sulfonyl)-2-thienyl]methyl}-1-methylpyrrolidin-2-one; |
| 90 | rel-(4R,5R)-5-[1-benzothien-2-yl(hydroxy)methyl]-4-(2-fluorophenyl)-1-methylpyrrolidin-2-one; |
| 91 | rel-(4R,5R)-5-{hydroxy[5-(phenylsulfonyl)-2-thienyl]methyl}-4-(2-methoxyphenyl)-1-methylpyrrolidin-2-one; |
| 92 | rel-(4R,5R)-5-[{5-[(4-chlorophenyl)sulfonyl]-2-thienyl}-(hydroxy)methyl]-4-(2-methoxyphenyl)-1-methylpyrrolidin-2-one; |
| 98 | rel (4R,5R)-5-[biphenyl-3-yl(hydroxy)methyl]-1-methyl-4-phenylpyrrolidin-2-one; |
| 99 | rel-(4R,5R)-5-[(3,4-dichlorophenyl)(hydroxy)methyl]-1-methyl-4-phenylpyrrolidin-2-one; |
| 124 | rel-(4R,5R)-5-[3-(4-fluorophenyl)-1-hydroxyprop-2-yn-1-yl]-1-methyl-4-phenylpyrrolidin-2-one; |
| 126 | rel-(4R,5R)-5-[3-(2-chlorophenyl)-1-hydroxyprop-2-yn-1-yl]-1-methyl-4-phenylpyrrolidin-2-one; |
| 127 | rel-(4R,5R)-5-[3-(2-fluorophenyl)-1-hydroxyprop-2-yn-1-yl]-1-methyl-4-phenylpyrrolidin-2-one; |
| 131 | rel-(4R,5R)-5-{3-[3-(2,5-dimethyl-1H-pyrrol-1-yl)-phenyl]-1-hydroxyprop-2-yn-1-yl}-1-methyl-4-phenyl-pyrrolidin-2-one; |
| 133 | rel-(4R,5R)-5-[3-(3-aminophenyl)-1-hydroxyprop-2-yn-1-yl]-1-methyl-4-phenylpyrrolidin-2-one; |
| 145 | rel-(4R,5R)-5-[hydroxy(5-phenyl-2-thienyl)methyl]-1-methyl-4-phenylpyrrolidin-2-one; |
| 146 | (4R,5R)-5-[[5-(4-fluorophenyl)-2-thienyl](hydroxy)methyl]-1-methyl-4-phenylpyrrolidin-2-one; |
| 147 | (4R,5R)-5-[hydroxy(5-pyridin-2-yl-2-thienyl)methyl]-1-methyl-4-phenylpyrrolidin-2-one; |
| 148 | (4R,5R)-5-[hydroxy(5-pyridin-3-yl-2-thienyl)methyl]-1-methyl-4-phenylpyrrolidin-2-one; |
| 149 | (4R,5R)-5-{hydroxy[5-(phenylsulfonyl)-2-thienyl]methyl}-1-methyl-4-phenylpyrrolidin-2-one; |

-continued

| Example Number | IUPAC Name |
|---|---|
| 150 | rel-(4R,5R)-4-(2-fluorophenyl)-5-[hydroxy(2-thienyl)-methyl]-1-methylpyrrolidin-2-one; |
| 151 | rel-(4R,5R)-4-(2-fluorophenyl)-5-[hydroxy(5-pyridin-3-yl-3-thienyl)methyl]-1-methylpyrrolidin-2-one; |
| 152 | rel-(4R,5R)-4-(2-fluorophenyl)-5-[hydroxy(5-pyridin-3-yl-2-thienyl)methyl]-1-methylpyrrolidin-2-one hydrochloride; |
| 153 | rel-(4R,5R)-4-(2-fluorophenyl)-5-[hydroxy)5-pyridin-2-yl-2-thienyl)methyl]-1-methylpyrrolidin-2-one; |
| 154 | rel-(4R,5R)-5-[(3-chlorophenyl)(hydroxy)methyl]-4-(2-fluorophenyl)-1-methylpyrrolidin-2-one; |
| 155 | rel-(4R,5R)-5-[2,2'-bithien-5-yl(hydroxy)methyl]-4-(2-fluorophenyl)-1-methylpyrrolidin-2-one. |

15. A pharmaceutical composition comprising a compound of claim 1 and a pharmaceutically acceptable carrier.

16. A method of treating a mammal having a condition of osteoporosis, osteopenia, ovarian cancer, breast cancer, endometrial cancer, endometriosis, prostate cancer, acne, androgen-dependent hair loss, non-insulin-dependent diabetes mellitus, or hypercholesterolemia comprising administering to said mammal an effective amount of a compound having the formula

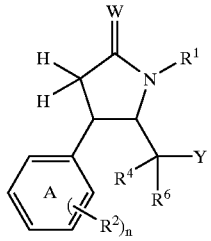

(I)

wherein
  the phenyl group labeled A and the group —C(R$^4$)(R$^6$)Y are oriented cis to each other;
  W represents O or S;
  R$^1$ represents
    —H; or
    —(C$_1$–C$_4$)alkyl which is optionally substituted with up to three halogens;
  n represents 0 or an integer of 1–3;
  R$^2$ represents
    —N(R$^3$)$_2$,
    —OR$^3$,
    —SR$^3$,
    -halogen,
    -phenyl which is optionally substituted with halogen up to perhalo, or
    —(C$_1$–C$_4$)alkyl which is optionally substituted with halogen, —OR$^3$, or SR$^3$; the number of said substituents being up to three for halogen, and up to two for any combination of said —OR$^3$ and —SR$^3$ moieties; and wherein
      R$^3$ represents —H or —(C$_1$–C$_4$)alkyl which is optionally substituted with up to three halogens;
  R$^4$ represents —H or a bond terminating at the ortho position of phenyl ring A;

Y represents fluorine, —OR$^5$, or —SR$^5$; wherein
    R$^5$ represents
      —H;
      —(C$_1$–C$_4$)alkyl optionally substituted with up to three halogens;
      -phenyl which is optionally substituted with halogen, —OR$^{3A}$, —SR$^{3A}$, or —R$^{3A}$, the number of said substituents being up to perhalo for halogen, and up to two for any combination of said —OR$^{3A}$, —SR$^{3A}$, and —R$^{3A}$ moieties; wherein
        R$^{3A}$ represents —(C$_1$–C$_4$)alkyl optionally substituted with up to three halogens; and
      with the proviso that R$^5$ may represent an optionally substituted phenyl group only if R$^6$ represents H;
      —(C$_1$–C$_4$)alkyl-phenyl in which the alkyl portion is optionally substituted with up to three halogens; and the phenyl portion is optionally substituted with halogen, —OR$^{3A}$, —SR$^{3A}$, or —R$^{3A}$, the number of substituents on said phenyl portion being up to perhalo for halogen, and up to two for any combination of said —OR$^{3A}$, —SR$^{3A}$, and —R$^{3A}$ moieties; or
      —(C$_1$–C$_4$)acyl optionally substituted with up to three halogens;
  R$^6$ represents
  1) —H; with the proviso that when R$^6$ is H, then Y is OR$^5$ wherein R$^5$ is phenyl which is optionally substituted with halogen, —OR$^{3A}$, —SR$^{3A}$, or —R$^{3A}$; the number of said substituents being up to perhalo for halogen, and up to two for any combination of said —OR$^{3A}$, —SR$^{3A}$, and —R$^{3A}$ moieties;

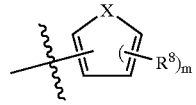

2)
    wherein
    m represents 0 or an integer of 1–3;
    X represents O or S;
    R$^8$ represents
    a) —(C$_6$–C$_{10}$)aryl, which is optionally substituted with one or more substituents selected from
      -halogen,
      —N(R$^3$)$_2$;
      —OR$^3$;
      —SR$^3$;
      —CO$_2$R$^3$;
      —NO$_2$;
      —CN;
      —(C$_1$–C$_6$)alkyl optionally substituted with up to three halogens;
      -phenyl which is optionally substituted with halogen, —OR$^{3A}$, —SR$^{3A}$, or
        —R$^{3A}$; the number of said substituents being up to perhalo for halogen, and up to two for any combination of said —OR$^{3A}$, —SR$^{3A}$, and —R$^{3A}$ moieties;
      -heteroaryl of 5 members and containing 1–2 heteroatoms selected from N, O, and S;
      —NHCOR$^9$; in which
        R$^9$ represents R$^{3A}$ or -phenyl which is optionally substituted with halogen up to perhalo;
      —NHCONHR$^9$; and
      —NHSO$_2$R$^9$;

the number of substituents on said $(C_6-C_{10})$aryl group being up to perhalo for halogen, and up to three for any combination of said —N(R$^3$)$_2$, —OR$^3$, —SR$^3$, —CO$_2$R$^3$, —NO$_2$, —CN, —(C$_1$-C$_6$)alkyl, -phenyl, -heteroaryl, —NHCOR$^9$, —NHCONHR$^9$, and —NHSO$_2$R$^9$ moieties;

b) -heteroaryl of 5–10 members and containing 1–3 heteroatoms selected from
  N, O, and S; and being optionally substituted with halogen, —N(R$^3$)$_2$, —OR$^{3A}$, —SR$^{3A}$, —CO$_2$R$^3$, —NO$_2$, —CN, or —(C$_1$-C$_6$)alkyl which is optionally substituted with up to three halogens; the number of said substituents on the heteroaryl group being up to perhalo for halogen, and up to two for any combination of said —N(R$^3$)$_2$, —OR$^{3A}$, —SR$^{3A}$, —CO$_2$R$^3$, —NO$_2$, —CN, and —(C$_1$-C$_6$)alkyl moieties;

c) —(C$_2$)alkynyl-R$^{10}$ wherein
  R$^{10}$ represents H; R$^{3A}$; or -phenyl which is optionally substituted with halogen, —OR$^3$, —SR$^3$, or —R$^{3A}$; the number of said substituents being up to perhalo for halogen, and up to two for any combination of said —OR$^3$, —SR$^3$, and —R$^{3A}$ moieties;

d) —(C$_1$-C$_4$)alkyl-R$^{11}$ wherein
  the alkyl portion is optionally substituted with halogen, —OR$^3$, or —SR$^3$; the number of said substituents being up to three for halogen, and up to two for any combination of said —OR$^3$ and —SR$^3$ moieties; and
  R$^{11}$ represents
    —H, provided that m is 2 or 3; or
    -phenyl optionally substituted with halogen up to perhalo;

e) —S(O)$_{0-2}$R$^{12}$ wherein
  R$^{12}$ represents
    —(C$_1$-C$_6$)alkyl optionally substituted with halogen;

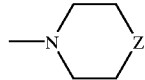

wherein
Z represents O, S(O)$_{0-2}$, C(R$^3$)$_2$, or NR$^{13}$ wherein R$^{13}$ represents R$^{3A}$; or -phenyl which is optionally substituted with halogen, —OR$^{3A}$, SR$^{3A}$, or —(C$_1$-C$_2$)alkyl optionally substituted with up to three halogens; the number of said substituents on phenyl being up to perhalo for halogen, and up to two for any combination of said —OR$^{3A}$, SR$^{3A}$, and —(C$_1$-C$_2$)alkyl moieties;
  -phenyl, optionally substituted with halogen, —OR$^3$ or —R$^{3A}$; the number of said substituents being up to perhalo for halogen, and up to two for any combination of said —OR$^3$ and —R$^{3A}$ moieties; or
  -heteroaryl of 5–6 members and containing 1–3 heteroatoms selected from N, O, and S;

f) —C(R$^{14}$)=CHR$^{14}$ wherein
  R$^{14}$ represents H; -halogen; —OR$^{3A}$; or phenyl optionally substituted with halogen or with —R$^{3A}$; the number of said substituents being up to perhalo for halogen, and up to two for —R$^{3A}$ moieties; and
  with the proviso that when 2 such alkenyl groups are adjacent to each other, they may be joined, and taken together with the ring atoms to which they are attached, constitute a fused 6-membered ring;

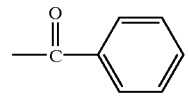

g)
optionally substituted with halogen, —OR$^{3A}$ or —(C$_1$-C$_6$)alkyl optionally substituted with up to three halogens; the number of said substituents on phenyl being up to perhalo for halogen, and up to two for any combination of said —OR$^{3A}$ or —(C$_1$-C$_6$)alkyl moieties;

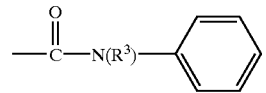

h)
wherein the phenyl ring is optionally substituted with halogen, —OR$^{3A}$, or —(C$_1$-C$_6$)alkyl optionally substituted with up to three halogens; the number of said substituents on phenyl being up to perhalo for halogen, and up to two for any combination of said —OR$^{3A}$ and —(C$_1$-C$_6$)alkyl moieties;

i)

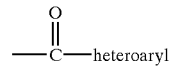

wherein the heteroaryl ring contains 5–6 members and up to 3 heteroatoms selected from N, O, and S, and is optionally substituted with up to 2 substitutents R$^{3A}$;

3) —(C$_1$-C$_4$)alkyl-R$^{15}$ wherein
the alkyl portion is optionally substituted with up to three halogens; and
R$^{15}$ represents
  -phenyl optionally substituted with halogen, —R$^{3A}$, —OR$^{3A}$, or with -phenyl' optionally substituted with halogen up to perhalo; the number of said substituents on said phenyl being up to perhalo for halogen, and up to two for any combination of said —R$^{3A}$, —OR$^{3A}$, or -phenyl' moieties; or
  a heteroaryl ring of 5–6 members and containing up to 3 heteroatoms selected from N, O, and S, and optionally bearing up to 2 substituents selected from halogen, —R$^{3A}$, —OR$^{3A}$, and -phenyl optionally substituted with halogen up to perhalo;

4) —CH=CH—(C$_6$-C$_{10}$)aryl-(R$^{16}$)$_s$ wherein
s represents 0 or an integer of 1–4;
R$^{16}$ represents a substituent selected from halogen, —R$^{3A}$, —N(R$^3$)$_2$, —OR$^{3A}$, —SR$^{3A}$, —NO$_2$, and —CO$_2$R$^3$;

5) —CH=CH-heteroaryl wherein the heteroaryl ring contains 5–6 members and up to 3 heteroatoms selected from N, O, and S; and is optionally substituted with R$^{3A}$;

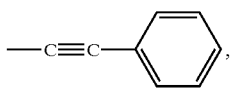

6) optionally substituted with halogen, —$R^{3A}$; —$N(R^3)_2$; —$OR^{3A}$; —$SR^{3A}$; —$NO_2$; —$CO_2R^3$; phenyl' optionally substituted with halogen up to perhalo; and -heteroaryl of 5–6 members and containing up to 3 heteroatoms selected from N, O, and S and optionally substituted with up to 2 substituents $R^{3A}$; the number of said substituents on phenyl being up to perhalo for halogen, and up to two for any combination of said —$R^{3A}$; —$N(R^3)_2$; —$OR^{3A}$; —$SR^{3A}$: —$NO_2$; —$CO_2R^3$; and phenyl' moieties;

7) —C≡C-heteroaryl wherein the heteroaryl ring contains 5–6 members and up to 3 heteroatoms selected from N, O, and S, and is optionally substituted with up to 2 substituents $R^{3A}$;

8) —C=C—$CH_2$—$R^{12}$ 9) phenyl, optionally substituted with halogen up to perhalo, this phenyl being also optionally substituted with up to 2 substituents selected from -phenyl', optionally substituted with halogen, —$NHCOR^3$, —$N(R^3)_2$, —$OR^3$, or —$NO_2$; the number of said substituents being up to perhalo for halogen, and up to two for any combination of said —$NHCOR^3$, —$N(R^3)_2$, —$OR^3$, and —$NO_2$ moieties;

-heteroaryl of 5–6 members and containing up to 3 heteroatoms selected from N, O, and S;
—$R^{3A}$;
—$OR^3$;
—$SR^3$;
—$N(R^3)_2$; and
—$CF_3$;

10)
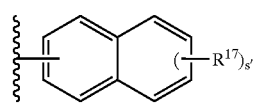

wherein
s' represents 0, 1, or 2; and
$R^{17}$ represents halogen; $R^{3A}$; —$OR^3$; or —$N(R^3)_2$;

11)
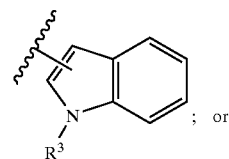
; or

12)
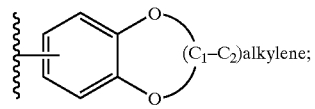

and with the further provisos that:
an aliphatic carbon atom attached to oxygen may not also bear a halogen substituent;
when any alkyl group is attached to O, S, or N, and bears a hydroxyl substituent, then said hydroxyl substituent is separated by at least two carbon atoms from the O, S, or N to which the alkyl group is attached; and
two alkyl groups located on the same N atom they may be linked by a bond, an O, an S, or $NR^3$ to form a N-containing heterocycle of 5–7 ring atoms;

or a pharmaceutically acceptable salt thereof or N-oxide thereof.

17. The method of claim 16 wherein the mammal is a human.

* * * * *